US010550430B2

(12) United States Patent
Sahin et al.

(10) Patent No.: US 10,550,430 B2
(45) Date of Patent: Feb. 4, 2020

(54) METHOD AND KIT FOR DETERMINING WHETHER A SUBJECT SHOWS AN IMMUNE RESPONSE

(71) Applicants: Biontech AG, Mainz (DE); TRON—Translationale Onkologie an der Universitätsmedizin der Johannes Gutenberg—Universität Mainz gemeinnutzige GmbH, Mainz (DE)

(72) Inventors: Ugur Sahin, Mainz (DE); Michael Schäfer, Homburg-Sanddorf (DE); Marta Magdalena Faryna, Mainz (DE); Tana Omokoko, Mainz (DE); Lisa Hebich, Mainz (DE); Petra Simon, Mainz (DE); Annett Reichardt, Erbenhausen (DE); Özlem Öz, Idstein (DE)

(73) Assignees: BIONTECH DIAGNOSTICS GMBH, Mainz (DE); TRON—TRANSLATIONALE ONKOLOGIE AN DER UNIVERSITATSMEDIZIN DER JOHANNES GUTENBERG—UNIVERSITAT MAINZ GEMEINNUTZIGE GMBH, Mainz (DE)

( * ) Notice: Subject to any disclaimer, the term of this patent is extended or adjusted under 35 U.S.C. 154(b) by 76 days.

(21) Appl. No.: 15/031,415

(22) PCT Filed: Oct. 24, 2014

(86) PCT No.: PCT/EP2014/072854
§ 371 (c)(1),
(2) Date: Apr. 22, 2016

(87) PCT Pub. No.: WO2015/059277
PCT Pub. Date: Apr. 30, 2015

(65) Prior Publication Data
US 2016/0265050 A1    Sep. 15, 2016

(30) Foreign Application Priority Data
Oct. 25, 2013 (WO) ................ PCT/EP2013/003229

(51) Int. Cl.
*C12Q 1/68* (2018.01)
*C07H 21/04* (2006.01)
*C12Q 1/6881* (2018.01)
*C12Q 1/6876* (2018.01)

(52) U.S. Cl.
CPC ......... *C12Q 1/6881* (2013.01); *C12Q 1/6876* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 5,593,830 | A | * | 1/1997 | Santamaria | .......... | C12Q 1/6881 |
| | | | | | | 435/6.11 |
| 5,962,272 | A | | 10/1999 | Chenchik et al. | | |
| 5,972,604 | A | * | 10/1999 | Santamaria | .......... | C12Q 1/6827 |
| | | | | | | 435/6.11 |
| 2004/0224009 | A1 | * | 11/2004 | Albani | ................ | C12N 5/0006 |
| | | | | | | 424/450 |
| 2007/0258952 | A1 | * | 11/2007 | Tong | ....................... | C12N 7/00 |
| | | | | | | 424/93.2 |
| 2012/0225427 | A1 | | 9/2012 | Mallat et al. | | |
| 2013/0225427 | A1 | | 8/2013 | Albani | | |

FOREIGN PATENT DOCUMENTS

| WO | WO2002/13861 | * | 2/2002 | .......... A61K 39/395 |
| WO | WO2012038055 | | 3/2012 | |
| WO | WO-2012083240 A2 | * | 6/2012 | .......... C12Q 1/6881 |
| WO | WO-2014043813 A1 | * | 3/2014 | .......... C12Q 1/6881 |

OTHER PUBLICATIONS

Putintseva et al. Frontiers in immunology, vol. 4, Article 463, 1-12, Dec. 2013 (Year: 2013).*
Freeman et al. (Genome Research, vol. 19, pp. 1817-1824, 2009) (Year: 2009).*
Pinto et al. (Analytical Biochemistry, vol. 397, pp. 227-232, 2010). (Year: 2010).*
International Search Report and Written Opinion for PCT/EP2014/072854 dated Feb. 18, 2015.
International Preliminary Report on Patentability for PCT/EP2014/072854 dated May 6, 2016.
Elboim, et al., "HSV-2 Specifically Down Regulates HLA-C Expression to Render HSV-2-Infected DCs Susceptible to NK Cell Killing," PLOS Pathogens, vol. 9, Issue 3, Mar. 2013.
La Gruta, et al., "Interrogating the relationship between naive and immune antiviral T cell repertoires," Current Opinion in Virology, 2013, 3:447-451.
Liu, et al., "Mechanisms for Genetically Predetermined Differential Quantitative Expression of HLA-A and -B Antigens," Human Immunology, 61, 799-807 (2000).
Quigley, et al., "Unbiased Molecular Analysis of T Cell Receptor Expression Using Template-Switch Anchored RT-PCR," Current Protocols in Immunology, 10.33.1-10.33.16, Aug. 2011.

* cited by examiner

*Primary Examiner* — Jeanine A Goldberg
(74) *Attorney, Agent, or Firm* — Neal, Gerber & Eisenberg LLP; Kevin A. O'Connor

(57) ABSTRACT

The present invention relates to a kit and a method for determining whether a subject shows an immune response against an antigen.

20 Claims, 17 Drawing Sheets
Specification includes a Sequence Listing.

| | |
|---|---|
| C*# | C*14:34, C*14:31, C*14:30, C*14:57, C*14:33, C*14:58, C*14:18, C*14:11, C*14:44, C*14:23, C*14:59, C*14:67, C*14:60, C*01:97, C*14:07N, C*14:02:15, C*14:02:11, C*14:02:01, C*14:02:10, C*14:02:16, C*14:02:07 |

Figure 12A
| Mix 1 | Ratio 1 | Ratio 2 | Ratio 3 | Ratio 4 |
|---|---|---|---|---|
| A0201 | 18% | 17% | 14% | 11% |
| A2301 | 18% | 17% | 14% | 11% |
| B0702 | 9% | 17% | 29% | 44% |
| B5301 | 18% | 17% | 14% | 11% |
| C0401 | 18% | 17% | 14% | 11% |
| C1203 | 18% | 17% | 14% | 11% |
Figure 12B
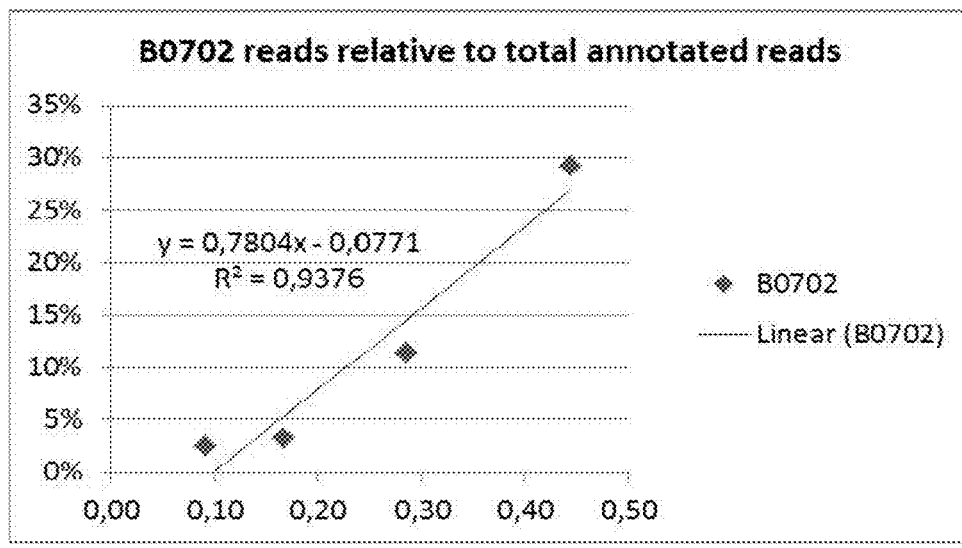
Figure 12C
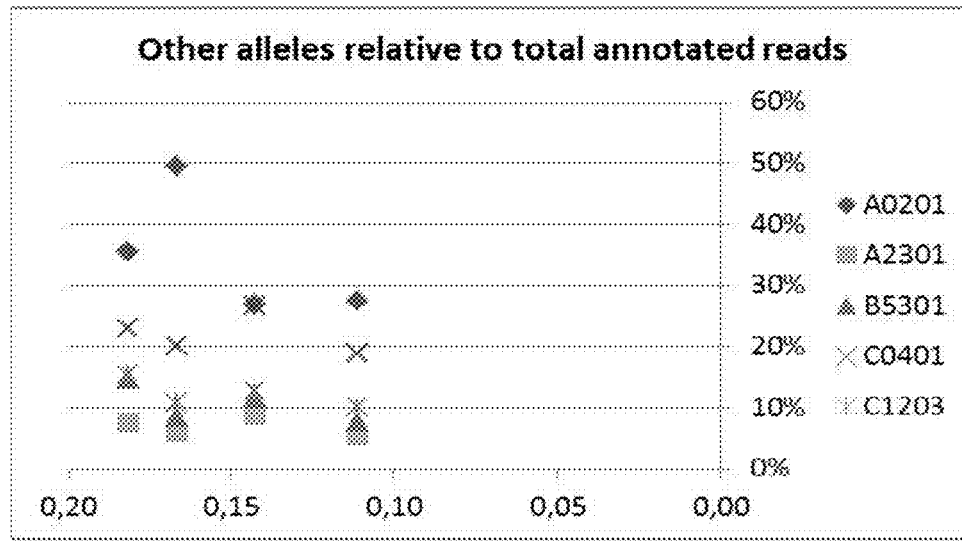

Figure 13A
| Mix 2 | Ratio 1 | Ratio 2 | Ratio 3 | Ratio 4 |
|---|---|---|---|---|
| A0201 | 9% | 17% | 29% | 44% |
| A2402 | 18% | 17% | 14% | 11% |
| B1801 | 18% | 17% | 14% | 11% |
| B5301 | 18% | 17% | 14% | 11% |
| C0702 | 18% | 17% | 14% | 11% |
| C1502 | 18% | 17% | 14% | 11% |
Figure 13B
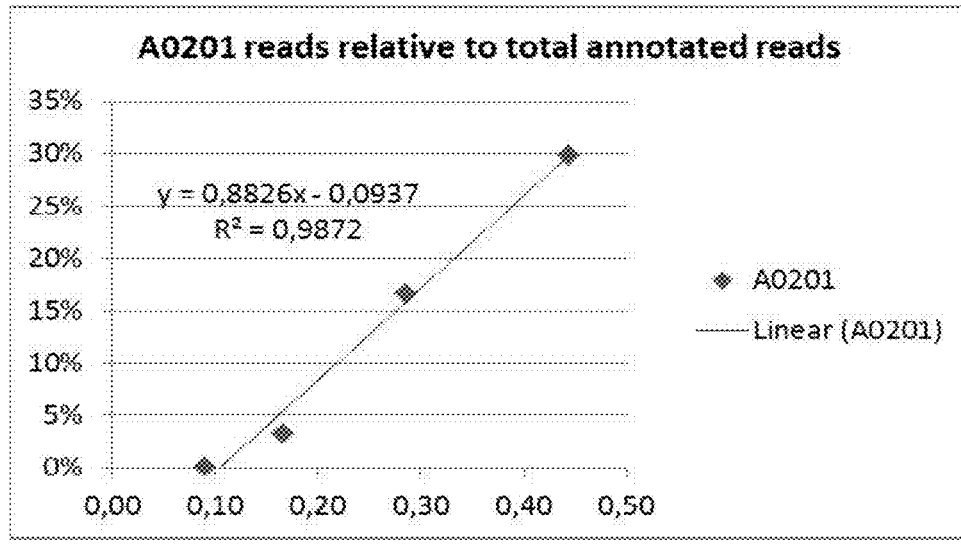
Figure 13C
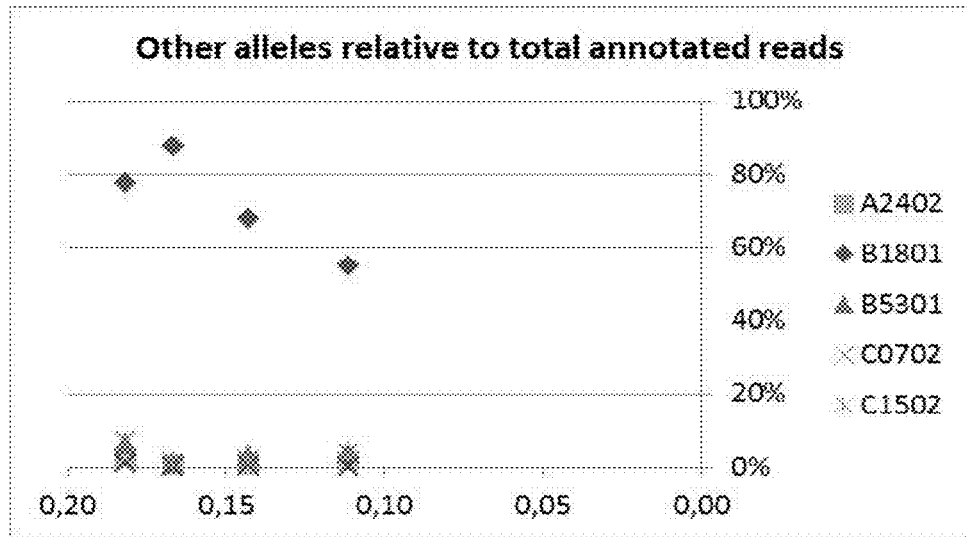

Figure 14A
| Mix 3 | Ratio 1 | Ratio 2 | Ratio 3 | Ratio 4 |
|---|---|---|---|---|
| A2403 | 18% | 17% | 14% | 11% |
| A6802 | 18% | 17% | 14% | 11% |
| B3501 | 18% | 17% | 14% | 11% |
| B4402 | 18% | 17% | 14% | 11% |
| C0801 | 18% | 17% | 14% | 11% |
| C1203 | 9% | 17% | 29% | 44% |
Figure 14B
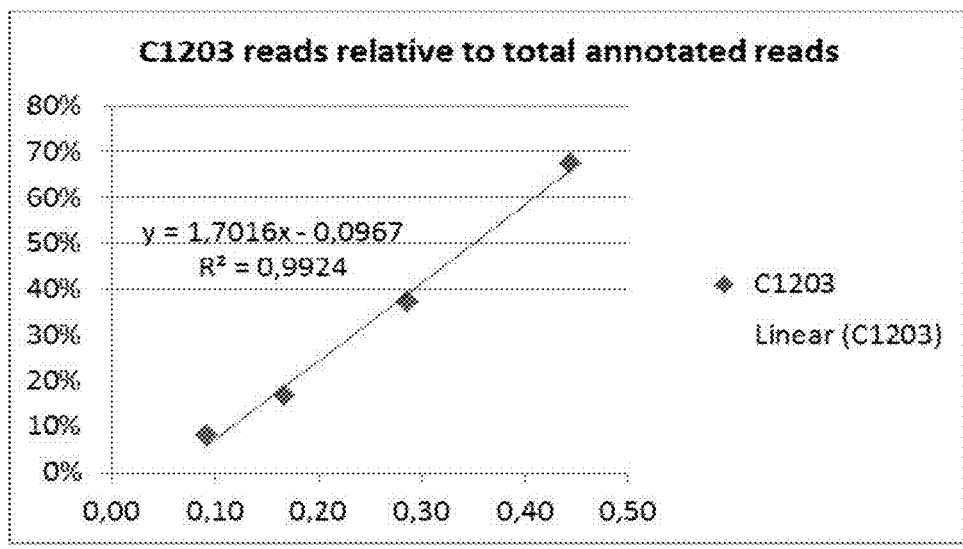
Figure 14C
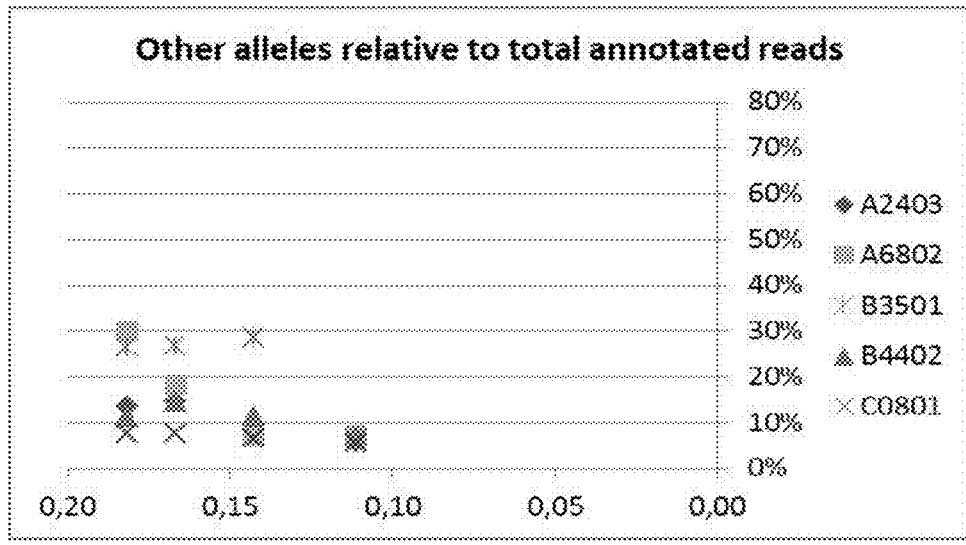

METHOD AND KIT FOR DETERMINING WHETHER A SUBJECT SHOWS AN IMMUNE RESPONSE

CROSS-REFERENCE TO RELATED APPLICATIONS

This application is a national stage entry of international application PCT/EP2014/072854, filed on Oct. 24, 2014, which claimed priority to international application PCT/EP2013/003229, filed on Oct. 25, 2013, the entire contents of which are incorporated herein by reference.

BACKGROUND

The evolution of the immune system of vertebrates resulted in a highly effective network based on two types of defense: the innate and the adoptive immunity.

In contrast to the evolutionary ancient innate immune system that relies on invariant receptors recognizing common molecular patterns associated with pathogens, adoptive immunity is based on highly specific antigen receptors on B cells (B lymphocytes) and T cells (T lymphocytes) and clonal selection of these cells.

T cells play a central role in cell-mediated immunity in humans and animals. The recognition and binding of a particular antigen is mediated by the T cell receptors (TCRs) expressed on the surface of T cells. The T cell receptor of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell.

In order to be able to target a vast variety of antigens, the T cell receptors need to have a great diversity. This diversity is obtained by genetic rearrangement of different discontinuous segments of genes which code for the different structural regions of TCRs. TCRs are composed of one α-chain and one β-chain or of one γ-chain and one δ-chain. The TCR α/β chains are composed of an N-terminal highly polymorphic variable region involved in antigen recognition and an invariant constant region. On the genetic level, these chains are separated into several regions, a variable (V) region, a diversity (D) region (only β- and δ-chain), a joining (J) region and a constant (C) region. The human β-chain genes contain over 60 variable (V), 2 diversity (D), over 10 joining (J) segments, and 2 constant region segments (C). The human α-chain genes contain over 50 V segments, and over 60 J segments but no D segments, as well as one C segment. The murine β-chain genes contain over 30 variable (V), 2 diversity (D), over 10 joining (J) segments, and 2 constant region segments (C). The murine α-chain genes contain almost 100 V segments, 60 J segments, no D segments, but one C segment. During the differentiation of T cells, specific T cell receptor genes are created by rearranging one V, one D (only β- and δ-chain), one J and one C region gene. The diversity of the TCRs is further amplified by imprecise V-(D)-J rearrangement wherein random nucleotides are introduced and/or deleted at the recombination sites. Since the rearrangement of the TCR gene loci occurs in the genome during maturation of T cells, each mature T cell only expresses one specific α/β TCR or γ/δ TCR.

MHC and antigen binding is mediated by the complementary determining regions 1, 2 and 3 (CDR1, CDR2, CDR3) of the TCR. The CDR3 of the β-chain which is most critical for antigen recognition and binding is encoded by the V-D-J junction of the rearranged TCR β-chain gene.

The TCR is a part of a complex signaling machinery, which includes the heterodimeric complex of the TCR α- and β-chains, the co-receptor CD4 or CD8 and the CD3 signal transduction module. While the CD3 chains transfer the activation signal inside the cell, the TCR α/β heterodimer is solely responsible for antigen recognition.

The role of the adaptive immune system in response to infectious diseases, cancers and allergic diseases has been investigated for years. Key players are immune receptors generated by the statistic recombination of genes with the potential to provide unique binding properties to recognize foreign structures (antigens). Many scientific publications explored the mechanisms for generating the vast diversity of immune receptors, including the selection and expansion or depletion of immune cells bearing a specific receptor. It is well established in the art, that the specific interdependency of immune receptor and antigen can be employed for diagnostic purposes. In fact, many diseases are not diagnosed by detection of the pathogen but by detection of immune receptors, in most cases an antibody, binding to the pathogen or to an antigen of the pathogen.

Most present diagnostic tests rely on the detection of specific antibodies relating to individual diseases but since high throughput methods allow the determination and quantification not only of single immune receptor specificities but of large immune receptor profiles, it is also possible to establish unbiased diagnostic tests. The principle is high throughput sequencing of recombined immune receptor genes in T or B cells, analysis of frequency distribution of receptor bearing T or B cell clones, where frequent clones suggest immune reactions, comparison of the frequent receptor sequences with patient databases to find shared sequences and predicting of potentially analogous diseases. Due to their relevance for antigen binding, the complementarity determining regions are the biological sequences in focus.

αβ-T cells do not recognize free antigens but only those antigen peptides, presented on the cell surface by human leukocyte antigen or major histocompatibility complex proteins. The interaction between the peptide-HLA (pHLA) complex and the respective antigen-specific T cell receptor is determined by the protein structure of the TCR and the structure of the pHLA complex, which are both highly variable. The structures and specificities of TCRs vary from T cell to T cell and in case of HLA molecules between different individuals.

Due to the characteristic germline-encoded structure of their antigen binding groove, HLA molecules can only bind a distinct set of peptides that share characteristic amino acid residues at defined positions. HLAs are divided into subgroups. The HLAs of class I bind to short peptide sequences of 8 to 10 amino acid length and are recognized by CD8 T cells evolving a cellular immune response, while HLAs of class II bind longer peptide sequences of mostly 15 to 24 amino acid length and are recognized by CD4 T cells contributing to the humoral immune response. The class III HLAs encode components of the complement system. There are three major HLA class I genes HLA-A, HLA-B, and HLA-C. All three are located on the short p arm of chromosome 6. These genes encode the α-chain of the HLA class I protein. The alpha chain comprises three protein domains α1-3 encoded by the exons 2-4, wherein α1 and α2 participate in the antigen binding. The one corresponding β-chain is encoded by the β-microglobuline gene located on chromosome 15. HLA of class II also contains three different genes, i.e. HLA-DP, HLA-DQ, and HLA-DR. While HLA-DP and HLA-DQ are each formed by two genes products one encoding the α-chain and one encoding the β-chain located on the short p arm of chromosome 6, HLA-DR is encoded by one gene locus for the alpha chain but four loci for the beat chain (HLA-DRB1 and HLA-DRB3-5) although no more than three beta loci are present in one individual. Each chain comprises two different protein domains α1 and α2 or β1 and (β2, respectively. α1 and β1 are encoded by exon 2 and form the antigen binding grove while α2 and β2 are encoded by exon 3 and do not participate in the antigen binding. Beside these major HLAs, there is a number of so called minor HLAs which may also present antigens at the cell surface (class I minor HLAs: HLA-E, HLA-F and HLA-G). The genes coding for HLA molecules show an extremely high genetic polymorphism resulting in a multitude of different HLA alleles (e.g. 6900 HLA class I alleles in human). Every allele encodes an individual HLA molecule that can only bind a limited set of peptides.

It has recently been established that HLA shapes, to a significant extent, the TCR repertoire of an individual (Melenhorst J. J. et al., Contribution of TCR-beta locus and HLA to the shape of the mature human Vbeta repertoire, J Immunol 2008). Although the TCR repertoire of the naïve T cell pool may not differ substantially between healthy individuals having different HLA, TCR repertoire changes in disease state can correlate with different HLA types (Freeman J. D. et al., Profiling the T cell receptor beta-chain repertoire by massively parallel sequencing, Genome Research 2009). The major factor in formation of the TCR repertoire is the antigenic peptide of the pMHC complex (Koning D. et al., CD8+ TCR Repertoire Formation Is Guided Primarily by the Peptide Component of the Antigenic Complex, J Immunol 2013). However, binding of a certain peptide is restricted to distinct HLA molecules (HLA-restriction of antigen recognition).

Thus, the set of HLA molecules expressed by one individual determines the antigen-recognition by TCRs and the antigen-dependent T cell activation and therefore substantially shapes the TCR repertoire. The investigation of TCR repertoires and their alterations, for example, during disease progression or therapy without knowledge of the HLA status will provide only limited information. Knowledge of HLA expression is crucial for a comprehensive analysis and comparison of measured TCR repertoires.

Since expansion of distinct T cell clones in a disease state correlates with antigen expression and expression of certain HLA alleles, knowledge of the HLA status which includes qualitative and quantitative information relating to the various HLA isotype expressed by a patient is essential for the interpretation of TCR profiles and their alterations, for example in response to a pathogen, a vaccine or in response to the overexpression of a tumor antigen.

HLA typing is usually done separately to TCR profiling using standard genomic DNA-based typing assays, making it time-consuming and expensive. In addition, HLA typing based on genomic DNA may not reflect the in vivo status of expressed and therefore of immunologically relevant HLA molecules. Furthermore, since HLA typing is based on genomic DNA and TCR profiling requires obtaining quantitative and qualitative information of mRNAs encoding TCRs transcribed from recombined T cell receptor loci, a further integration of HLA typing and TCR profiling is prevented.

The present invention aims at overcoming this limitation of the prior art and provides an unbiased diagnostic method for combined profiling of αβ-TCR repertoires and of HLA isotypes in a single assay, which is based on gene expression profiles derived from mRNAs encoding MHC isotypes, in particular HLA-A, HLA-B and HLA-C, and gene expression profiles derived from mRNAs encoding T cell receptor chains transcribed from recombined T cell receptor loci. The combination of RNA-based HLA typing with TCR repertoire profiling will simultaneously provide information about TCR repertoires and their alterations as well as expression status and genotype of the jointly responsible HLA alleles. Knowledge of TCR repertoires and expressed HLA isotypes of a patient at the same time will provide significant advantages towards the development of specific immune therapies. Personalized therapy approaches such as individualized vaccination can only be realized with knowledge of the HLA status of the patient.

The methods and kits described herein below allow simultaneous analysis of the same sample for T cell receptor expression and HLA expression, which is a significant advantage over the prior art methods and reduces time and costs. Moreover, because the sample analyzed can rely on minute amounts of tissue, rather localized information can be obtained (for example from a tumor infiltrated by T cells). In other words, sequence information derived from non-tumor tissue can be avoided. In fact, if a cancer patient is affected from a tumor comprising tumor cells with down-regulated HLA alleles, the method of the present invention allows distinguishing such cells from other tumor cells which do not show a down-regulation of HLA expression.

As demonstrated by the Examples of the present application, in particular by Example 8, the methods described herein below in more detail can be used for monitoring immune responses of cancer patients during an anti-tumor vaccination by establishing HLA- and TCR-specific gene expression profiles derived from a PBMC sample obtained from the patient. This furthermore allows establishing potential differences in anti-tumor effect of a vaccination therapy by showing specific down-regulation of HLA expression in tumor cells in response to an immune stimulation. For more details we refer to Example 8 of the present invention.

SUMMARY OF THE INVENTION

Accordingly, the present invention generally provides a kit and a method useful for determining whether a subject shows an immune response against an antigen.

In one aspect the invention relates to a method for determining whether a subject shows an immune response against at least one antigen, comprising the steps of: (a) establishing gene expression profiles of a first and a second sample, wherein said establishing of gene expression profiles comprises: (i) identifying and quantifying mRNAs encoding MHC class I (MHC I) or MHC class II (MHC II) isotypes and (ii) identifying and quantifying mRNAs encoding T cell receptor chains transcribed from recombined T cell receptor loci, wherein said identifying comprises obtaining nucleotide sequence information allowing to assign the amount of quantified mRNA to individual MHC I or MHC II isotypes and to individual T cell receptor chains; (b) comparing the expression profiles of the first and the second sample; and (c) concluding from the comparison of the expression profiles whether the subject's immune system has responded to the antigen and which individual T cell receptor and which MHC I or MHC II isotype or which group of all potential MHC I or MHC II isotype is involved in the immune response of the subject against said antigen.

In another aspect the invention relates to a method for determining whether a subject shows an immune response against at least one antigen, comprising the steps of: (a) establishing gene expression profiles of a first and a second sample, wherein said establishing of gene expression profiles comprises: (i) identifying and quantifying mRNAs encoding MHC MLA I isotypes, preferably HLA-A, HLA-B and HLA-C, and (ii) identifying and quantifying mRNAs encoding T cell receptor chains transcribed from recombined T cell receptor loci, wherein said identifying comprises obtaining nucleotide sequence information allowing to assign the amount of quantified mRNA to individual MHC MLA I isotypes and to individual T cell receptor chains; (b) comparing the expression profiles of the first and the second sample; and (c) concluding from the comparison of the expression profiles whether the subject's immune system has responded to the antigen and which individual T cell receptor and which MHC/HLA isotype or which group of all potential MHC/HLA isotype is involved in the immune response of the subject against said antigen.

In one embodiment, the second sample is characterized by or suspected of being characterized by comprising T cells, antigen presenting cells presenting said antigen, and an elevated amount of said antigen compared to the first sample.

In another embodiment, the first sample is characterized by comprising T cells.

In another embodiment, the observation of a decreased or reduced amount of at least one mRNA encoding an MHC/HLA isotype and/or the absence of an increased amount of at least one mRNA encoding a TCR α-chain and of at least one mRNA encoding a TCR β-chain are indicative of a suppression of the immune response against said antigen.

In another embodiment, the observation of (1) mRNA encoding at least one MHC/HLA isotype known to be capable of presenting the antigen and of (2) an increased amount of at least one mRNA encoding a TCR α-chain and of at least one mRNA encoding a TCR β-chain, which chains assemble into a T cell receptor known to bind to the antigen when presented by an MHC/HLA molecule or the expression of which is correlated with exposure of the patient to the antigen, indicates that the patient's immune system has responded to the antigen.

In another embodiment, establishing the gene expression profile comprises: (i) reverse transcription of mRNA with a reverse primer hybridizing to a target sequence within a nucleotide sequence transcribed from a conserved region of exon 3 or exon 4 of an MHC/HLA allele and generating a first cDNA strand with a 3' poly (C) sequence comprising at least 3 C nucleotides at the 3' end of said cDNA strand, which poly (C) sequence serves as a target sequence for a template switching oligonucleotide, wherein said template switching oligonucleotide comprises at least 3 G nucleotides and serves as a matrix for the elongation of the first cDNA strand at the 3' end of said poly (C) sequence and introduces a primer binding site at the 3' end of said first cDNA strand, (ii) reproducing the cDNA by polymerase chain reaction, with a forward primer which is capable of hybridizing to said primer binding site.

In a further embodiment, establishing the gene expression profile comprises: (i) reverse transcription of mRNA encoding a TCRα chain and TCRβ chain with a reverse primer hybridizing to a target sequence within a nucleotide sequence encoding the constant region of TCRα and TCRβ chains and generating a first cDNA strand with a 3' poly (C) sequence comprising at least 3 C nucleotides at the 3' end of said cDNA strand, which poly (C) sequence serves as a target sequence for a template switching oligonucleotide, wherein said template switching oligonucleotide comprises at least 3 G nucleotides and serves as a matrix for the elongation of the first cDNA strand at the 3' end of said poly (C) sequence and introduces a primer binding site at the 3' end of said first cDNA strand, and (ii) reproducing the cDNA by polymerase chain reaction, with a forward primer which is capable of hybridizing to said primer binding site.

In a further embodiment, the samples are singularized to establish gene expression profiles of single cell or of groups of single cells.

In a further embodiment, concluding which individual T cell receptor is involved in the immune response comprises: (i) determining the frequency of mRNAs encoding individual TCRα-chain and TCRβ-chain; (ii) concluding on the TCRα-chain and TCRβ-chain of the T cell receptor involved in the immune response by: (a) identifying the TCRα-chain which is encoded by the most frequent mRNA encoding a TCRα-chain, and by (b) identifying the TCRβ-chain which is encoded by the most frequent mRNA encoding a TCRβ-chain; and (iii) validating the T cell receptor by correlation to antigen and MHC/HLA information.

In a further embodiment, the first and the second sample are taken from the same subject.

In a further embodiment, the method of the present invention comprises the additional step of comparing the expression profiles of the subject to at least one expression profile of a different subject or of a group of subjects.

In a further embodiment, the gene expression profile of the first and/or the second sample is used to create a database.

In a further embodiment, the gene expression profile of the first sample is a gene expression profile taken from a database.

In a further embodiment, (a) the antigen is a tumor antigen and said antigen presenting cell is a tumor cell, (b) the antigen is a viral antigen and said antigen presenting cell is a virus infected cell, or (c) the antigen is an auto antigen.

In a further embodiment, the first sample is obtained prior to vaccination of the subject and the second sample is obtained subsequent to vaccination, wherein vaccination comprises administration of at least one antigen.

In another aspect, the present invention relates to a kit for performing the method of the present invention, comprising at least two groups of oligonucleotides, wherein:
the first group (I) comprises:
(I.1) a first oligonucleotide capable of hybridizing to an mRNA transcribed from a recombined T cell receptor locus encoding a TCRα chain, wherein said first oligonucleotide hybridizes to a target sequence within the nucleotide sequence encoding the constant region of the TCRα chain;
(I.2) a first oligonucleotide capable of hybridizing to an mRNA transcribed from a recombined T cell receptor locus encoding a TCRβ chain, wherein said first oligonucleotide hybridizes to a target sequence within the nucleotide sequence encoding the constant region of the TCRβ chain;
(I.3) a first oligonucleotide capable of hybridizing to an mRNA encoding an HLA I isotype, wherein said first oligonucleotide hybridizes to a target sequence within a nucleotide sequence transcribed from a conserved region of exon 3 or exon 4 of an HLA I allele;
(I.4) a template switching oligonucleotide providing a primer binding site and at least 3 consecutive G nucleotides at the 3' end; and the second group (II) comprises:
(II.1) an oligonucleotide which is capable of hybridizing to a nucleotide sequence of the primer binding site provided by the template switching oligonucleotide according to item (I.4) of the first group of oligonucleotides.

In one embodiment, the second group (II) of oligonucleotides further comprises:

(II.2) a second oligonucleotide capable of hybridizing to an mRNA transcribed from a recombined T cell receptor locus encoding a TCRα chain, wherein said second oligonucleotide hybridizes to a target sequence within the nucleotide sequence encoding the constant region of the TCRα chain, wherein the target sequence either comprises the target sequence of said first oligonucleotide which hybridizes to the mRNA encoding the TCRα chain or is located 5' of said target sequence;

(II.3) a second oligonucleotide capable of hybridizing to an mRNA transcribed from a recombined T cell receptor locus encoding a TCRβ chain, wherein said second oligonucleotide hybridizes to a target sequence within the nucleotide sequence encoding the constant region of the TCRβ chain, wherein the target sequence either comprises the target sequence of said first oligonucleotide which hybridizes to the mRNA encoding the TCRβ chain or is located 5' of said target sequence; and (II.4) a second oligonucleotide capable of hybridizing to an mRNA encoding a HLA I isotype, wherein said second oligonucleotide hybridizes to a target sequence within a nucleotide sequence transcribed from a conserved region of exon 3 or exon 4 of an HLA I allele and wherein said target sequence either comprises the target sequence of said first oligonucleotide which hybridizes to mRNA encoding an HLA I isotype or is located 5' of said target sequence; and, optionally, (II.5) a second oligonucleotide hybridizing to a nucleotide sequence which is complementary to the nucleotide sequence of mRNA encoding an HLA I isotype, wherein the complementary sequence of the target sequence to which the oligonucleotide hybridizes is located 5' of nucleotide position 180 of SEQ ID NO: 1 or is located 5' of nucleotide position 97 of SEQ ID NO: 1 and wherein said complementary sequence of the target sequence is a nucleotide sequence encoding a conserved region of an HLA I allele.

In another embodiment, the kit further comprises a third group (III) of oligonucleotides comprising:

(III.1) an oligonucleotide capable of hybridizing to a nucleotide sequence which is complementary to the nucleotide sequence of the primer binding site provided by the template switching oligonucleotide;

(III.2) a third oligonucleotide capable of hybridizing to an mRNA transcribed from a recombined T cell receptor locus encoding a TCRα chain, wherein said third oligonucleotide hybridizes to a target sequence within the nucleotide sequence encoding the constant region of the TCRα chain, wherein the target sequence either comprises the target sequence of said second oligonucleotide which hybridizes to mRNA encoding the TCRα chain or is located 5' of said target sequence;

(III.3) a third oligonucleotide capable of hybridizing to an mRNA transcribed from a recombined T cell receptor locus encoding a TCRβ chain, wherein said third oligonucleotide hybridizes to a target sequence within the nucleotide sequence encoding the constant region of the TCRβ chain, wherein the target sequence either comprises the target sequence of said second oligonucleotide which hybridizes to mRNA encoding the TCRβ chain or is located 5' of said target sequence;

(III.4) an oligonucleotide capable of hybridizing to a nucleotide sequence which is complementary to the nucleotide sequence of mRNA encoding an HLA I isotype, wherein the complementary sequence of the target sequence to which the oligonucleotide hybridizes is preferably located 5' of nucleotide position 180 of SEQ ID NO: 1 or is preferably located 5' of nucleotide position 97 of SEQ ID NO: 1 and wherein said complementary sequence of the target sequence is a nucleotide sequence encoding a conserved region of an HLA I allele; and (III.5) an oligonucleotide hybridizing to mRNA encoding an HLA I isotype, wherein the oligonucleotide hybridizes to target sequence which is preferably located 3' of nucleotide position 561 of SEQ ID NO: 1.

In another embodiment, the first oligonucleotide hybridizing to an mRNA encoding MHC I/HLA I hybridizes to mRNA encoding HLA-A, HLA-B and HLA-C or to mRNA transcribed from a corresponding locus in a cell of a non-human organism.

In another embodiment, the first oligonucleotide hybridizing to an mRNA encoding MHC I/HLA I hybridizes to a target sequence within exon 4.

In another embodiment, the second oligonucleotide hybridizing to an mRNA encoding MHC I/HLA I hybridizes to a target sequence within exon 3.

In another embodiment, the first group of oligonucleotides comprises at least one oligonucleotide comprising a nucleotide sequence selected from the group consisting of:

(a) (5'-CATCAGAATCCTTACTTTGTGACAC-3'), SEQ ID NO: 7

(b) (5'-CACGTGGTCGGGGWAGAAGC-3'), SEQ ID NO: 6

(c) (5'-CTCAGRGTGRCYTCATGGTCAGAG-3'), SEQ ID NO: 8

(d) (5'-AAGCAGTGGTATCAACGCAGAGTACGCGGG-3'), SEQ ID NO: 5

(e) (5'-AAGCAGTGGTATCAACGCAGAGTACATGGG-3'), SEQ ID NO: 41

(f) (5'-GTGTCCTGRGTYTGGTCCTC-3'). SEQ ID NO: 29

In another embodiment, the second group of oligonucleotides comprises at least one oligonucleotide comprising a nucleotide sequence selected from the group consisting of:

(a) (5' AAGCAGTGGTATCAACGCAGAGT 3'), SEQ ID NO: 10

(b) (5' TTAGAGTCTCTCAGCTGGTACACGGCAG 3'), SEQ ID NO: 12

(c) (5' GGCTCAAACACAGCGACCTCGGGTG 3'), SEQ ID NO: 11

(d) (5' CTGCGGAGCSMSTCCACGCAC 3'), SEQ ID NO: 13

(e) (5' GCTCYCAYTCCATGARGTATTTC 3'), SEQ ID NO: 23

(f) (5' AAGCAGTGGTATCAACGCAGAGTAC 3'), SEQ ID NO: 30

(g) (5' TGGCCCTGACCSAGACCTGGGC 3'), SEQ ID NO: 31

(h) (5' GTGGGCTACGTGGACGRCAC 3'), SEQ ID NO: 32

-continued (i) (5' GGTCAGTGTGATCTCCGCAGGGTAG 3'), SEQ ID NO: 33

(j) (5' TCCTTCCCGTTCTYCAGGTRTCTGCG3'), SEQ ID NO: 34

(k) (5' TCCTTCCCRTTCTYCAGGTRTCTGCG 3') SEQ ID NO: 35

(l) (5'-CTCAGRGTGRCYTCATGGTCAGAG-3') SEQ ID NO: 8

(m) (5'-CTGCGGAGCSMSTCCACGCAC-3') SEQ ID NO: 20
and (n) (5'-GTGTCCTGRGTYTGGTCCTC-3'). SEQ ID NO: 29

In another embodiment, the third group of oligonucleotides comprises at least one oligonucleotide comprising a nucleotide sequence selected from the group consisting of:

(a) (5' NNNNNAAGCAGTGGTATCAACGCAGAGT 3'), SEQ ID NO: 16

(b) (5' GTACACGGCAGGGTCAGGGTTC 3'), SEQ ID NO: 19

(c) (5' CGGGTGGGAACACCTTGTTCAGGT 3'), SEQ ID NO: 17

(d) (5' CGGGTGGGAACACGTTTTTCAGGT 3'), SEQ ID NO: 18

(e) (5' GCTCYCAYTCCATGARGTATTTC 3'), SEQ ID NO: 23

(f) (5' CTGCGGAGCSMSTCCACGCAC 3'), SEQ ID NO: 20

(g) (5' GTGGGCTACGTGGACGRCAC 3'), SEQ ID NO: 32

(h) (5' GGTCAGTGTGATCTCCGCAGGGTAG 3'), SEQ ID NO: 33

(i) (5' TCCTTCCCGTTCTYCAGGTRTCTGCG 3'), SEQ ID NO: 34

(j) (5' TCCTTCCCRTTCTYCAGGTRTCTGCG 3'), SEQ ID NO: 35

(k) (5' NNNNNAAGCAGTGGTATCAACGCAGAGTAC 3'), SEQ ID NO: 36

(l) (5' GGTGGGAACACCTTGTTCAGGTCC 3'), SEQ ID NO: 37

(m) (5' GGGTGGGAACACGTTTTTCAGGTCC 3'), SEQ ID NO: 38
and (n) (5' TGGTACACGGCAGGGTCAGGGTTC 3'). SEQ ID NO: 39

In another aspect, the present invention relates to a method of treating a patient by adoptive T cell therapy, comprising a T cell which has been identified by a any methods described herein.

Other features and advantages of the instant invention will be apparent from the following detailed description and claims.

BRIEF DESCRIPTION OF THE DRAWINGS

FIG. 11A shows the frequency of reads related to the HLA alleles of the patient. FIG. 11B shows a list of HLA-C subtypes summarized under C*# group that a patient may express on one of their alleles.

FIG. 12A, FIG. 12B, and FIG. 12C show quantitative measurement of HLA IVT mRNA at differing amount of HLA-B0702. FIG. 12A shows the molar ratios of IVT mRNA encoding the different HLA molecules in the sample. FIG. 12B shows the ratio of the number of HLA-B0702 sequence reads related to the number of total annotated HLA reads (y-axis) with regard to the molar ratio of HLA-B0702 RNA to total HLA RNA (x-axis). FIG. 12C shows the ratio of the number of defined HLA sequence reads related to the number of sequence reads of total annotated HLA reads (y-axis) with regard to the molar ratio of the defined HLA-B0702 RNA to total HLA RNA (x-axis).

FIG. 13A, FIG. 13B, and FIG. 13C show quantitative measurement of HLA IVT mRNA at differing amount of HLA-A0201. FIG. 13A shows the molar ratios of IVT mRNA encoding the different HLA molecules in the sample. FIG. 13B shows the ratio of the number of HLA-A0201 sequence reads related to the number of sequence reads of total annotated HLA reads (y-axis) with regard to the molar ratio of HLA-A0201 RNA to total HLA RNA (x-axis). FIG. 13C shows the ratio of the number of defined HLA sequence reads related to the number of sequence reads of total annotated HLA reads (y-axis) with regard to the molar ratio of the defined HLA-A0201 RNA to total HLA RNA (x-axis).

FIG. 14A, FIG. 14B, and FIG. 14C show quantitative measurement of HLA IVT mRNA at differing amount of HLA-C1203. FIG. 14A shows the molar ratios of IVT mRNA encoding the different HLA molecules in the sample. FIG. 14B shows the ratio of the number of HLA-C1203 sequence reads related to the number of sequence reads of total annotated HLA reads (y-axis) with regard to the molar ratio of HLA-C1203 RNA to total HLA RNA (x-axis). FIG. 14C shows the ratio of the number of defined HLA sequence reads related to the number of sequence reads of total annotated HLA reads (y-axis) with regard to the molar ratio of the defined HLA-C1203 RNA to total HLA RNA (x-axis).

FIG. 15A shows the fraction of K562 cell expression HLA-A*0201 in relation to the amounts of transfected mRNA analyzed by FACS measurement. FIG. 15B shows the analysis of the same samples by the method of invention, wherein the readout is the ratio of HLA-A*0201 specific sequence reads to all annotated HLA reads.

FIG. 16A shows the fraction of CMV-pp65-495-503 (NLV) epitope specific CD8 T cells compared to all CD8 positive T cells in relation to the amounts of mRNA transfected to the co-cultured K562 cells measured by FACS analysis. FIG. 16B and FIG. 16C show relative frequency of reads relating to one exemplary alpha and beta TCR sequence, respectively. The x-axis shows T cell samples obtained from co-cultivation with K562 cells transfected with 0, 0.05, 0.1, 0.5, 2 μg loaded with CMV-pp65-495-503 (NLV) peptide antigen (samples 1 to 5) and loaded with a control peptide (samples 6 to 10).

FIG. 17A demonstrates the release of IFN-γ of antigen specific T cell in dependence of the HLA expression of the co-cultured antigen presenting K562 cell in an ELISPOT assay in triplicates. T cells are obtained from a CMV responsive individual. The left row of triplicates shows samples where K562 cell have been loaded with CMV-pp65-495-503 antigen, while the right row shows samples where K562 cell have been loaded with a control antigen. Lanes one to five referred to the K562 cells transfected with increasing amount of HLA-A*0201 presenting the CMV-pp65-495-503 epitope. FIG. 17B shows the fraction of viable cells compared to the whole cell population, when K562 are transfected with increasing amount of HLA-A*0201, loaded with CMV epitope antigen, and co-cultured with CD8 T cells from a CMV responsive individual.

DETAILED DESCRIPTION OF THE INVENTION

Figure 1:
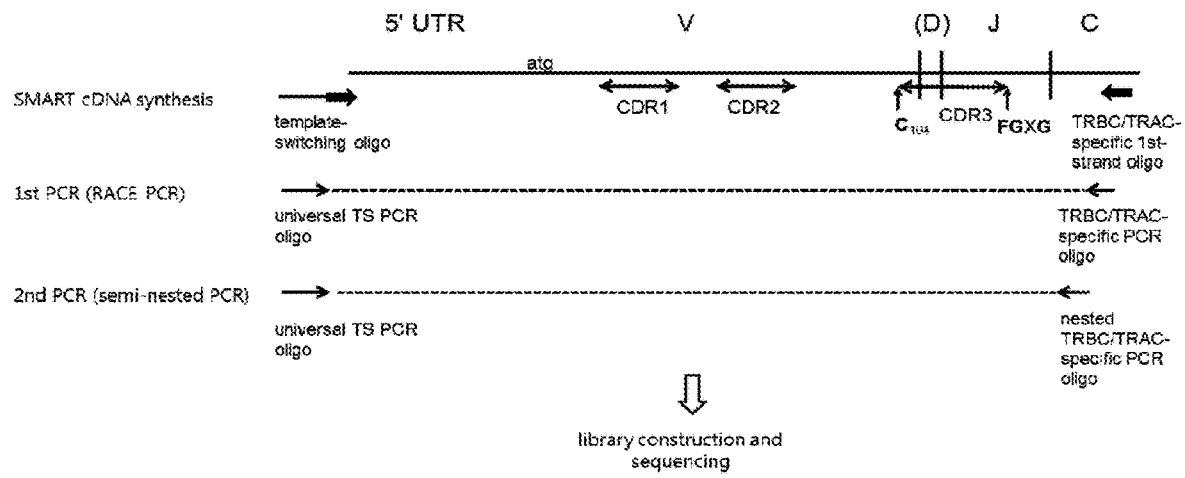
FIG. 1 shows a schematic overview of the strategy for profiling of mRNAs encoding T cell receptor chains expressed in a sample.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments described throughout the specification should not be construed to limit the present invention to only the explicitly described embodiments. This description should be understood to support and encompass embodiments which combine the explicitly described embodiments with any number of the disclosed and/or preferred elements. Furthermore, any permutations and combinations of all elements described herein should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland. However, definitions and explanations used herein prevail.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In order that the present invention may be more readily understood, certain terms are first defined. Additional definitions are set forth throughout the detailed description.

The terms "subject", "individual", "organism" or "patient" are used interchangeably and relate to vertebrates, preferably mammals including human and non-human mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. The term "animal" as used herein also includes humans. The term "subject" may also include a patient, i.e., an animal, preferably a human having a disease or condition, preferably a disease or condition as described herein or suspected of having a disease or condition. Alternatively, the subject may be free of a disease or may be a subject who is vaccinated.

The term "immune response" refers to an integrated bodily response to an antigen and preferably refers to a cellular immune response or a cellular as well as a humoral immune response. The immune response may be protective, preventive, prophylactic and/or therapeutic. A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either 'helpers' or 'killers'. The helper T cells (also termed $CD4^+$ T cells) play a central role by regulating the immune response and the killer cells (also termed cytotoxic T cells, cytolytic T cells, $CD8^+$ T cells or CTLs) kill diseased cells such as infected cells or malignant cells, preventing the production of more diseased cells.

An "antigen" as used herein is preferably a polypeptide or peptide, which corresponds to a naturally occurring antigen or is derived therefrom by proteolytic processing. Such naturally occurring antigens may include or may be derived from allergens, viruses, bacteria, fungi, parasites and other infectious agents and pathogens or an antigen may also be a tumor-associated antigen. The term "antigen" as used herein comprises an epitope against which an immune response is generated or against which an immune response is suspected to be generated. Preferably, an antigen in the context of the present invention is a molecule which, optionally after processing and/or presentation, induces an immune reaction or immune response, which is preferably specific for the antigen. In a preferred embodiment, the term "antigen" corresponds to a peptide, which is either a naturally occurring peptide or which has been derived from a larger entity by proteolytic cleavage and which is or can be presented by an MHC I or MHC II molecule, preferably by an HLA I or HLA II molecule including HLA-A, HLA-B and HLA-C or HLA-DP, HLA-DQ, and HLA-DR. A peptide or peptidic fragment of an antigen presented by an MHC I molecule preferably comprises between 5 and 14 amino acid residues, i.e. the peptide may have a length of 5, 6, 7, 8, 9, 10, 11, 12, 13 or 14 amino acids. A peptide presented by an MHC II molecule preferably comprises between 5 and 50 amino acid residues, particularly between 9 and 25 amino acid residues, i.e. the peptide may have a length of 9, 10, 11, 12, 13, 14, 15, 16, 17, 18, 19, 20, 21, 22, 23, 24, or 25 amino acids.

The term "MHC", as used herein refers to MHC I and MHC II and encompasses HLA I and HLA II including HLA-A, HLA-B and HLA-C as well as HLA-DP, HLA-DQ, and HLA-DR. The term "MHC I", as used herein refers to MHC I and encompasses HLA I including HLA-A, HLA-B and HLA-C. The term MHC II refers to MHC II and encompasses HLA II including HLA-DP, HLA-DQ, and HLA-DR. Likewise, as used herein the term "HLA" refers to HLA I and HLA II including HLA-A, HLA-B and HLA-C as well as HLA-DP, HLA-DQ, and HLA-DR. Furthermore, the term "HLA I" encompasses HLA-A, HLA-B and HLA-C. The term "HLA II" encompasses HLA-DP, HLA-DQ, and HLA-DR. Preferably HLA I relates to HLA-A, HLA-B and HLA-C and HLA II relates to HLA-DP, HLA-DQ, and HLA-DR.

Any embodiment described herein with respect to HLA alleles or isotypes, i.e. with respect to a human MHC may also be carried out with respect to any non-human MHC. Thus, even embodiments only referring to HLA, HLA I or HLA II are to be understood as disclosing an embodiment relating to non-human MHC, i.e. non-human MHC I or MHC II. The present teaching is in no way limited to human application.

The term "MHC/HLA" means MHC, preferably HLA. The term "MHC I/HLA I" means MHC I, preferably HLA I. The term "MHC II/HLA II" means MHC II, preferably HLA II.

In a preferred embodiment, an antigen is a tumor-associated antigen, i.e. a constituent of a transformed or malignant cell which may, for example, be derived from the cytoplasm, the cell surface and the cell nucleus, in particular from those antigens which are produced, preferably in large quantity, intracellular or as surface antigens of malignant cells. In particular, the antigen or peptides derived from a tumor-associated antigen should be recognizable by a T cell receptor. Preferably, the tumor-associated antigen is only expressed in the malignant cell after transformation of said cell into a malignant or tumorigenic state. Preferably, the antigen or peptide if recognized by a T cell receptor is able to induce in the presence of appropriate co-stimulatory signals, clonal expansion of the T cell carrying the T cell receptor specifically recognizing the antigen or peptide. In the context of the embodiments of the present invention, the antigen is preferably presented by a cell, preferably by an antigen presenting cell and/or a diseased cell, in the context of MHC/HLA molecules, which results in an immune reaction against the antigen.

Typically, the identity and amount of the various different mRNAs encoding the various MHC/HLA isotypes expressed in the sample of the subject are determined. Typically, the method of the present invention comprises a first step of determining the amount or concentration of mRNA present in the sample and a second step of determining the nucleotide sequence of the mRNA. Preferably, the mRNA amount or concentration or the level of gene expression and the nucleotide sequence of the mRNA is determined in one step by next-generation sequencing. The mRNA amount or concentration or the level of gene expression is preferably determined based on the number of respective MHC/HLA isotype specific sequence reads detected during next generation sequencing (Ruan & Ruan, Methods Mol Biol. (2012), 809: 535-62). In an alternative method, the nucleotide sequence of mRNA can be determined by sequencing cDNA by classical Sanger-Sequencing. A determination of the mRNA amount or concentration or the level of gene expression can be done by quantitative RT-PCR using amplification primer specific for the respective MHC/HLA isotype identified by previous sequencing.

"Establishing gene expression profiles" in more general terms means obtaining information on the identity and the amount, concentration or expression level of a plurality of different mRNAs encoding the MHC/HLA isotypes expressed in the sample of the subject and of a plurality of mRNAs encoding the T cells receptor chains expressed in the sample of the subject.

In addition, the step of establishing gene expression profiles also comprises determining the identity and amount of a plurality of different mRNAs present in the sample of the subject, encoding the various different T cell receptor chains. Combining qualitative information with quantitative information allows drawing a conclusion on the presence or absence and, in particular, on the level of expression of specific MHC/HLA isotypes and specific T cell receptor chains. Qualitative information about the identity of an mRNA can be obtained for example by determining its complete nucleotide sequence or by determining a partial nucleotide sequence comprised by said mRNA. The nucleotide sequence may be determined on the RNA level, preferably it is however determined after reverse transcription of the mRNA into DNA or after amplification of said DNA. Preferably, said partial nucleotide sequence is characteristic for said particular mRNA and, thus, the encoded protein and allows distinguishing said mRNA from any other mRNA. The term "quantifying" or obtaining "quantitative information" in the context of the present invention includes obtaining information about the amount of a particular mRNA present in the sample, wherein the term "amount" includes relative amounts and absolute amounts. Preferably, the qualitative and/or quantitative information is obtained by next generation sequencing.

In a first aspect, identifying mRNAs comprises obtaining nucleotide sequence information, which allows distinguishing between the different mRNAs encoding the various isotypes transcribed from MHC I alleles and from MHC II alleles, particularly the different isotypes of HLA I including HLA-A, HLA-B and HLA-C and the various isotypes of HLA II including HLA-DP, HLA-DQ, and HLA-DR. Preferably, HLA I is encoded by a nucleotide sequence consisting of or comprising the nucleotide sequence as shown in SEQ ID NO: 1. Preferably, said mRNA encoding HLA II is an mRNA encoding the β-chain of HLA II. Preferably, the β-chain of HLA-DR is encoded by a nucleotide sequence consisting of or comprising the nucleotide sequence as shown in SEQ ID NO: 26 or SEQ ID NO: 27. Preferably, the β-chain of HLA-DQ is encoded by a nucleotide sequence consisting of or comprising the nucleotide sequence as shown in SEQ ID NO: 28.

By obtaining this nucleotide sequence information and by quantifying the amount of the different mRNAs identified, it is possible to conclude on the capability of the cells in the sample to present a specific antigen to the patient's immune system. Preferably, identifying the nucleotide sequence information comprises obtaining the nucleotide sequence of mRNA transcribed from or encoded by exon 2 and/or exon 3 of MHC MLA I is determined and/or it comprises obtaining the complete nucleotide sequence transcribed from or encoded by exon 2 of MHC II/HLA II. Alternatively, the nucleotide sequence information may only comprise a partial nucleotide sequence of the aforementioned nucleotide sequences, wherein the partial sequence includes highly polymorphic regions comprising characteristic nucleotide positions which allow the discrimination of large numbers of isotypes transcribed from a locus of MHC I/HLA I or MHC II/HLA II. Preferably, the partial sequence comprises the nucleic acid bases 97-561 of SEG ID NO: 1 (consensus sequence of the HLA I coding ORF). According to the teaching of the present invention, the nucleotide sequence or partial nucleotide sequence of mRNA encoding isotypes of HLA-A, HLA-B and HLA-C is analyzed. However, it is also envisaged to limit the method of the present invention to the analysis of mRNA encoding HLA-A and HLA-B or HLA-A and HLA-C or HLA-B and HLA-C. The same analysis may be carried out in a sample obtained from a non-human animal by analyzing mRNA transcribed from corresponding loci.

In a second aspect, identifying mRNA encoding T cell receptor chains comprises obtaining nucleotide sequence information, which allows distinguishing between mRNAs encoding different T cell receptor chains, i.e. TCR α-chains and TCR β-chains assembled into T cell receptors with different receptor specificities. The T cell receptor chains transcribed from recombined T cell receptor loci essentially differ in the complementary determining regions CDR1, CDR2 and CDR3 of the TCR α-chains and TCR β-chains. Thus, preferably the complete nucleotide sequence comprising the nucleotide sequences encoding the CDR1, CDR2 and CDR3 of the alpha chain and/or the beta chain is determined. However, the mRNAs present in the sample may also be identified by determining a partial nucleotide sequence of the mRNA encoding the α-chain or β-chain, wherein said partial nucleotide sequence comprises a nucleotide sequence encoding the CDR1 and the CDR2 or said partial nucleotide sequence comprises a nucleotide sequence encoding the CDR2 and CDR3.

The term "T cell receptor" as used herein refers to a receptor comprising an alpha chain (or TCR α-chain (TCRA)) and a beta chain (or TCR β-chain (TCRB)). The term "T cell receptor chains transcribed from recombined T cell receptor loci" as used herein relates to T cell receptor chains which are transcribed from a T cell receptor gene, which has been rearranged to comprise one V, one D (only β- and δ-chain), one J and one C region. The term "constant region" or "C region", as used herein, refers to the $C_\alpha$ and to $C_{\beta1}$ and $C_{\beta2}$. Moreover, it is well established in the art that the rearranged TCR gene further comprises imprecise V-(D)-J rearrangements wherein random nucleotides are introduced and/or deleted at the recombination sites. Since the rearrangement of the TCR gene loci occur in the genome during maturation of T cells, nearly all mature T cells only express one specific α/β TCR or γ/δ TCR.

The term "sample" as used herein refers to a biological sample obtained from a subject. The term "sample" also comprises samples which, after they have been obtained from the subject, have been subjected to conditions of in vitro cultivation.

In a preferred embodiment of the methods of the present invention, the subject or the cultivated sample is exposed to an antigen of interest in order to activate immune cells specific to the antigen of interest. Said immune cells include T cells expressing a T cell receptor, which is specific for the antigen of interest. In a preferred embodiment, said antigen may be, for example, an antigen used for vaccination of the subject. Alternatively, the antigen is a tumor-associated antigen expressed in the tissue from which the sample has been obtained or the antigen is a peptidic fragment of said antigen. In another embodiment of the invention the exposure to said antigen of interest may be repeated, e.g. to increase the immune response. The sample may be from a tissue or organ which is affected from a disease or which is free of a disease. The sample may be obtained from cancerous tissue or corresponding normal tissue, i.e. healthy tissue of the same type of tissue which is not affected from the cancer. The term "cancerous tissue" and the term "disease" as used herein relates to cancers or tumors such as leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Typically, the "first sample" as used herein is a reference sample. The first sample can be a reference sample, which has been obtained from a subject prior to the "second sample". Alternatively, the first sample is a sample obtained from a subject prior to vaccination or a sample obtained from a cancer patient prior to or during cancer therapy or obtained from a subject before the cancer has developed. Also encompassed by the term "first sample" is a reference sample obtained from a different subject than the subject from which the second sample is obtained. In one embodiment, the first sample is obtained from a subject, who has been exposed to the antigen. Preferably, however, the first sample has been obtained from a subject, who has not been exposed to the antigen or who has been exposed to the antigen after the sample has been obtained.

In one embodiment, the first sample is characterized by comprising T cells. In another embodiment, the first sample is characterized by comprising a reduced amount or concentration of antigen compared to the second sample. Preferably, the first sample is characterized by comprising T cells and a reduced amount or concentration of antigen compared to the second sample.

Typically, the "second sample" is a sample obtained from a subject after the subject has been exposed to an antigen or to a peptidic fragment of an antigen. Said antigen may be, for example, an antigen used for vaccination of the subject. Alternatively, the antigen is a tumor-associated antigen expressed in the tissue from which the second sample has been obtained or the antigen is a peptidic fragment of said antigen.

In one embodiment, the second sample is characterized by comprising T cells. In another embodiment, the second sample is characterized by or suspected of being characterized by comprising antigen presenting cells presenting said antigen. In another embodiment, the second sample is characterized by or suspected of being characterized by comprising an elevated amount or concentration of said antigen or the peptidic fragment thereof compared to the first sample. Preferably, the second sample is characterized by or suspected of being characterized by comprising T cells, antigen presenting cells presenting said antigen, and an elevated amount or concentration of said antigen compared to the first sample.

The terms "T cell" and "T lymphocyte" are used interchangeably herein and include T helper cells (CD4+ T cells) and cytotoxic T cells (CTLs, CD8+ T cells) which comprise cytolytic T cells. Preferably the T cells are cells with recombined T cell receptor loci, in particular T cells encoding TCR α-chain and TCR β-chain. The presence of T cells in the sample can be tested by flow cytometry using antibodies directed against T cell specific markers (e.g. CD3, or CD4 and CD8) or immunohistochemistry (e.g. Whiteland et al., J Histochem Cytochem. 1995, 43: 313-20). Alternatively the presence of T cells is demonstrated by the identification of recombined T cell receptors according to the method presented herein. Generally testing for the presence of T cells is not required, because the origin of the sample ensures the presence of T cells.

The term "elevated amount of antigen compared to the first sample" means that the amount of antigen in the second sample is larger than the amount of antigen in the first sample. A sample is characterized by comprising T cells, antigen presenting cells presenting said antigen and an elevated amount of antigen, if the sample has been tested for the presence of T cells and antigen presenting cells and if the amount of antigen in the first and the second sample has been determined.

The term "antigen presenting cell presenting said antigen" refers to a cell which is characterized by a surface exposed MHC/HLA molecule which is loaded with an antigen or peptide. Preferably, said MHC/HLA is MHC I/HLA I and the cell is a diseased cell such as a virus-infected cell or a malignant or tumorigenic cell. Also encompassed are professional antigen presenting cells such as dendritic cells. The presence of antigen presenting cells in the sample as well as the amount of antigen may be determined for example by the use of monoclonal antibodies directed to the antigen peptide-MHC complex in flow cytometry (see e.g. Porgador et al., Immunity 1997, 6:715-726).

A sample is suspected of being characterized by comprising T cells, antigen presenting cells presenting said antigen and an elevated amount of antigen, if the sample has not been tested accordingly.

According to the method of the present invention, the second sample is compared to the first sample, wherein a deviation of the expression profiles between the first and the second sample indicates that the subject has responded to an antigen.

A "deviation" is observed if the amount or concentration of an mRNA encoding a particular TCR α-chain and/or a particular TCR β-chain or a particular MHC/HLA isotype in the second sample is decreased or increased with in comparison to the first sample, wherein the increase or decrease is by at least 10%, 20%, or 30%, preferably by at least 40% or 50%, or even more.

According to the teaching of the present invention, various conclusions can be drawn from the comparison of the expression profiles established by the method of the invention.

In one embodiment, the method of the present invention comprises concluding from the comparison of the expression profiles whether the subject's immune system has responded to the antigen and which individual T cell receptor, or which specific TCR α-chain and TCR β-chain, and which MHC/HLA isotype or which group of all potential MHC/HLA isotypes is involved or is potentially involved in the immune response of the subject against said antigen.

The term "concluding from the comparison of the expression profiles whether the subject's immune system has responded to the antigen" means concluding from the observation of identical or deviating amounts or concentration of mRNAs encoding MHC/HLA isotypes and mRNAs encoding TCR α-chains and/or TCR β-chains, whether the immune system reacted to the antigen with an immune response, preferably a cellular immune response.

In one embodiment, the comparison of expression profiles allows the conclusion that the subject has responded to the antigen, wherein an individual T cell receptor comprising a specific TCR α-chain and a specific TCR β-chain and a specific MHC/HLA isotype is identified as being involved in the subject's immune response against the antigen. Preferably a T cell receptor and an MHC/HLA isotype are involved in an immune response, if a T cell expressing said T cell receptor comprising said specific TCR α-chain and said TCR β-chain binds to a cell presenting the antigen through said MHC/HLA isotype and, upon binding, the T cell releases cytotoxins such as perforin, granzymes, and/or granulysin or if, upon binding, killing of the cell presenting the antigen is induced. Accordingly, tests for assessing the involvement of a T cell expressing a specific T cell receptor and a cell presenting an antigen through a specific MHC/HLA isotype rely, for example, on measuring the release of one or more of said cytotoxins and/or signals of the cell presenting the antigen. Cytotoxin release can be measured for example by a Luciferase cytotoxicity assay, wherein a T cell expressing a specific combination of T cell receptor chains is brought into contact with luciferase transfected targets cells bearing the respective antigen loaded on the respective HLA, wherein the lysis of the target cell due to cytotoxin release of the T cell can be measured as a decrease of luminescence. Alternatively the release of Interferon-γ as signal of T cell activation can be determined e.g. by ELISPOT (Enzyme-Linked ImmunoSPOT) assay (WO2012038055, pages 83 and 84).

Preferably, amongst the identified mRNAs encoding MHC/HLA isotypes, the specific MHC/HLA isotype identified as being involved in the immune response of the subject against said antigen is the only MHC/HLA isotype expressed in the sample, which is capable of presenting the antigen under investigation. Preferably said MHC/HLA is MHC I/HLA I, i.e. for example HLA-A, HLA-B or HLA-C.

According to the teaching of the present invention, an MHC/HLA isotype is capable of presenting an antigen, if the peptide binding motif of the isotype allows binding of the antigen or of a peptidic fragment of the antigen arising from proteolytic processing of the antigen. Preferably, the capability of an MHC/HLA isotype of binding to an antigen is determined by concluding from the peptide binding motif of the isotype on the ability of said MHC/HLA isotype to bind to the antigen or to the peptidic fragment. Alternatively, the capability of an MHC/HLA isotype to bind to an antigen or peptidic fragment is determined in vitro, for example by mass spectrometric analysis of peptides eluted from specific MHC/HLA isotypes (Hunt et al., Science 1992, 255: 1261-1263).

Preferably the individual T cell receptor identified, i.e. the receptor comprised of a specific TCR α-chain and a specific TCR β-chain is identified by the detection of an increased amount of mRNA encoding said chains. Preferably, amongst the identified mRNAs encoding TCR α-chains and TCR β-chains, said mRNAs encoding the individual T cell receptor chains, i.e. the specific TCR α-chain and the specific TCR β-chain identified as being involved in the immune response of the subject against said antigen is the most abundant mRNA in the sample encoding a TCR α-chain and a TCR β-chain, respectively. Preferably the T cell receptor comprising the specific TCR α-chain and the specific TCR β-chain is known to be capable of binding to said specific MHC/HLA isotype identified or the expression of said chains is correlated with exposure of the patient to the antigen.

In another embodiment, the comparison of expression profiles allows the conclusion that the subject has responded to the antigen, wherein an individual T cell receptor and a group of potential MHC/HLA isotypes is identified. The term "group of potential MHC/HLA isotypes" refers to two or more MHC/HLA isotypes identified by the method of the present invention, which are capable of presenting the antigen. Preferably, the group of potential MHC/HLA isotypes comprises up to 2, up to 3, up to 4, up to 5 or up to 6 MHC I/HLA I or MHC II/HLA II isotypes. Alternatively, the group of potential MHC/HLA isotypes may comprise at least 2, at least 3, at least 4, at least 5 or at least 6 MHC I/HLA I isotypes or MHC II/HLA II isotypes.

In some cases, the method of the present invention may identify more than one MHC/HLA isotype that is capable of binding to the antigen under investigation. In these cases, an additional step of selecting from the group of potential MHC/HLA isotypes at least one MHC/HLA isotype which mediates the immune response with the identified T cell receptor. Preferably, the said MHC/HLA isotype is selected by a luciferase cytotoxicity assay or by ELISPOT (Enzyme-Linked ImmunoSPOT) (WO2012038055A1, pages 83-84).

In one embodiment, the observation of a decreased or reduced amount or concentration of at least one (type of) mRNA encoding a specific MHC/HLA isotype and/or the absence of an increased amount or concentration of at least one (type of) mRNA encoding a specific TCR α-chain and of at least one (type of) mRNA encoding a specific TCR β-chain are indicative of a suppression of the immune response against said antigen. Preferably, the T cell receptor assembled by said TCR α-chain and said TCR β-chain is a T cell receptor known to be capable of binding to a peptide or antigen presented by said MHC/HLA isotype.

The observation of a decreased or reduced amount or concentration of mRNA encoding a specific MHC/HLA isotype means that the expression of the specific MHC/HLA isotype is down-regulated or repressed. The observation of a decreased or reduced amount or concentration of at least one mRNA encoding an MHC/HLA isotype and/or the absence of an increased amount or concentration of at least one mRNA encoding a TCR α-chain and of at least one mRNA encoding a TCR β-chain means that the subject has not responded or is not capable of inducing an immune against the antigen. Preferably, said T cell receptor is a T cell receptor known to be capable of binding to said antigen when presented by said MHC/HLA isotype.

"Suppression of the immune response against said antigen" means that the subject's immune system does not respond or react to the antigen. In a preferred embodiment, the immune response is a cellular immune response. The term a "cellular immune response", a "cellular response", a "cellular response against an antigen" or a similar term is meant to include a cellular response directed to cells characterized by presentation of an antigen with class I or class II MHC/HLA. The cellular response relates to T cells or T-lymphocytes which act as either 'helpers' or 'killers'. The helper T cells (also termed CD4$^+$ T cells) play a central role by regulating the immune response and the killer cells (also termed cytotoxic T cells, cytolytic T cells, CD8⁺ T cells or CTLs) kill diseased cells such as infected cells or malignant cells, preventing the production of more diseased cells. The capability to induce an immune response can be verified, for example by a luciferase cytotoxicity assay or by ELISPOT (Enzyme-Linked ImmunoSPOT assay (WO2012038055A1, pages 83-84).

This embodiment also relates to the observation that some virus-infected cells or some transformed cells evade immune surveillance by down-regulation of expression of MHC/HLA class I and II molecules. The down-regulation may affect a single MHC/HLA isotype or multiple MHC/HLA isotypes. For example, it has been shown that gene expression of HLA-A11 is down-regulated in EBV-infected cells of HLA-A11-positive patients. The immune system of these patients fails to induce an HLA-A11 restricted CTL response against EBV infected cells (Masucci et al., Cell Immunol. 1989, 120: 396-400). The down-regulation of expression of HLA-A11 prevents that the corresponding HLA-restricted viral antigens are presented to the immune system. Since the HLA-restricted presentation is required for triggering activation and clonal expansion of T cells, typically a corresponding increase in the amount of mRNAs encoding a T cell receptor (i.e. an increase of mRNA encoding a specific TCR α-chain and of mRNA encoding a specific TCR β-chain) specific for the complex of the antigen and the down-regulated HLA isotype cannot be detected.

In another embodiment, the observation of (1) mRNA encoding at least one MHC/HLA isotype, preferably known to be capable of presenting the antigen and of (2) an increased amount or concentration of at least one species of mRNA encoding a specific TCR α-chain and of at least one species of mRNA encoding a specific TCR β-chain, which chains assemble into a T cell receptor, preferably known to bind to the antigen when presented by an MHC/HLA molecule or the expression of which is correlated with exposure of the patient to the antigen, indicate that the patient's immune system has responded to the antigen.

In another embodiment, establishing the gene expression profile comprises: (i) reverse transcription of mRNA with a reverse primer hybridizing to a target sequence within a nucleotide sequence transcribed from a conserved region of exon 3 or exon 4 of an MHC/HLA allele and generating a first cDNA strand with a 3' poly (C) sequence comprising at least 3 C nucleotides at the 3' end of said first cDNA strand, which poly (C) sequence serves as a target sequence for a template switching oligonucleotide, wherein said template switching oligonucleotide comprises at least 3 G nucleotides and serves as a matrix for the elongation of the first cDNA strand at the 3' end of said poly (C) sequence and introduces a primer binding site at the 3' end of said first cDNA strand, and (ii) reproducing the cDNA by polymerase chain reaction, with a forward primer which is capable of hybridizing to said primer binding site. The term "matrix" as used herein means template.

The term "first cDNA strand" as used throughout the present specification refers to the DNA strand synthesized by reverse transcription, i.e. the DNA strand generated by using mRNA as a template.

In another embodiment, establishing the gene expression profile comprises: (i) reverse transcription of mRNA encoding a TCRα chain and of mRNA encoding a TCRβ chain with a reverse primer hybridizing to a target sequence within a nucleotide sequence encoding the constant region of TCRα and TCRβ chains and generating a first cDNA strand with a 3' poly (C) sequence comprising at least 3 C nucleotides at the 3' end of said cDNA strand, which poly (C) sequence serves as a target sequence for a template switching oligonucleotide, wherein said template switching oligonucleotide comprises at least 3 G nucleotides and serves as a matrix for the elongation of the first cDNA strand at the 3' end of said poly (C) sequence and introduces a primer binding site at the 3' end of said first cDNA strand, and (ii) reproducing the cDNA by polymerase chain reaction, with a forward primer which is capable of hybridizing to said primer binding site.

"Reverse transcription of mRNA" means transcribing an mRNA strand into a complementary DNA strand (the "first cDNA") and, optionally, a strand of DNA complementary to said first cDNA strand. Reverse transcription with a reverse primer hybridizing to a target sequence within a nucleotide sequence transcribed from a conserved region of exon 3 or exon 4 of an MHC/HLA allele will generate a first cDNA strand which is complementary to the mRNA encoding the MHC/HLA isotype, wherein the 5' end of said first cDNA strand is formed by the reverse primer. The "conserved region of exon 3 or exon 4" as used herein is a nucleotide sequence transcribed from or encoded by exon 3 or exon 4 of an HLA allele, preferably of HLA I, which shows at least 60%, 70%, 80%, 90%, 95%, 99% nucleotide sequence identity between each known MHC I/HLA I allele or at least 60%, 70%, 80%, 90%, 95%, 99% nucleotide sequence identity between each known MHC II/HLA II allele. Preferably, a conserved region according to the teaching of the present invention comprises or consists of 10, 15, 20, 25, 30, 35, 40, 45, or 50 nucleotides or up to or at least 10, 15, 20, 25, 30, 35, 40, 45, or 50 nucleotides.

Preferably the reverse primer used for reverse transcription, which hybridizes to the mRNA encoding the MHC/HLA isotype comprises or consists of 10, 15, 20, 25, 30, 35, 40, 45, or 50 nucleotides or up to or at least 10, 15, 20, 25, 30, 35, 40, 45, or 50 nucleotides. Preferably the reverse primer is an oligonucleotide which hybridizes to a target sequence within a nucleotide sequence transcribed from a conserved region of exon 3 or exon 4 of an MHC/HLA allele, preferably an HLA I allele. Preferably said reverse primer is capable of hybridizing to a target sequence which is located within exon 3 or exon 4, more preferably within exon 4. Preferably said HLA I is HLA-A, HLA-B and HLA-C. Preferably said reverse primer comprises or consists of a nucleotide sequence as shown in SEQ ID NO: 8 (5'-CTCAGRGTGRCYTCATGGTCAGAG-3') or in SEQ ID NO: 9 (5'-CAGCATCTTGYTCTGKGCAGATTC-3') or in SEQ ID NO: 29 (5'-GTGTCCTGRGTYTGGTCCTC-3').

Reverse transcription with a reverse primer hybridizing to a target sequence within a nucleotide sequence encoding the constant region of TCRα and TCRβ chains will generate a first cDNA strand which is complementary to the mRNA encoding TCRα chains and TCRβ chains, wherein the 5' end of said first cDNA strand is formed by the reverse primer. The term "constant region" of TCRα and TCRβ chains refers to the portion of TCR chains, which is proximal to the membrane comprising the portion of the TCRα chain, which is encoded by the nucleotide sequence of SEQ ID NO: 2 or the portion of the TCRβ1 chain, which is encoded by the nucleotide sequence of SEQ ID NO: 3, or the portion of the TCRβ2 chain, which is encoded by the nucleotide sequence of SEQ ID NO: 4.

Said "target sequence" may be any nucleotide sequence which comprises or consists of 10, 15, 20, 25, 30, 35, 40, 45, or 50 nucleotides or of up to or at least 10, 15, 20, 25, 30, 35, 40, 45, or 50 nucleotides and which shows at least 60%, 70%, 80%, 90%, 95%, 99% nucleotide sequence identity between each known nucleotide sequence encoding a TCRα chain or a TCRβ chain, respectively.

Preferably the reverse primer which hybridizes to the mRNA encoding the TCRα chains and TCRβ chains comprises or consists of 10, 15, 20, 25, 30, 35, 40, 45, or 50 nucleotides or up to or at least 10, 15, 20, 25, 30, 35, 40, 45, or 50 nucleotides. Preferably said reverse primer comprises or consists of a nucleotide sequence as shown in SEQ ID NO: 6 5'-CACGTGGTCGGGGWAGAAGC-3') or in SEQ ID NO: 7 5'-CATCAGAATCCTTACTTTGTGACAC-3') (the reverse primers of SMART cDNA synthesis described in the Examples) or to a nucleotide sequence as shown in SEQ ID NO: 11 (5'-GGCTCAAACACAGCGAC-CTCGGGTG-3') or in SEQ ID NO: 12 (5'-TTA-GAGTCTCTCAGCTGGTACACGGCAG-3') (the reverse primers of RACE-PCR described in the Examples) or to a nucleotide sequence as shown in SEQ ID NO: 17 (5'-CGGGTGGGAACACCTTGTTCAGGT-3'), in SEQ ID NO: 18 (5'-CGGGTGGGAACACGTTTTTCAGGT-3'), in SEQ ID NO: 19 (5'-GTACACGGCAGGGTCAGGGTTC-3') (the reverse primers of the Nested PCR described in the Examples), in SEQ ID NO: 37 (5'-GGTGGGAACACCTT-GTTCAGGTCC-3'), in SEQ ID NO: 38 (5'-GGGTGGGAACACGTTTTTCAGGTCC-3') or in SEQ ID NO: 39 (5'-TGGTACACGGCAGGGTCAGGGTTC-3').

As used herein, the degree of identity is given preferably for a nucleotide sequence which is at least about 80%, at least about 90% or about 100% of the entire length of the reference sequence. In preferred embodiments, the degree of identity is given for the entire length of the conserved region. The alignment for determining sequence identity can be done with tools known in the art, preferably using the best sequence alignment, for example, using Align, using standard settings, preferably EMBOSS: needle, Matrix: Blosum62, Gap Open 10.0, Gap Extend 0.5.

"Sequence identity" between two nucleotide sequences indicates the percentage of nucleotides that are identical between the sequences. The term "percentage identity" is intended to denote a percentage of nucleotides which are identical between the two sequences to be compared, obtained after the best alignment, this percentage being purely statistical and the differences between the two sequences being distributed randomly and over their entire length. Sequence comparisons between two nucleotide sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST N and TFASTA in Wisconsin Genetics Software Package, Genetics Computer Group, 575 Science Drive, Madison, Wis.). The percentage identity is calculated by determining the number of identical positions between the two sequences being compared, dividing this number by the number of positions compared and multiplying the result obtained by 100 so as to obtain the percentage identity between these two sequences.

A primer hybridizing or capable of hybridizing to a target sequence is an oligonucleotide, which is complementary to said target sequence. According to the invention, an oligonucleotide comprises at least or up to 6, in particular at least or up to 8, at least or up to 10, at least or up to 12, at least or up to 15, at least or up to 20, at least or up to 30 at least or up to 50 nucleotides. A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C. According to the invention, complementary nucleic acids hybridize over at least 40%, in particular at least 50%, at least 60%, at least 70%, at least 80%, at least 90% and preferably at least 95%, at least 98% or at least 99%, or 100% nucleotides.

Particularly preferred conditions of hybridization comprise hybridization at 65° C. in 200 nM primer, 150 mM $Na^+$, 2 mM $MgCl_2$ and pH 7.0.

Preferably, the step of reverse transcription makes use of a reverse transcriptase (RT) that has terminal transferase and template-switching activities (Matz et al. (1999); NAR 27:1558-1560). Preferably, said RT is an M-MLV RT (Moloney Murine Leukemia Virus Reverse Transcriptase. By making use of a reverse transcriptase with terminal transferase activity, the first cDNA strand generated can be modified at or near the 3' end with a nucleotide sequence of 3 or more C nucleotides (termed "poly(C)"), wherein a poly(C) sequence preferably comprises up to 3, 4, 5, 6, 7, 8, 9 or even more C nucleotides and wherein the poly (C) sequence is preferably a consecutive sequence of C nucleotides.

The terminal transferase activity adds primarily CTPs to the 3' end of the first cDNA strand, which then serves as the annealing site i.e. as target nucleotide sequence for a second oligonucleotide ("template switching oligonucleotide") that is capable of hybridizing i.e. base pairing with the C-rich region at the 3' end of the first cDNA strand, allowing the RT to then switch templates and continue replicating to the end of this oligonucleotide template formed by the template switching oligonucleotide. The result of the terminal transferase and template-switching activities is the addition of an oligonucleotide sequence to the 3' end of the first cDNA strand.

Preferably the template switching oligonucleotide (termed "TSO") of the present invention comprises, from 5' to 3', a nucleotide sequence which is complementary to a nucleotide sequence forming a primer binding site for a primer used in a subsequent PCR step of the method of the invention (the primer binding site is termed "PBS", the nucleotide sequence complementary to the PBS is termed "cPBS") and at least 3 consecutive G nucleotides (termed "poly(G)") and, optionally, a linker of up to 2, 3, 4, 5, 6, 7, 8, 9, 10, 11, 12, 13, 14, 15 or of up to 20 nucleotides between the cPBS and the poly(G). Preferably the least 3 consecutive G nucleotides are ribonucleotides (U.S. Pat. No. 5,962,271). The term "primer binding site" also refers to a nucleotide sequence at the 3' end of the first cDNA strand introduced by the template switching oligonucleotide. Preferably, the PBS and the corresponding cPBS comprises at least or up to 8, 9, 10, 11, 12, 13, 14, 15, 16, 17, 18, 19 or 20 nucleotides. Preferably the nucleotide sequence forming the PBS is unique with respect to the genetic information of the subject analysed, i.e. a sequence of consecutive nucleotides not present in the DNA or RNA of the subject. Preferably, the nucleotide sequence of the cPBS (and of oligonucloetide "TS-PCR") comprises the nucleotide sequence shown in SEQ ID NO: 10 (5'-AAGCAGTGGTATCAACGCAGAGT-3') or as shown in SEQ ID NO: 30 (5'-AAGCAGTGGTAT-CAACGCAGAGTAC-3') and the nucleotide sequence of the template switching oligonucleotide comprises the nucleotide sequence shown in SEQ ID NO: 5 (5'-AAGCA-GTGGTATCAACGCAGAGTACGCGGG-3') or in SEQ ID NO: 41 (5'-AAGCAGTGGTATCAACGCAGAGTA-CATGGG-3').

After completion of the first cDNA strand, the strand complementary to the first cDNA strand is generated by reproducing the cDNA in a polymerase chain reaction using a forward primer which is capable of hybridizing to the PBS. Preferably said forward primer which is capable of hybridizing to the PBS comprises at least 8, 9, 10, 11, 12, 13, 14, 15, 16, 17, 18, 19 or 20 nucleotides which are complementary to the primer binding site. Preferably, the nucleotide sequence of the forward primer comprises the nucleotide sequence shown in SEQ ID NO: 10 (5'-AAGCAGTGGTAT-CAACGCAGAGT-3) or as shown in SEQ ID NO: 30 (5'-AAGCAGTGGTATCAACGCAGAGTAC-3').

In other words, the method of the present invention comprises a step of reverse transcribing mRNA into a first cDNA strand which is essentially complementary to the mRNA encoding the TCR chains or the MHC/HLA isotypes, wherein the 3' end of said first cDNA strand comprises at least 3 C nucleotides followed by a PBS, which is located on said first cDNA strand in terminal position. Preferably, the method of the present invention furthermore comprises a step of synthesizing a DNA strand which is complementary to said first cDNA strand. Preferably, for synthesis of said DNA strand, a forward primer is used, which is capable of hybridizing to the PBS and which is complementary to the PBS. The method of the present invention may furthermore comprise one or more additional steps of PCR amplification. Preferably, these PCR amplifications are nested or semi nested PCR amplifications, i.e. PCR amplifications with nested forward and/or reverse primer.

A first PCR amplification may comprise or make use of a forward primer, which is complementary or capable of hybridizing to the PBS and a reverse primer, which comprises a sequence identical to the 5' end of the first cDNA strand.

Preferably, the target sequence of the forward primer of the first PCR is identical to PBS introduced by the TSO used for synthesizing the DNA strand, which is complementary to the first cDNA strand. Alternatively, the target sequence of the forward primer of the first PCR amplification may overlap with the PBS introduced by the TSO used for synthesizing said complementary strand by 1-20 nucleotides. Preferably, however, the target sequence of the forward primer of the first PCR amplification is separated from the PBS introduced by the TSO used for synthesizing the complementary strand of the first cDNA strand and is located 5' on the first cDNA strand. Preferably the sequences are separated by at least 1-100 nucleotides, preferably by 1-50 nucleotides. In a preferred embodiment, the forward primer of the first PCR amplification is an oligonucleotide capable of hybridizing to a nucleotide sequence which is complementary to the nucleotide sequence of the primer binding site provided by the template switching oligonucleotide. Preferably said forward primer is an oligonucleotide comprising the nucleotide sequence as shown in SEQ ID NO: 10 or as shown in SEQ ID NO: 30 (5'-AAGCAGTG-GTATCAACGCAGAGTAC-3'). In an alternative embodiment, the forward primer of the first PCR amplification is an oligonucleotide defined by the structural features described herein below for the forward primer of the second PCR amplification.

Preferably, the nucleotide sequence of the reverse primer of the first PCR amplification is identical to the nucleotide sequence of the primer used for reverse transcription of the mRNA into the first cDNA strand. Alternatively, the target sequence of the reverse primer of the first PCR amplification may overlap with the target sequence of said primer used for reverse transcription by 1-20 nucleotides. Preferably, however, the target sequence of the reverse primer is separated from the target sequence of the primer used for reverse transcription and comprises a sequence identical to the 5' end of the first cDNA strand. Preferably the target sequences are separated by at least 1-100 nucleotides, preferably by 1-50 nucleotides. In a preferred embodiment, the reverse primer of the first PCR amplification is an oligonucleotide of the kit of the present invention, wherein said oligonucleotide is selected from group (II) as defined herein below.

In one embodiment, the reverse primer of the first PCR amplification is an oligonucleotide capable of hybridizing to mRNAs encoding TCRα chains, wherein said oligonucleotide hybridizes to a target sequence within the nucleotide sequence encoding the constant region of the TCRα chain, wherein the target sequence either comprises the target sequence of the oligonucleotide used for reverse transcribing the mRNA into the first cDNA strand or is located 5' of said target sequence or overlaps with said target sequence. Preferably said reverse primer is an oligonucleotide comprising the nucleotide sequence as shown in SEQ ID NOs: 12.

In another embodiment, the reverse primer of the first PCR amplification is an oligonucleotide capable of hybridizing to mRNAs encoding TCRβ chains, wherein said oligonucleotide hybridizes to a target sequence within the nucleotide sequence encoding the constant region of the TCRβ chain, wherein the target sequence either comprises the target sequence of the oligonucleotide used for reverse transcribing the mRNA into the first cDNA strand or is located 5' of said target sequence or overlaps with said target sequence. Preferably said reverse primer is an oligonucleotide comprising the nucleotide sequence as shown in SEQ ID NOs: 11.

In another embodiment, the reverse primer of the first PCR amplification is an oligonucleotide capable of hybridizing to mRNAs encoding HLA I isotypes, wherein said oligonucleotide hybridizes to a target sequence within a nucleotide sequence transcribed from a conserved region of exon 3 or exon 4 of an HLA I allele and wherein said target sequence either comprises the target sequence of the oligonucleotide used for reverse transcribing said mRNA or is located 5' of said target sequence. Preferably said reverse primer is capable of hybridizing to a target sequence which is located within exon 3 or exon 4, more preferably within exon 3. Preferably said HLA I is HLA-A, HLA-B and HLA-C. Preferably said reverse primer is an oligonucleotide comprising the nucleotide sequence selected from the group consisting of SEQ ID NOs: 8, 13 to 15, 20, 29 and 33 to 35.

A second PCR amplification may comprise or make use of the same forward and reverse primer used in the first PCR amplification. Preferably, however, either the forward primer or the reverse primer or both primer bind to a target sequence which is located 5' to the target sequence of the first PCR amplification. The target sequences for the primers of the first PCR amplification and of the second PCR amplification may overlap by 1-30 nucleotides. Preferably, however, at least one of the target sequences of the primers of the second PCR amplification is separated from the target sequence of the first PCR amplification. Preferably the target sequence is separated by at least 1-100 nucleotides, preferably by 1-50 nucleotides.

In a preferred embodiment, the forward primer of the second PCR amplification is an oligonucleotide of the kit of the present invention, wherein said oligonucleotide is an oligonucleotide capable of hybridizing to the nucleotide sequence of the primer binding site provided by the template switching oligonucleotide.

In another preferred embodiment, the forward primer of the second PCR amplification is an oligonucleotide capable of hybridizing to a nucleotide sequence of mRNA encoding an HLA I isotype, wherein the complementary sequence of the target sequence to which the oligonucleotide hybridizes is preferably located at nucleotide position 97 of SEQ ID NO: 1 or 5' of said position and wherein said complementary sequence of the target sequence is a nucleotide sequence transcribed from or encoding a conserved region of an HLA I allele, wherein the target sequence of said forward primer is located 5' of the target sequence of the forward primer used in the first PCR amplification. In an alternative embodiment, the complementary sequence of the target sequence to which said oligonucleotide hybridizes, i.e. the forward primer of the second PCR amplification, is preferably located at nucleotide position 180 of SEQ ID NO: 1 or 5' of said position and wherein said complementary sequence of the target sequence is a nucleotide sequence transcribed from or encoding a conserved region of an HLA I allele, wherein the target sequence of said forward primer is preferably located 5' of the target sequence of the forward primer used in the first PCR amplification. Said target sequences may overlap by 1-30 nucleotides. Preferably, the term located at means that nucleotide position 97 is the last nucleotide of the complementary sequence of the target sequence or is located 20 nucleotides 5' or 3' of said position. Preferably, however, the target sequence of the primer of the second PCR amplification is separated from the target sequence of the first PCR amplification, preferably by at least 1-100 nucleotides, more preferably by 1-50 nucleotides. Preferably said forward primer is an oligonucleotide comprising the nucleotide sequence selected from the group consisting of SEQ ID NOs: 23, 31 and 32.

In a preferred embodiment, the forward primer of the present invention which is used for the second PCR is an oligonucleotide, which contains at the 5' terminus 1, 2, 3, 4 or 5 additional nucleotides, preferably random nucleotides selected from ATGC. Preferably, the PCR product generated by the second PCR amplification is generated by making use of degenerated oligonucleotides, i.e. of a mixture of forward primers with 1, 2, 3, 4 or 5 additional nucleotides, preferably random nucleotides selected from ATGC. Preferably, said forward primer of the mixture comprises a nucleotide sequence as shown in SEQ ID NO: 10, 16, 30 or 36.

In another preferred embodiment the reverse primer of the second PCR amplification is an oligonucleotide of the kit of the present invention, wherein said oligonucleotide is reverse primer selected from group (III) of oligonucleotides as defined herein below. Preferably, the reverse primer of the second PCR amplification is an oligonucleotide capable of hybridizing to an mRNA encoding the TCRα gene, wherein said oligonucleotide hybridizes to a target sequence within the nucleotide sequence encoding the constant region of the TCRα chain, wherein the target sequence either comprises the target sequence of the reverse primer of the first PCR amplification which hybridizes to mRNA encoding the TCRα chain or it is located 5' of said target sequence. Said target sequences may overlap by 1-30 nucleotides. Preferably, however, the target sequence of the primer of the second PCR amplification is separated from the target sequence of the first PCR amplification, preferably by at least 1-100 nucleotides, more preferably by 1-50 nucleotides. Preferably said reverse primer is an oligonucleotide comprising the nucleotide sequence as shown in SEQ ID NO: 19 or 39.

In another preferred embodiment the reverse primer of the second PCR amplification is an oligonucleotide of the kit of the present invention, wherein said oligonucleotide is reverse primer selected from group (III) of oligonucleotides as defined herein below. Preferably, the reverse primer of the second PCR amplification is an oligonucleotide capable of hybridizing to an mRNA encoding the TCRβ gene, wherein said oligonucleotide hybridizes to a target sequence within the nucleotide sequence encoding the constant region of the TCRβ chain, wherein the target sequence either comprises the target sequence of the reverse primer of the first PCR amplification which hybridizes to mRNA encoding the TCRβ gene or it is located 5' of said target sequence. Said target sequences may overlap by 1-30 nucleotides. Preferably, however, the target sequence of the primer of the second PCR amplification is separated from the target sequence of the first PCR amplification, preferably by at least 1-100 nucleotides, more preferably by 1-50 nucleotides. Preferably said reverse primer is an oligonucleotide comprising the nucleotide sequence selected from the group consisting of SEQ ID NOs: 17 to 18, 37 and 38.

In another preferred embodiment the reverse primer of the second PCR amplification is an oligonucleotide capable of hybridizing to mRNA encoding an HLA I isotype, wherein the oligonucleotide hybridizes to target sequence which is preferably located 3' of nucleotide position 561 of SEQ ID NO: 1. Preferably, the term located at means that nucleotide position 561 is the last nucleotide of the complementary sequence of the target sequence or is located 20 nucleotides 5' or 3' of said position. In one embodiment, said reverse primer binds to a target sequence, which is identical to the target sequence of the corresponding primer of the first PCR amplification. Alternatively, the target sequences may overlap by 1-30 nucleotides. Preferably, however, the target sequence of the primer of the second PCR amplification is separated from the target sequence of the first PCR amplification, preferably by at least 1-100 nucleotides, more preferably by 1-50 nucleotides.

In one embodiment, HLA I is HLA-A, HLA-B and HLA-C. In another embodiment, the reverse primer used for the synthesis of the first cDNA strand is an oligonucleotide of group (I) of oligonucleotides which is capable of hybridizing to an mRNA encoding HLA I and which hybridizes to a target sequence within exon 4. In another embodiment, the reverse primer of the first PCR amplification is an oligonucleotide of group (II) of oligonucleotides which is capable of hybridizing to an mRNA encoding HLA I and which hybridizes to a target sequence within exon 3 or exon 4. In another embodiment, the reverse primer of the second PCR amplification is an oligonucleotide of group (III) of oligonucleotides which is capable of hybridizing to an mRNA encoding HLA I and which is preferably capable of hybridizing to a target sequence within exon 3.

In another embodiment, the reverse primer used for synthesis of the first cDNA strand is an oligonucleotide of the first group of oligonucleotides described herein below with respect to the kit of the present invention. Preferably, said reverse primer is an oligonucleotide comprising a nucleotide sequence selected from the group consisting of:

(a) (5'-CATCAGAATCCTTACTTTGTGACAC-3'), SEQ ID NO: 7

(b) (5'-CACGTGGTCGGGGWAGAAGC-3'); SEQ ID NO: 6

(c) (5'-CTCAGRGTGRCYTCATGGTCAGAG-3'), SEQ ID NO: 8 and (d) (5'-GTGTCCTGRGTYTGGTCCTC-3'). SEQ ID NO: 29

In another embodiment, the primer of the first PCR amplification is an oligonucleotide comprising a nucleotide sequence selected from the group consisting of:

(a) (5' AAGCAGTGGTATCAACGCAGAGT 3'), SEQ ID NO: 10

(b) (5' TTAGAGTCTCTCAGCTGGTACACGGCAG 3'), SEQ ID NO: 12

(c) (5' GGCTCAAACACAGCGACCTCGGGTG 3'), SEQ ID NO: 11

(d) (5' CTGCGGAGCSMSTCCACGCAC 3') SEQ ID NO: 13

(e) (5' GCTCYCAYTCCATGARGTATTTC 3'), SEQ ID NO: 23

(f) (5' AAGCAGTGGTATCAACGCAGAGTAC 3'), SEQ ID NO: 30

(g) (5' TGGCCCTGACCSAGACCTGGGC 3'), SEQ ID NO: 31

(h) (5' GTGGGCTACGTGGACGRCAC 3'), SEQ ID NO: 32

(i) (5' GGTCAGTGTGATCTCCGCAGGGTAG 3'), SEQ ID NO: 33

(j) (5' TCCTTCCCGTTCTYCAGGTRTCTGCG 3'), SEQ ID NO: 34 and (k) (5' TCCTTCCCRTTCTYCAGGTRTCTGCG 3'). SEQ ID NO: 35

In another embodiment, the primer of the second PCR amplification is an oligonucleotide comprising a nucleotide sequence selected from the group consisting of:

(a) (5' NNNNNAAGCAGTGGTATCAACGCAGAGT 3'), SEQ ID NO: 16

(b) (5' GTACACGGCAGGGTCAGGGTTC 3'), SEQ ID NO: 19

(c) (5' CGGGTGGGAACACCTTGTTCAGGT 3'), SEQ ID NO: 17

(d) (5' CGGGTGGGAACACGTTTTTCAGGT 3'), SEQ ID NO: 18

(e) (5' GCTCYCAYTCCATGARGTATTTC 3'), SEQ ID NO: 23

(f) (5' CTGCGGAGCSMSTCCACGCAC 3') SEQ ID NO: 20

(g) (5' GTGGGCTACGTGGACGRCAC 3'), SEQ ID NO: 32

(h) (5' GGTCAGTGTGATCTCCGCAGGGTAG 3'), SEQ ID NO: 33

(i) (5' TCCTTCCCGTTCTYCAGGTRTCTGCG 3'), SEQ ID NO: 34

(j) (5' TCCTTCCCRTTCTYCAGGTRTCTGCG 3'), SEQ ID NO: 35

(k) (5' NNNNNAAGCAGTGGTATCAACGCAGAGTAC 3'), SEQ ID NO: 36

(l) (5' GGTGGGAACACCTTGTTCAGGTCC 3'), SEQ ID NO: 37

(m) (5' GGGTGGGAACACGTTTTTCAGGTCC 3'), SEQ ID NO: 38 and (n) (5' TGGTACACGGCAGGGTCAGGGTTC 3'). SEQ ID NO: 39

Preferably the reverse transcription of mRNA encoding T cell receptor chains and the reverse transcription of mRNA encoding MHC/HLA isotypes and/or one or more subsequent PCR amplifications are carried out in the same test tube, i.e. in the same reaction mixture.

In another embodiment, the samples are singularized to establish gene expression profiles of single cells or of groups of single cells. This embodiment aims at establishing gene expression profiles derived from single cells. Thus, prior to the step of reverse transcription, intact cells are separated from each other, for example by treating the sample with proteases or other agents capable of destroying cell surface interactions and, thus, tissue. The term "singularize" as used herein means that the cells of the sample are separated from each other.

In a further embodiment, concluding which individual T cell receptor is involved in the immune response comprises: (i) determining the frequency of mRNAs encoding individual TCRα-chain and TCRβ-chain; (ii) concluding on the TCRα-chain and TCRβ-chain of the T cell receptor involved in the immune response by: (a) identifying the TCRα-chain which is encoded by the most frequent mRNA encoding a TCRα-chain, and by (b) identifying the TCRβ-chain which is encoded by the most frequent mRNA encoding a TCRβ-chain; and (iii) validating the T cell receptor by correlation to antigen and MHC/HLA information.

The method of the present invention allows to specify the T cell receptor, which is involved in the immune response against the antigen. To this end, the frequency of the mRNAs encoding T cell receptor chains is determined, the most frequent mRNAs encoding a TCRα-chain and a TCRβ-chain are identified and combined and the biological activity of said T cell receptor composed of said TCRα-chain and of said TCRβ-chain is validated by correlation to antigen and MHC/HLA information, wherein validation means the confirmation of the ability of an antigen to elicit an immune response in dependent on the presence of a specific combination of TCRα, TCRβ and MHC/HLA isotype e.g. by a Luciferase cytotoxicity assay or a ELISPOT assay.

"Determining the frequency of mRNAs encoding individual TCRα-chain and TCRβ-chain" comprises establishing a partial nucleotide sequence of mRNAs encoding different TCRα-chain and TCRβ-chain.

As used throughout the specification, a portion of a nucleotide sequence or a partial nucleotide sequence or a fragment of a nucleotide sequence or a primer or an oligonucleotide refers to a nucleotide sequence comprising at least or up to 5, 6, 7, 8, 9, 10, 11, 12, 13, 14, 15, 17, 18, 19, 20, 21, 22, 23, 24, 25, 30, 40, 50, 60, 70, 80, 90, 100, 150, 200, 300, 400, 500 or even more nucleotides.

Preferably said partial nucleotide sequence comprises the nucleotide sequence encoding the complete V domain or a portion of said domain. Said portion of the V domain may be selected from the group consisting of CDR1, CDR2 and CDR3 or a fragment of CDR1, CDR2 and CDR3. Preferably mRNAs comprising identical CDR1, CDR2 and/or CDR3 are categorized and quantified. Typically, the most frequent mRNA encoding a TCRα-chain and the most frequent mRNA encoding a TCRβ-chain will indicate the TCRα-chain and the TCRβ-chain of the T cell receptor involved in the immune response. However, the method of the present invention comprises a step of validating the T cell receptor by correlation to antigen and MHC/HLA information. This step allows correcting the experimentally determined frequencies of mRNAs encoding TCRα-chains and TCRβ-chains by excluding mRNAs encoding specific TCRα-chains and TCRβ-chains or combinations of TCRα-chains and TCRβ-chains, which are not involved in the immune response against the antigen. Typically, a T cell receptor is validated by correlation to antigen and MHC/HLA information, as described herein above.

In another embodiment, the first and the second sample are taken from the same subject. Preferably, the first sample is obtained prior to the second sample and the second sample is obtained subsequent to the first sample. However, the first and the second sample may also be obtained at essentially the same point in time. Preferably, the first sample is a sample that is obtained before the subject has been exposed to an antigen, while the second sample is a sample obtained after exposure to the antigen. The term "first sample" may also refer to a sample obtained from tissue which is free of a disease or from tissue which does not contain the antigen. Likewise, the term "second sample" may also refer to a sample obtained from diseased tissue or from tissue, which contains the antigen. For example, the "second sample" may be obtained from cancerous tissue, while the first sample may be obtained from non-cancerous tissue. Preferably, the "first sample" and the "second sample" are obtained from the same type of tissue. For example, the "first sample" may be obtained from normal liver tissue of the subject, while the "second sample" is obtained from nearby cancerous tissue of the same subject.

According to the invention, the term "disease" includes inflammatory diseases, autoimmune diseases or any pathological state in which the subject is exposed to antigens, which are typically not present in somatic tissue of the subject. Such antigens comprise foreign antigens derived for example from viruses, bacteria, protozoa or fungi. Also comprised are antigens encoded by the DNA of the subject but not expressed in most healthy somatic tissues of the subject, including tumor-associated antigens, particularly abnormally expressed tumor-associated antigens. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the matastases thereof. Examples thereof are lung carcinomas, mamma carcinomas, prostate carcinomas, colon carcinomas, renal cell carcinomas, cervical carcinomas, or metastases of the cancer types or tumors described above.

According to the invention, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids.

In another embodiment, the method of the present invention comprises the additional step of comparing the expression profiles of the subject to at least one expression profile of a different subject or of a group of subjects. The term "group of subjects" refers to a group comprising at least 2, 3, 4 and even more subjects. The group of subjects may even include several hundred or several thousand subjects. The term "group of subjects" includes individual expression profiles and average expression profiles. In one aspect, the term "group of subjects" includes a first group of subjects which are not affected from a disease and a second group of subjects, which are affected from the disease.

In another embodiment, the gene expression profile of the first and/or the second sample is used to create a database. The database may include gene expression profiles obtained one or more subjects. The database may include gene expression profiles from existing databases including for example published databases or publically accessible databases.

The teaching of the present invention also envisages comparing the gene expression profile established from a sample with one or more gene expression profiles stored in a database. Said database may include gene expression profiles of the same subject and/or gene expression profiles of other subjects. To this end, the gene expression profile of the first sample can be a gene expression profile taken from a database.

In another embodiment, the antigen referred to herein is a tumor antigen and said antigen presenting cell is a tumor cell. In another embodiment, the antigen referred to herein is a viral antigen and said antigen presenting cell is a virus infected cell. In another embodiment, the antigen referred to herein is an auto antigen.

In another embodiment, the first sample is obtained prior to vaccination of the subject and the second sample is obtained subsequent to vaccination, wherein vaccination comprises administration of at least one antigen.

In a preferred embodiment, the mRNA is identified by sequencing of a nucleic acid molecule. Preferably, said nucleic acid molecule is a DNA strand synthesized by the method of the present invention. Preferably, said DNA strand is a coding strand for an HLA isotype or a T cell receptor chain and/or a strand complementary to a coding strand. Preferably, said DNA strand is a product of the first or the second PCR amplification described herein.

In a preferred embodiment, the mRNA is identified and/or quantified by determining the nucleotide sequence and/or amount and/or concentration of the PCR product described herein. Preferably, the nucleotide sequence and/or the amount and/or concentration is determined by next generation sequencing. For a review of next generation sequencing we refer to Mardis E. R., Trends in Genetics 2007, 24: 133-141. Sequencing and/or sample preparation is preferably according to the standard protocol for MiSeq/HiSeq 2000 (Illumina Inc.).

The present invention also relates to a kit for performing the method of the present invention, comprising at least two groups of oligonucleotides, wherein:
the first group (I) comprises:
(I.1) a first oligonucleotide capable of hybridizing to an mRNA encoding the TCRα gene, wherein said first oligonucleotide hybridizes to a target sequence within the nucleotide sequence encoding the constant region of the TCRα chain;
(I.2) a first oligonucleotide capable of hybridizing to an mRNA encoding the TCRβ gene, wherein said first oligonucleotide hybridizes to a target sequence within the nucleotide sequence encoding the constant region of the TCRβ chain;
(I.3) a first oligonucleotide capable of hybridizing to an mRNA encoding MHC I/HLA I, wherein said first oligonucleotide hybridizes to a target sequence within a nucleotide sequence transcribed from a conserved region of exon 3 or exon 4 of an MHC I/HLA I allele;
(I.4) a template switching oligonucleotide providing a primer binding site and at least 3 consecutive G nucleotides at the 3' end; and the second group (II) comprises:
(II.1) an oligonucleotide which is capable of hybridizing to the nucleotide sequence of the primer binding site provided by the template switching oligonucleotide according to item (I.4) of the first group of oligonucleotides.

According to the teaching of the present invention, the first oligonucleotide capable of hybridizing to mRNA encoding the TCRβ gene is an oligonucleotide which hybridizes to a target sequence within the nucleotide sequence encoding the constant region of the TCRβ chain, wherein said constant region of the TCRβ chain is encoded by Cβ1 or Cβ2. Preferably, said oligonucleotide is capable of hybridizing to nucleotide sequences encoding Cβ1 and/or Cβ2.

An oligonucleotide or primer of the present invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly. In preferred embodiments, an oligonucleotide of the invention is a "modified" oligonucleotide. Here, the oligonucleotide may be modified in very different ways, without impairing its ability to bind its target, in order to increase, for example, its stability. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

An oligonucleotide or primer according to the present invention also includes "degenerated" oligonucleotides or "degenerated" primers, which are mixtures of oligonucleotides according to the general definition which differ in at least one nucleotide position and which have the same length or a similar length and have at least or up to 80%, preferentially at least or up to 90% and more preferentially at least or up to 95% or even more sequence identity. The differing nucleotide positions "degenerated nucleotides" of the mixture of oligonucleotides are indicated by wild cards representing groups of alternative nucleotides. The following abbreviations are used to characterize the oligonucleotides and primers of the present invention:
A→adenosine,
C→cytidine
G→guanine
T→thymidine
U→uridine For "degenerated" oligonucleotides or "degenerated" primers:
M→A or C (amino)
S→G or C (strong)
W→A or T (weak)
R→G or A (purine)
Y→T or C (pyrimidine)
K→G or T (keto)
B→G or T or C
D→G or A or T
H→A or C or T
V→G or C or A
N→A or G or C or T (any)

In a further embodiment, the oligonucleotides and primer of the present invention hybridize with their target nucleic acid sequence under low stringency, more preferably under medium stringency and most preferably under high stringency conditions.

Preferably the oligonucleotides according to the invention have a sequence of 6-60, in particular 10-30, 15-30 and 20-30, contiguous nucleotides of the target nucleic acid sequence and preferably are complementary to the target nucleic acid sequence or to a part thereof. According to the invention, complementary nucleic acids sequences hybridize over at least 40%, in particular at least 50%, at least 60%, at least 70%, at least 80%, at least 90% and preferably at least 95%, at least 98%, at least 99% nucleotides or are 100% nucleotides.

Preferably the template switching oligonucleotide (termed "TSO") of the present invention comprises, from 5' to 3', a nucleotide sequence which is complementary to a nucleotide sequence forming a primer binding site for a primer used in a subsequent PCR step of the method of the invention (the primer binding site is termed "PBS", the nucleotide sequence complementary to the PBS is termed "cPBS") and at least 3 consecutive G nucleotides (termed "poly(G)") and, optionally, a linker of up to 2, 3, 4, 5, 6, 7, 8, 9, 10, 11, 12, 13, 14, 15 or of up to 20 nucleotides between the cPBS and the poly(G). Preferably the least 3 consecutive G nucleotides are ribonucleotides. The term "primer binding site" refers to a nucleotide sequence at the 3' end of the first cDNA strand introduced by the template switching oligonucleotide. Preferably, the PBS and the corresponding cPBS comprises at least 8, 9, 10, 11, 12, 13, 14, 15, 16, 17, 18, 19 or 20 nucleotides. Preferably the nucleotide sequence forming the PBS is unique, i.e. a sequence of consecutive nucleotides not present in the DNA of the subject. Preferably, the nucleotide sequence of the cPBS is the nucleotide sequence shown in SEQ ID NO: 10 (5'-AAGCAGTGGTATCAACGCAGAGT-3') or the nucleotide sequence shown in SEQ ID NO: 30 (5' AAGCAGTGGTATCAACGCAGAG-TAC 3') and the sequence of the template switching oligonucleotide is the nucleotide sequence shown in SEQ ID NO: 5 (5'-AAGCAGTGGTATCAACGCAGAGTACGCGGG-3') or in SEQ ID NO: 41 (5'-AAGCAGTGGTAT-CAACGCAGAGTACATGGG-3').

In one embodiment, the second group (II) of oligonucleotides of the kit of the present invention further comprises:

(II.2) a second oligonucleotide capable of hybridizing to an mRNA encoding the TCRα gene, wherein said second oligonucleotide hybridizes to a target sequence within the nucleotide sequence encoding the constant region of the TCRα chain, wherein the target sequence either comprises the target sequence of said first oligonucleotide which hybridizes to the mRNA encoding the TCRα chain or is located 5' of said target sequence;

(II.3) a second oligonucleotide capable of hybridizing to an mRNA encoding the TCRβ chain, wherein said second oligonucleotide hybridizes to a target sequence within the nucleotide sequence encoding the constant region of the TCRβ chain, wherein the target sequence either comprises the target sequence of said first oligonucleotide which hybridizes to the mRNA encoding the TCRβ chain or is located 5' of said target sequence; and (II.4) a second oligonucleotide capable of hybridizing to an mRNA encoding MHC I/HLA I, wherein said second oligonucleotide hybridizes to a target sequence within a nucleotide sequence transcribed from a conserved region of exon 3 or exon 4 of MHC I/HLA I and wherein said target sequence either comprises the target sequence of said first oligonucleotide which hybridizes to mRNA encoding MHC I/HLA I or is located 5' of said target sequence, and, optionally, (II.5) a second oligonucleotide hybridizing to a nucleotide sequence which is complementary to the nucleotide sequence of mRNA encoding an MHC MLA I, wherein the complementary sequence of the target sequence to which the oligonucleotide hybridizes is located 5' of nucleotide position 180 of SEQ ID NO: 1 or is located 5' of nucleotide position 97 of SEQ ID NO: 1 and wherein said complementary sequence of the target sequence is a nucleotide sequence encoding a conserved region of an HLA I allele.

In another embodiment, the kit further comprises a third group (III) of oligonucleotides comprising:

(III.1) an oligonucleotide capable of hybridizing to the nucleotide sequence of the primer binding site provided by the template switching oligonucleotide;

(III.2) a third oligonucleotide capable of hybridizing to an mRNA encoding the TCRα chain, wherein said third oligonucleotide hybridizes to a target sequence within the nucleotide sequence encoding the constant region of the TCRα chain, wherein the target sequence either comprises the target sequence of said second oligonucleotide which hybridizes to mRNA encoding the TCRα chain or is located 5' of said target sequence;

(III.3) a third oligonucleotide capable of hybridizing to an mRNA encoding the TCRβ chain, wherein said third oligonucleotide hybridizes to a target sequence within the nucleotide sequence encoding the constant region of the TCRα chain, wherein the target sequence either comprises the target sequence of said second oligonucleotide which hybridizes to mRNA encoding the TCRβ chain or is located 5' of said target sequence;

(III.4) an oligonucleotide capable of hybridizing to a nucleotide sequence which is complementary to the nucleotide sequence of mRNA encoding an MHC I/HLA I allele, wherein the complementary sequence of the target sequence to which the oligonucleotide hybridizes is preferably located 5' of nucleotide position 180 of SEQ ID NO: 1 or is preferably located 5' of nucleotide position 97 of SEQ ID NO: 1 and wherein said complementary sequence of the target sequence is a nucleotide sequence encoding a conserved region of an MHC I/HLA I allele; and (III.5) an oligonucleotide capable of hybridizing to mRNA encoding an MHC I/HLA I isotype, wherein the oligonucleotide hybridizes to target sequence which is preferably located 3' of nucleotide position 561 of SEQ ID NO: 1.

In one embodiment, the oligonucleotide or primer of the present invention comprises up to 5 degenerated nucleotides at its 5' end.

In one embodiment, said first oligonucleotide capable of hybridizing to an mRNA encoding HLA I hybridizes to HLA-A, HLA-B and HLA-C or to mRNA transcribed from the corresponding loci in a non-human organism.

In another embodiment, said first oligonucleotide capable of hybridizing to an mRNA encoding MHC I/HLA I hybridizes to a target sequence within exon 4.

In another embodiment, said second oligonucleotide capable of hybridizing to an mRNA encoding MHC I/HLA I hybridizes to a target sequence within exon 3.

In another embodiment, the first group of oligonucleotides comprises at least one oligonucleotide comprising a nucleotide sequence selected from the group consisting of:

(a)  (5' CATCAGAATCCTTACTTTGTGACAC 3'),   SEQ ID NO: 7

(b)  (5' CACGTGGTCGGGGWAGAAGC 3'),   SEQ ID NO: 6

(c)  (5' CTCAGRGTGRCYTCATGGTCAGAG 3'),   SEQ ID NO: 8

(d)  (5' AAGCAGTGGTATCAACGCAGAGTACGCGGG 3'),   SEQ ID NO: 5

(e) and  (5' AAGCAGTGGTATCAACGCAGAGTACATGGG 3'),   SEQ ID NO: 41

(f)  (5' GTGTCCTGRGTYTGGTCCTC 3').   SEQ ID NO: 29

In one embodiment, the second group of oligonucleotides comprises at least one oligonucleotide comprising a nucleotide sequence selected from the group consisting of:

(a) (5' AAGCAGTGGTATCAACGCAGAGT 3'), SEQ ID NO: 10

(b) (5' TTAGAGTCTCTCAGCTGGTACACGGCAG 3'), SEQ ID NO: 12

(c) (5' GGCTCAAACACAGCGACCTCGGGTG 3'), SEQ ID NO: 11

(d) (5' CTGCGGAGCSMSTCCACGCAC 3'), SEQ ID NO: 13

(e) (5' GCTCYCAYTCCATGARGTATTTC 3'), SEQ ID NO: 23

(f) (5' AAGCAGTGGTATCAACGCAGAGTAC 3'), SEQ ID NO: 30

(g) (5' TGGCCCTGACCSAGACCTGGGC 3'), SEQ ID NO: 31

(h) (5' GTGGGCTACGTGGACGRCAC 3'), SEQ ID NO: 32

(i) (5' GGTCAGTGTGATCTCCGCAGGGTAG 3'), SEQ ID NO: 33

(j) and (5' TCCTTCCCGTTCTYCAGGTRTCTGCG 3'), SEQ ID NO: 34

(k) (5' TCCTTCCCRTTCTYCAGGTRTCTGCG 3'). SEQ ID NO: 35

In one embodiment, the third group of oligonucleotides comprises at least one oligonucleotide comprising a nucleotide sequence selected from the group consisting of:

(a) (5' NNNNNAAGCAGTGGTATCAACGCAGAGT 3'), SEQ ID NO: 16

(b) (5' GTACACGGCAGGGTCAGGGTTC 3'), SEQ ID NO: 19

(c) (5' CGGGTGGGAACACCTTGTTCAGGT 3'), SEQ ID NO: 17

(d) (5' CGGGTGGGAACACGTTTTTCAGGT 3'), SEQ ID NO: 18

(e) (5' GCTCYCAYTCCATGARGTATTTC 3'), SEQ ID NO: 23

(f) (5' CTGCGGAGCSMSTCCACGCAC 3'), SEQ ID NO: 20

(g) (5' GTGGGCTACGTGGACGRCAC 3'), SEQ ID NO: 32

(h) (5' GGTCAGTGTGATCTCCGCAGGGTAG 3'), SEQ ID NO: 33

(i) (5' TCCTTCCCGTTCTYCAGGTRTCTGCG 3'), SEQ ID NO: 34

(j) (5' TCCTTCCCRTTCTYCAGGTRTCTGCG 3'), SEQ ID NO: 35

(k) (5' NNNNNAAGCAGTGGTATCAACGCAGAGTAC 3'), SEQ ID NO: 36

(l) (5' GGTGGGAACACCTTGTTCAGGTCC 3'), SEQ ID NO: 37

(m) (5' GGGTGGGAACACGTTTTTCAGGTCC 3'), SEQ ID NO: 38 and (n) (5' TGGTACACGGCAGGGTCAGGGTTC 3'). SEQ ID NO: 39

In another aspect, the present invention relates to the use of the method and the kit of the invention for diagnosing or monitoring a disease or for identifying patients which respond to, or which are likely to respond to, a therapeutic treatment of a disease described herein above.

The present invention also relates to a method of treating a patient by adoptive T cell therapy, comprising a T cell which has been identified by a method of the present invention.

Adoptive T cell therapy is based on adoptive transfer of T cells engineered to express a defined antigen-specific T cell receptor. Using such T cells, which express a defined TCRα chain and a defined TCRβ chain, identified by any of the methods of the present invention, antigens can be specifically targeted leading to selective destruction of targeted malignant or infected cells.

In one aspect the present invention relates to a method for providing antigen-specific lymphoid cells comprising the steps:

(a) generating a single antigen-reactive T cell by expressing at least a TCRα chain and a TCRβ chain identified by any of the methods of the present invention; and (b) introducing the single antigen-reactive T cell into a patient.

The following examples illustrate the invention:

Example 1

Method Development

HLA Genotyping is generally done in the context of hematopoietic stem cell transplantation (HSCT) with the aim to identify matching donors for HSCT by determining the alleles of the HLA-A, -B, -C, -DRB1 and -DQB1 loci (Jung, H. L., Shedding a new light in the HLA matching, Korean J Hematol. 2011; Nowak J., Role of HLA in hematopoietic SCT, Bone marrow transplantation 2008). The current state-of-the-art typing method in routine diagnostics is sequence-based typing (SBT) of exon 2 and 3 for HLA class I loci and exon 2 for HLA class II loci (Bettinotti M. P. et al., Comprehensive method for the typing of HLA-A, B, and C alleles by direct sequencing of PCR products obtained from genomic DNA. J Immunother 1997). The mentioned exons are the immunogenetically relevant exons encoding the protein domains responsible for antigen-binding (Strachan T., Complete nucleotide sequence of a functional class I HLA gene, HLA-A3: implications for the evolution of HLA genes. EMBO 1984; Mallisen M., Exon/intron organization and complete nucleotide sequence of an HLA gene. PNAS 1982; Kaufman J. F. et al., The class II molecules of the human and murine histocompatibility complex. Cell 1984). In addition, sequence information from exons 2 and 3 for HLA class I and exon 2 for HLA class II is in most cases sufficient for nonambiguous allele determination.

According to this, a protocol for determination of allele type and expression level of the HLA-A, -B, -C, -DRB1 and -DQB1 loci was developed allowing for combination with the TCR profiling procedure in one assay. The overall strategy is illustrated by FIG. 1, the primers mentioned in FIG. 1 are listed in Table 1. For TCR profiling, TCR-α and -β gene transcript are reverse transcribed and amplified using a SMART-RACE protocol (SMART-RACE=acronym of switching mechanism at 5' end of RNA transcript rapid amplification of cDNA-ends with polymerase chain reaction). First-strand SMART cDNA synthesis is performed using reverse primer specific for the constant region of TCR-α and -β genes (TRAC/TRBC) combined with the chimeric template-switching oligo TS-chim allowing for subsequent amplification of the first-strand cDNA via RACE-PCR without knowledge of the 5' sequences of the TCR transcripts. In this PCR reaction, TRAC/TRBC-specific reverse primers are used together with the universal TS-PCR forward primer that binds to a sequence tag introduced by the TS-chim oligo. A second semi-specific PCR step with nested TRAC/TRBC-specific reverse primer and the universal TS-PCR primer is then performed to increase the yield and specificity of the amplified TCR sequences.

TABLE 1 table of oligonucleotides used for cDNA synthesis and PCR:

| Name | Working name | SEQ ID NO: | Sequence |
|---|---|---|---|
| First strand cDNA synthesis | | | |
| TS-chim | TSO | 5 | AAGCAGTGGTATCAACGCAGAGTACGCGGG |
| TS-chim2 | TSO2 | 41 | AAGCAGTGGTATCAACGCAGAGTACATGGG |
| TRBC/TRBC_1st Strand1 | Step1_TRBC | 6 | CACGTGGTCGGGGWAGAAGC |
| TRAC/TRAC_1st Strand2 | Step1_TRAC | 7 | CATCAGAATCCTTACTTTGTGACAC |
| HLA-I_cDNAex4_as | | 8 | CTCAGRGTGRCYTCATGGTCAGAG |
| HLA-I_cDNAex4_as2 | | 29 | GTGTCCTGRGTYTGGTCCTC |
| HLA-II_cDNAex3_as | | 9 | CAGCATCTTGYTCTGKGCAGATTC |
| RACE ("First PCR") | | | |
| TS-PCR | TS_PCR | 10 | AAGCAGTGGTATCAACGCAGAGT |
| TS-PCR2 | | 30 | AAGCAGTGGTATCAACGCAGAGTAC |
| TRBCex1-as | Step2_TRBC | 11 | GGCTCAAACACAGCGACCTCGGGTG |
| TRACex1-Ph-as | Step2_TRAC | 12 | TTAGAGTCTCTCAGCTGGTACACGGCAG |
| HLA-I_ex1_s3 | | 31 | TGGCCCTGACCSAGACCTGGGC |
| HLA-I_ex2_s | | 23 | GCTCYCAYTCCATGARGTATTTC |
| HLA-I_ex2_s2 | | 32 | GTGGGCTACGTGGACGRCAC |
| HLA-I_ex3_as | | 13 | CTGCGGAGCSMSTCCACGCAC |
| HLA-I_ex4_as3 | | 33 | GGTCAGTGTGATCTCCGCAGGGTAG |
| HLA-I_ex3_as | | 20 | CTGCGGAGCSMSTCCACGCAC |
| HLA-I_ex3_as8 | | 34 | TCCTTCCCGTTCTYCAGGTRTCTGCG |
| HLA-I_ex3_as9 | | 35 | TCCTTCCCRTTCTYCAGGTRTCTGCG |
| HLA-I_cDNAex4_as | | 8 | CTCAGRGTGRCYTCATGGTCAGAG |
| HLA-I_cDNAex4_as2 | | 29 | GTGTCCTGRGTYTGGTCCTC |
| DRB_ex3_as | | 14 | CCACCTGACTTCAATGCTGCCTGG |
| DQB_ex3_as | | 15 | GTTGTGGTGGTTGAGGGCCTCTG |
| Nested PCR TCR ("Second PCR") | | | |
| TS-5N-PCR | 5N_TS_PCR | 16 | NNNNNAAGCAGTGGTATCAACGCAGAGT |
| TS-5N-PCR2 | | 36 | NNNNNAAGCAGTGGTATCAACGCAGAGTAC |
| TRBC1nest-as | Step3_TRBC1 | 17 | CGGGTGGGAACACCTTGTTCAGGT |
| PCR_B_3.2 | | 37 | GGTGGGAACACCTTGTTCAGGTCC |
| TRBC2nest-as | Step3_TRBC2 | 18 | CGGGTGGGAACACGTTTTTCAGGT |
| PCR_B_4.2 | | 38 | GGGTGGGAACACGTTTTTCAGGTCC |
| TRACnest1-as | Step3_TRAC | 19 | GTACACGGCAGGGTCAGGGTTC |
| Step3_TRAC_2 | | 39 | TGGTACACGGCAGGGTCAGGGTTC |
| Nested PCR HLA ("Second PCR") | | | |
| HLA-I_ex3_as | | 20 | CTGCGGAGCSMSTCCACGCAC |
| HLA-I_ex3_as8 | | 34 | TCCTTCCCGTTCTYCAGGTRTCTGCG |
| HLA-I_ex3_as9 | | 35 | TCCTTCCCRTTCTYCAGGTRTCTGCG |
| DRB_ex3_as | | 21 | CCACCTGACTTCAATGCTGCCTGG |
| DQB_ex3_as | | 22 | GTTGTGGTGGTTGAGGGCCTCTG |
| HLA-I_ex2_s | | 23 | GCTCYCAYTCCATGARGTATTTC |
| HLA-I_ex2_s2 | | 32 | GTGGGCTACGTGGACGRCAC |
| HLA-I_ex4_as3 | | 33 | GGTCAGTGTGATCTCCGCAGGGTAG |
| DRB_ex1_s | | 24 | GACAGTGACAYTGAYGGTGCTGAG |
| DQB1_ex1_s | | 25 | CAACTGTBACCTTGATGCTGKCG |

Figure 2A:
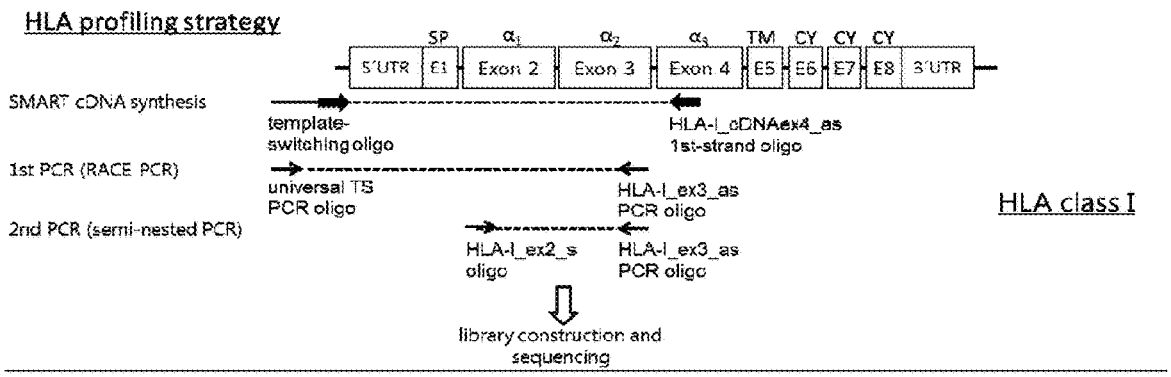
FIG. 2A shows a schematic overview of the strategy for profiling of mRNAs encoding HLA class I isotypes expressed in a sample.
Figure 2B:
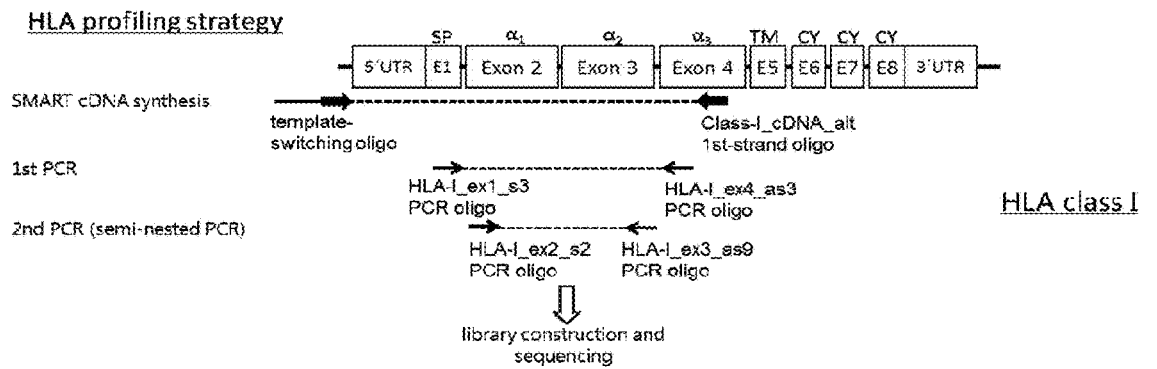
FIG. 2B shows a schematic overview of an alternative strategy for profiling of mRNAs encoding HLA class I isotypes expressed in a sample.
Figure 2C:
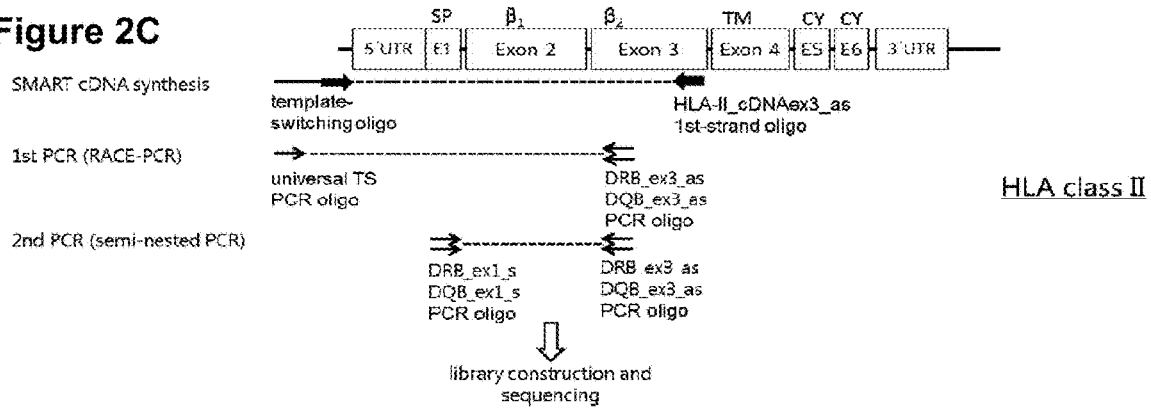
FIG. 2C shows a schematic overview of the strategy for profiling of mRNAs encoding HLA class II isotypes expressed in a sample.

An analogous three-step SMART-RACE PCR protocol, which is essentially based on the TCR profiling approach, was also developed for HLA profiling. For gene-specific reverse transcription, a generic reverse primer specific for HLA-I (A, B, C) and a generic reverse primer for HLA-II targeting the HLA-DRB1/3/4/5 and DQB1 loci were designed that are combined with the template-switching oligo TS-chim. The RACE PCR is performed with the universal forward primer TS-PCR and a generic HLA-I-specific reverse primer as well as one reverse primer for DRB1/3/4/5 and one for DQB1. In this case, sequence homology between DRB and DQB alleles was too low to design one generic primer targeting both class II loci. The described reverse primer are then used a second time in a gene-specific second PCR in combination with a generic forward primer for HLA-I loci, a forward primer specific for HLA-DRB1/3/4/5 and one specific for HLA-DQB1. Using this three-step protocol, amplicons are generated that cover exon 2 and 3 of HLA-I genes and exon 2 of DRB and DQB genes and can be sequenced, for example in a single paired-end sequencing run of the Illumina MiSeq sequencing system. The strategy, including two alternatives for HLA class I, is illustrated by FIG. 2.

Example 2

Combined TCR-HLA Profiling

Total RNA was extracted from (1×10^6) PBMCs using a silica spin-column kit with two columns per sample. For removal of genomic DNA, on-column DNaseI digestion was performed according to the manufacturer's instructions. Purified total RNA was eluted with $H_2O$ and the two eluates of one sample were pooled. 100 ng aliquots of total RNA were used for SMART-RACE (switching mechanism at 5' end of RNA transcript rapid amplification of cDNA-ends with polymerase chain reaction). First-strand cDNA was synthesized using reverse transcriptase capable of transcript switching, a set of TRAC/TRBC/HLA-I/HLA-II-specific oligos as well as template-switching oligo TS-chim providing a 5' template for the RACE reaction. For RACE (rapid amplification of cDNA ends), 8 µl first strand cDNA (1:5 diluted in TE buffer) was subjected to PCR amplification with a high fidelity proof-reading polymerase using TRAC/TRBC/HLA-I/HLA-DRB/HLA-DQB-specific antisense oligos as well as the published TS-PCR oligo for 18 cycles. Amplified TCR V(D)J fragments and HLA-I, HLA-DRB and HLA-DQB fragments were then purified using a silica spin-column Kit. One third of the eluate was used for 35 cycles of a nested TRAC/TRBC/HLA-I/HLA-II-specific PCR. Resulting TRA, TRB and HLA-I fragments of ~500-600 bp length and HLA-DRB- and DQB fragments of ~390-440 bp length were separated by preparative agarose gel electrophoresis, excised and purified using a silica spin-column gel extraction Kit. Purified PCR products were subjected to library preparation and sequencing using standard protocols for Illumina MiSeq sequencing system.

Example 3

TCR-HLA Profiling Compared to Random Priming

Using gene-unspecific priming for reverse transcription, all poly(A)-mRNAs will be transcribed unspecifically into cDNA of which only a small fraction will then represent the gene of interest. Gene-specific priming leads to synthesis of only specific cDNAs avoiding RT of unspecific transcripts. This will reduce the unspecific background resulting in more specific PCR products and in the end better sequence analysis because of the higher proportion of specific sequence reads mapping to the gene of interest. Furthermore, the usage of gene-specific primers for reverse transcription will produce the desired cDNA sequences with higher efficiency thus allowing reduce the cycle number in the subsequent PCR reactions. This may reduce the risk for artificial point mutations derived from errors during PCR.

Example 4

Determining Expression Status

The relative expression of identified HLA alleles of a patient is determined on the basis of the number of sequence reads matching to the same reference sequence. Differences in amplification efficiency of the individual PCR reactions are determined by quantitative realtime-PCR using in-vitro transcribed RNA coding for a set of representative HLA isotypes as template. The resulting correction factor enables the quantitative comparison of the expression levels of identified HLA alleles or isotypes.

Example 5

Combined TCR Profiling and HLA Typing of a Clinical Sample Before/after Therapy (Personalized) Immunotherapies exert their primary effects on immune-cell subpopulations and not the tumor itself. Consequently, the monitoring of therapy-induced alterations of the composition, function and phenotype of immune cell subsets is a straightforward approach to characterize the pharmacodynamics activity of the immune-intervention. In particular results obtained from TCR profiling can become available shortly after therapy and provide a quantitative assessment of the antigen-specific engagement of the immune system. The generated data can be used to (i) guide further clinical development, (ii) identify responders vs non-responders early on, or even (iii) influence decision making of individual patients.

The aim of this experiment was to stimulate human PBMC samples with known reactivity against defined antigens for subsequent TCR profiling. To this end we thawed sample specimens obtained from a patient with verified NY-ESO-1, and tetanus-specific T cell responses. Frozen aliquots of PBMCs, isolated from leukapheresis obtained before and after vaccination (visit 1 vs visit 10) were thawed showing high viability of >95%. For each visit and antigen-specific stimulation reaction 8×10^6 cells (2×10^6 cells/ml) were cultivated in IMD medium and 10% human serum in a 6-well and stimulated for 10 days with a NY-ESO-1 HLA-matched peptide pool of 4 positively detected peptides, or with a Tetanus pool containing P2, p16 and P17 peptides. As negative control stimulus no peptides were added to a separate stimulation culture. Each peptide was used in a final concentration of 2.5 µg/ml. One day after initiation of stimulation IL-2 (10 U/ml) and IL-15 (5 ng/ml) were added to the culture and after 4 and 8 days of cultivation a media change was performed. 4×10^6 cells of V1 and V10 before stimulation and 4×10^6 cells of each visit and each peptide stimulation reaction were collected for TCR profiling. The cell pellets were frozen and stored at −80° C.

RNA isolated from the pellets was used for template-switch-based 5'rapid amplification of cDNA with HLA- and TCR-specific primers. Using the combined TCR and HLA protocol the cDNAs were amplified in two PCR steps. Afterwards the PCR products were separated by gel electrophoresis, excised, purified, subjected to library preparation and sequenced with the Illumina MiSeq System.

Figure 3A:
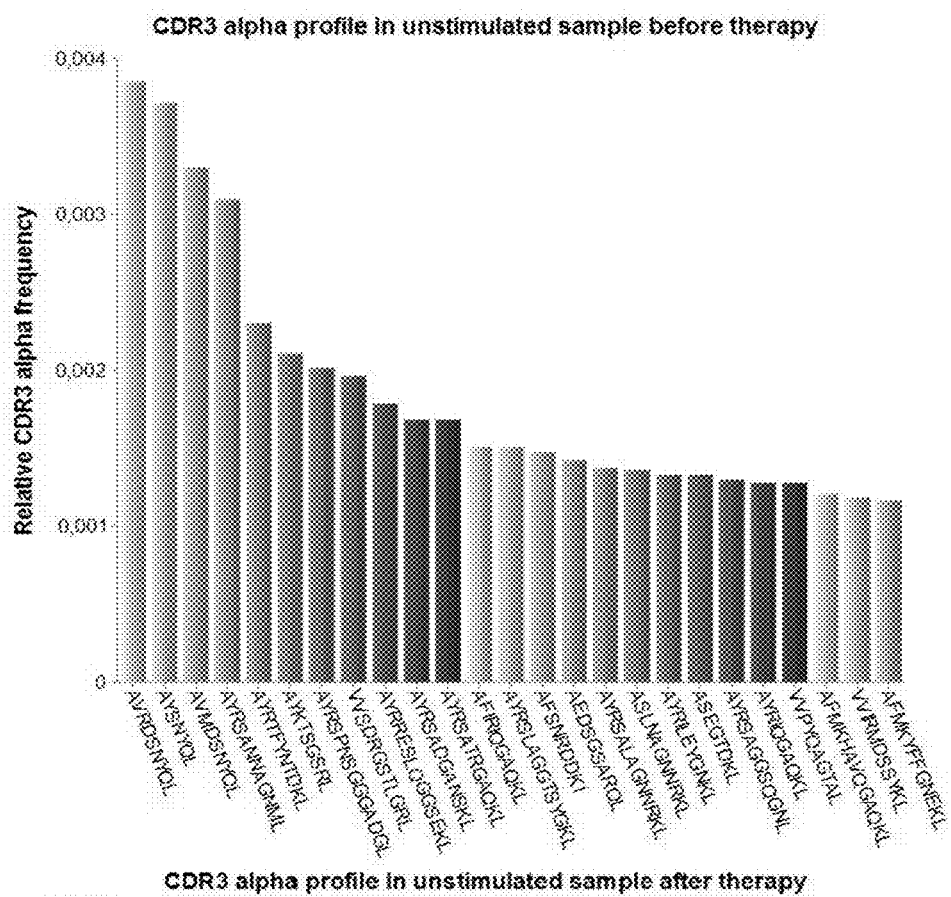
FIG. 3A and FIG. 3B show TCR profiling of TCR-alpha chains before/after vaccination therapy without further stimulation. The CDR3 profile has been established without in vitro stimulation of the PBMCs derived from blood samples. Shown is the patient's CDR3 profile before (FIG. 3A) and after (FIG. 3B) therapy.
Figure 3B:
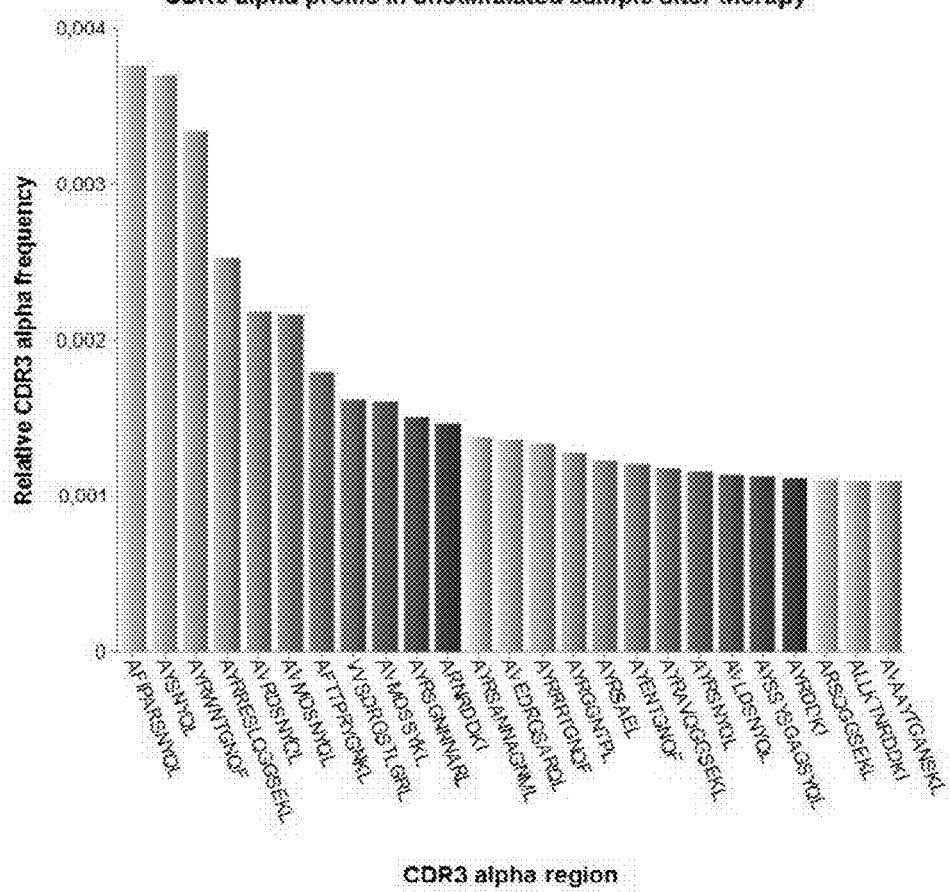
Figure 7A:
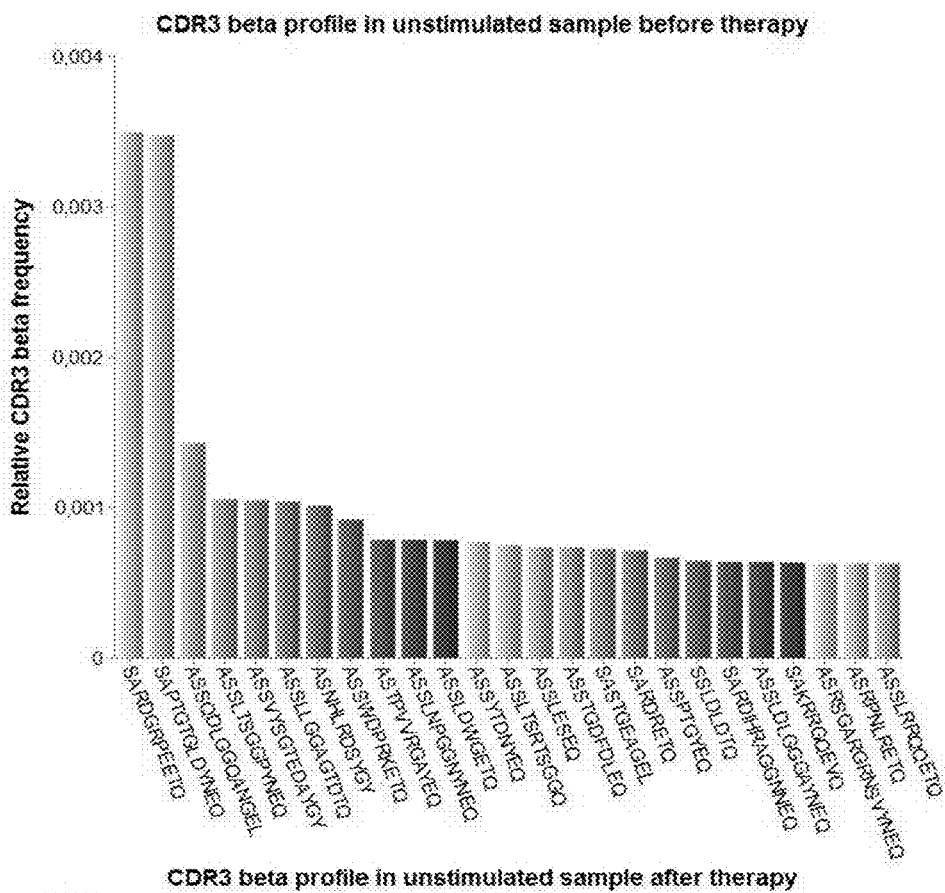
FIG. 7A and FIG. 7B show TCR profiling of TCR-beta chains before/after vaccination therapy without further stimulation. The CDR3 profile has been established without in vitro stimulation of the PBMCs derived from blood samples. The figure shows the patient's CDR3 profile before (FIG. 7A) and after (FIG. 7B) therapy.
Figure 7B:
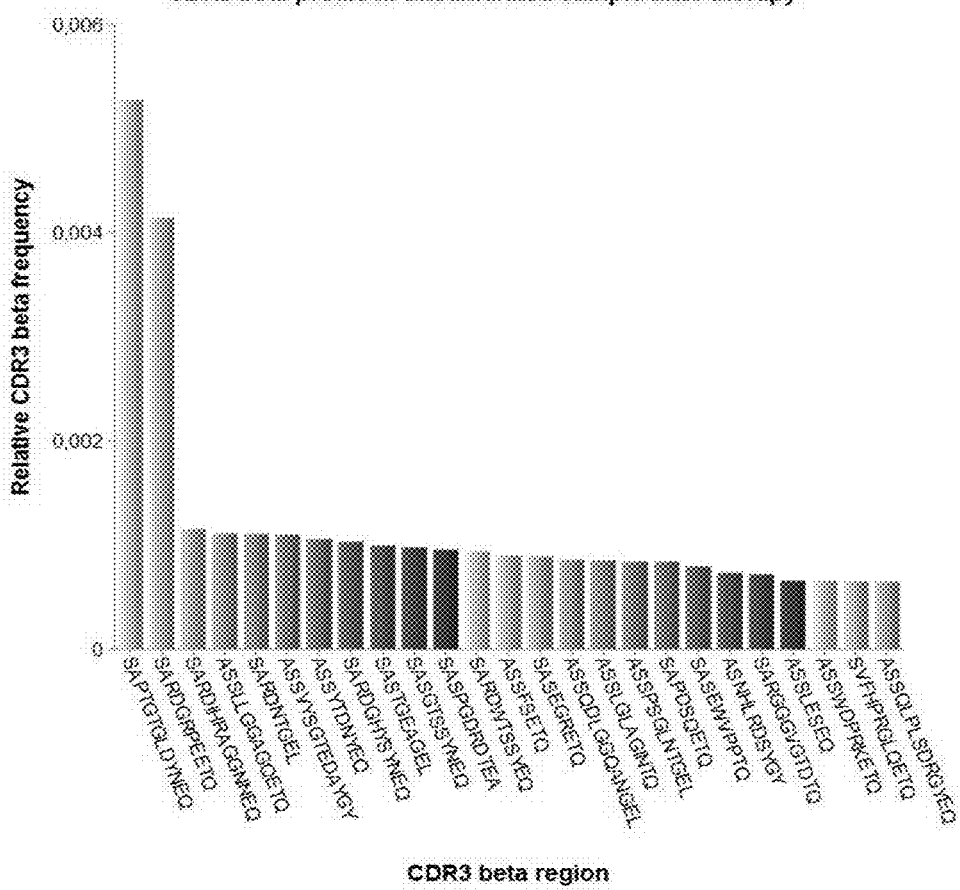

In the unstimulated samples, the T cell repertoire shift due to therapy was expected to be low. Consequently, no significant shift of TCR profile was observed between the two samples for TCR alpha and beta chain (FIGS. 3 and 7).

Figure 4A:
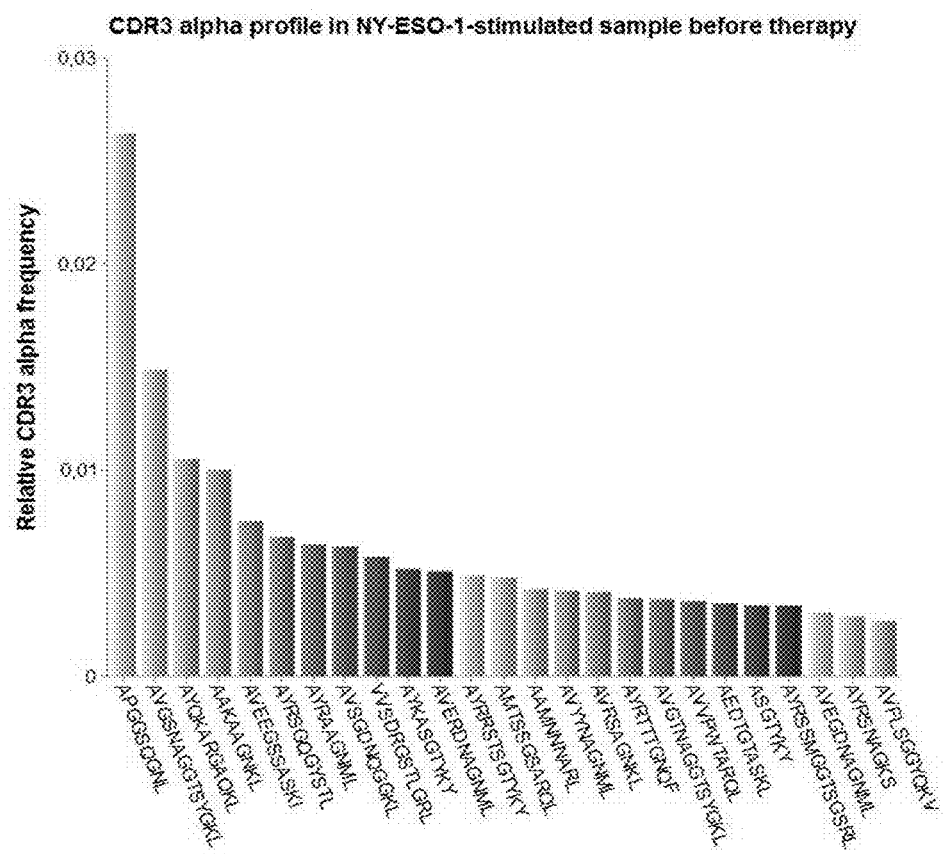
FIG. 4A and FIG. 4B show TCR profiling of TCR-alpha chains before/after vaccination therapy, where PBMCs derived from the blood samples have been stimulated in vitro by NY-ESO-1 antigen mix. The figure shows the patient's CDR3 profile before (FIG. 4A) and after (FIG. 4B) therapy.
Figure 4B:
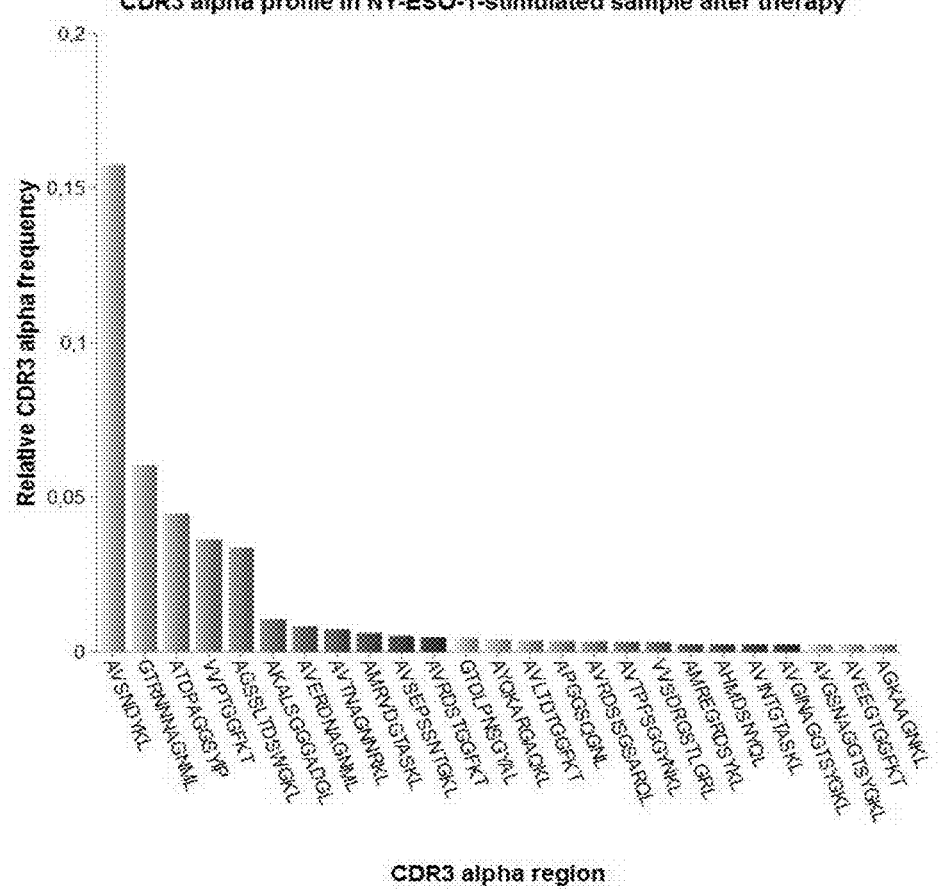
Figure 5A:
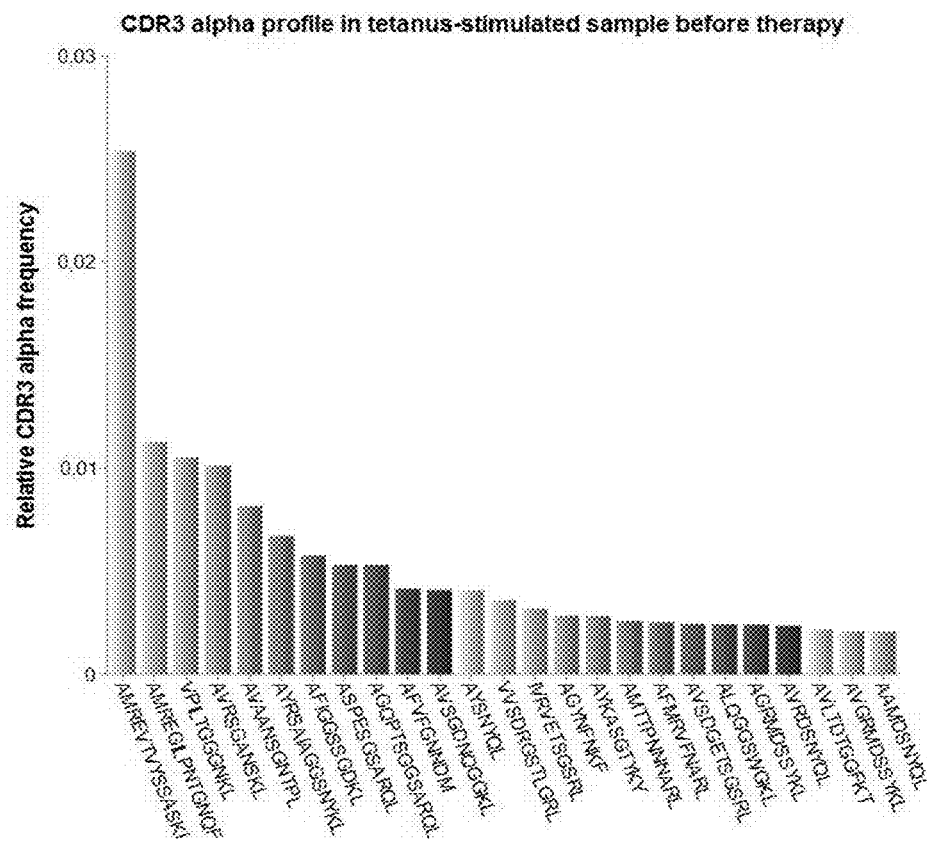
FIG. 5A and FIG. 5B show TCR profiling of TCR-alpha chains before/after vaccination therapy, where PBMCs derived from the blood samples have been stimulated in vitro by Tetanus toxoid antigen mix. The figure shows the patient's CDR3 profile before (FIG. 5A) and after (FIG. 5B) therapy.
Figure 5B:
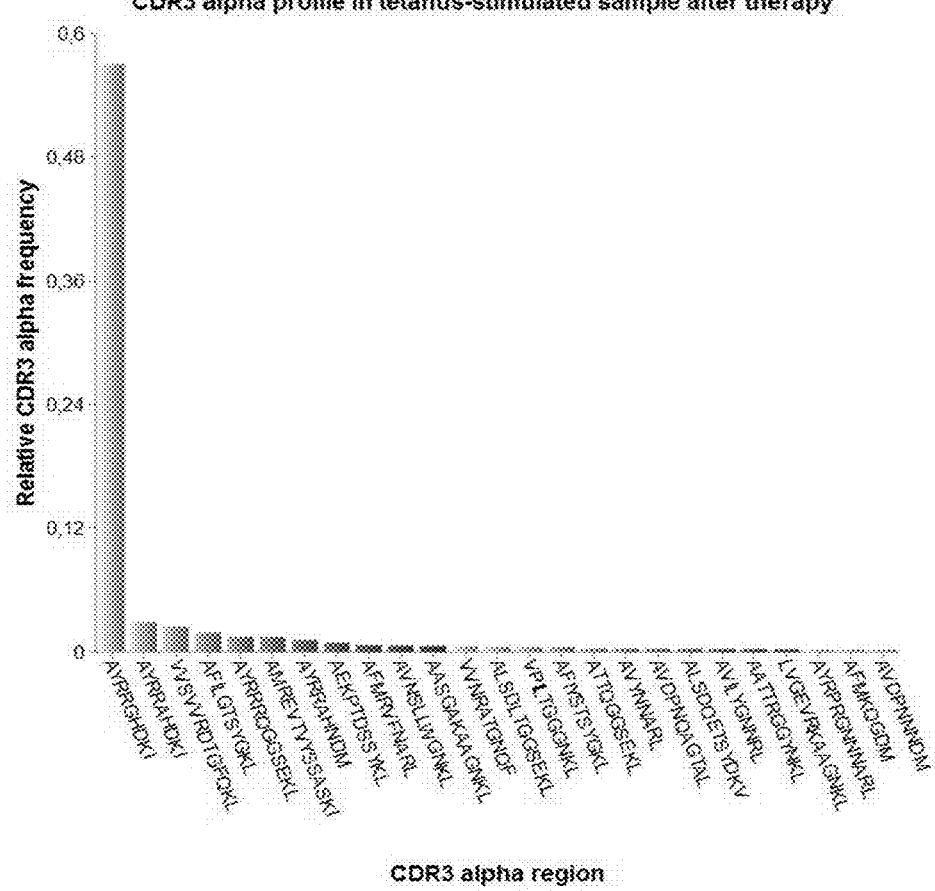
Figure 6A:
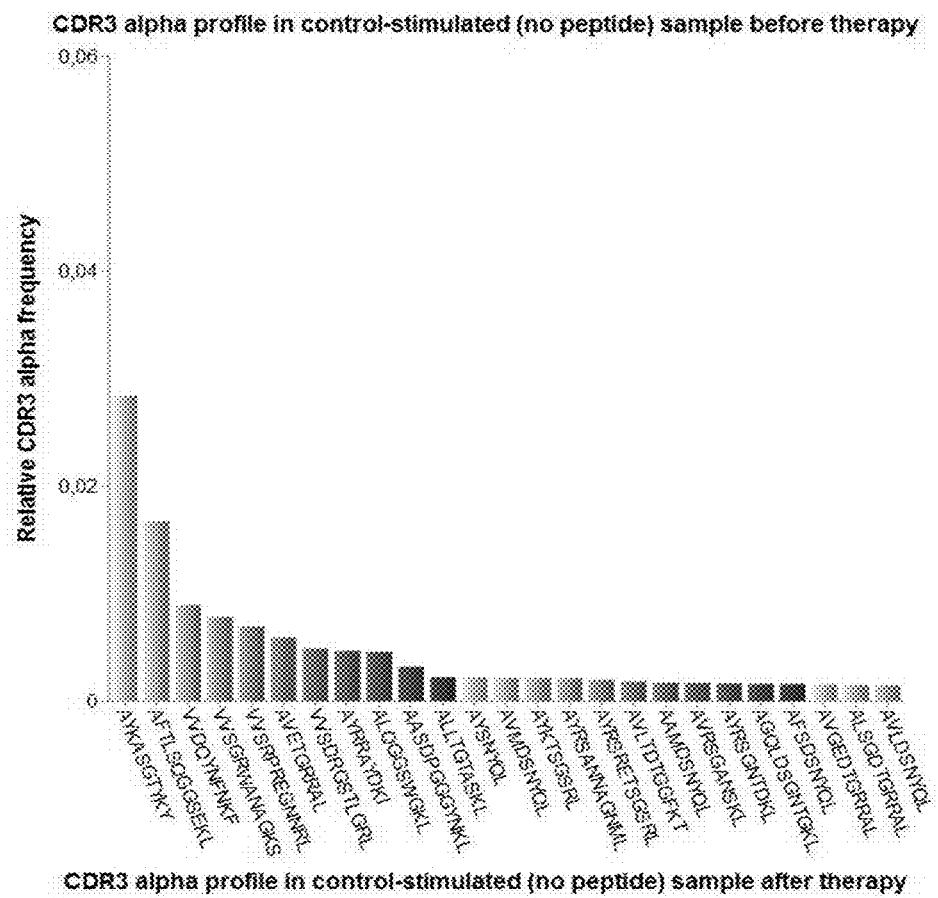
FIG. 6A and FIG. 6B show TCR profiling of TCR-alpha chains before/after vaccination therapy, where PBMCs derived from the blood samples have been cultured in vitro without further stimulation. The figure shows the patient's CDR3 profile before (FIG. 6A) and after (FIG. 6B) therapy.
Figure 6B:
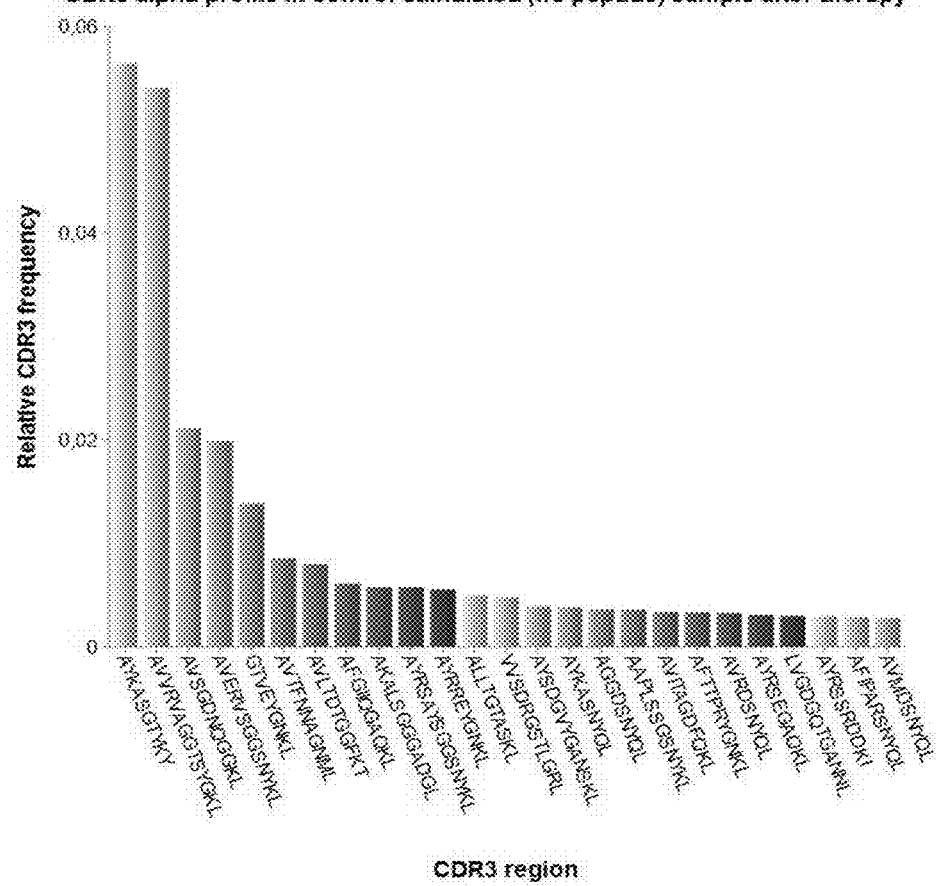
Figure 8A:
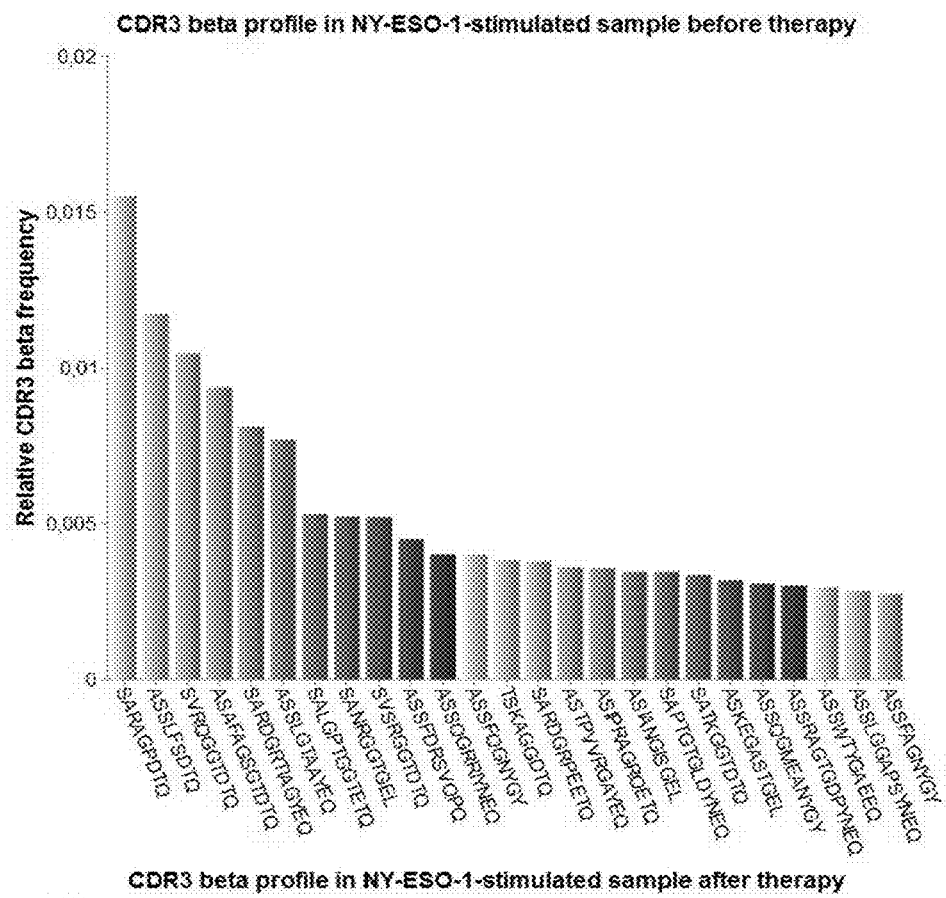
FIG. 8A and FIG. 8B show TCR profiling of TCR-beta chains before/after vaccination therapy, where PBMCs derived from the blood samples have been stimulated in vitro by NY-ESO-1 antigen mix. The figure shows the patient's CDR3 profile before (FIG. 8A) and after (FIG. 8B) therapy.
Figure 8B:
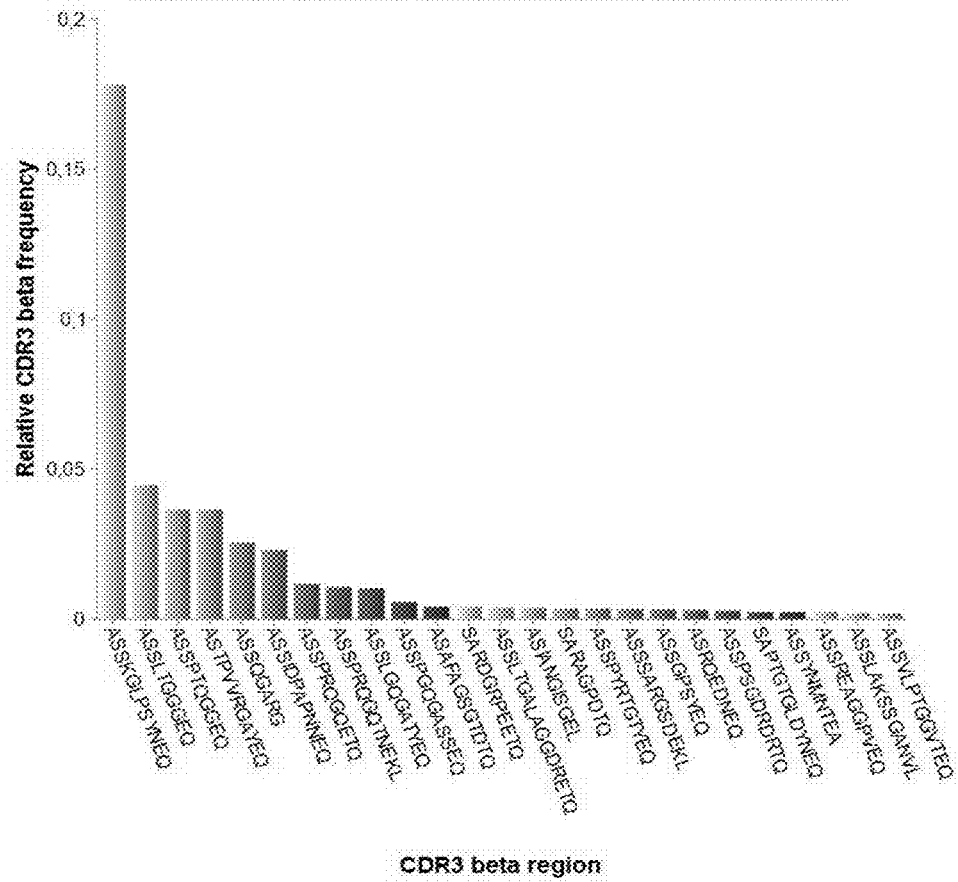
Figure 9A:
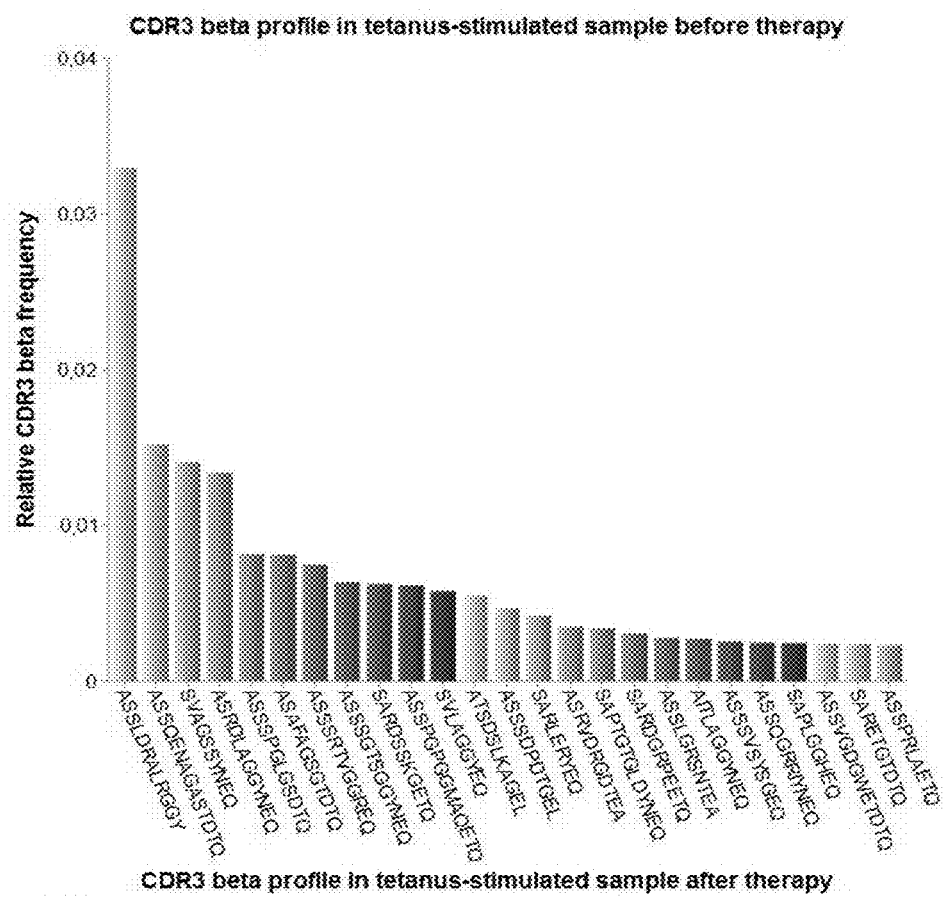
FIG. 9A and FIG. 9B show TCR profiling of TCR-beta chains before/after vaccination therapy, where PBMCs derived from the blood samples have been stimulated in vitro by Tetanus toxoid antigen mix. The figure shows the patient's CDR3 profile before (FIG. 9A) and after (FIG. 9B) therapy.
Figure 9B:
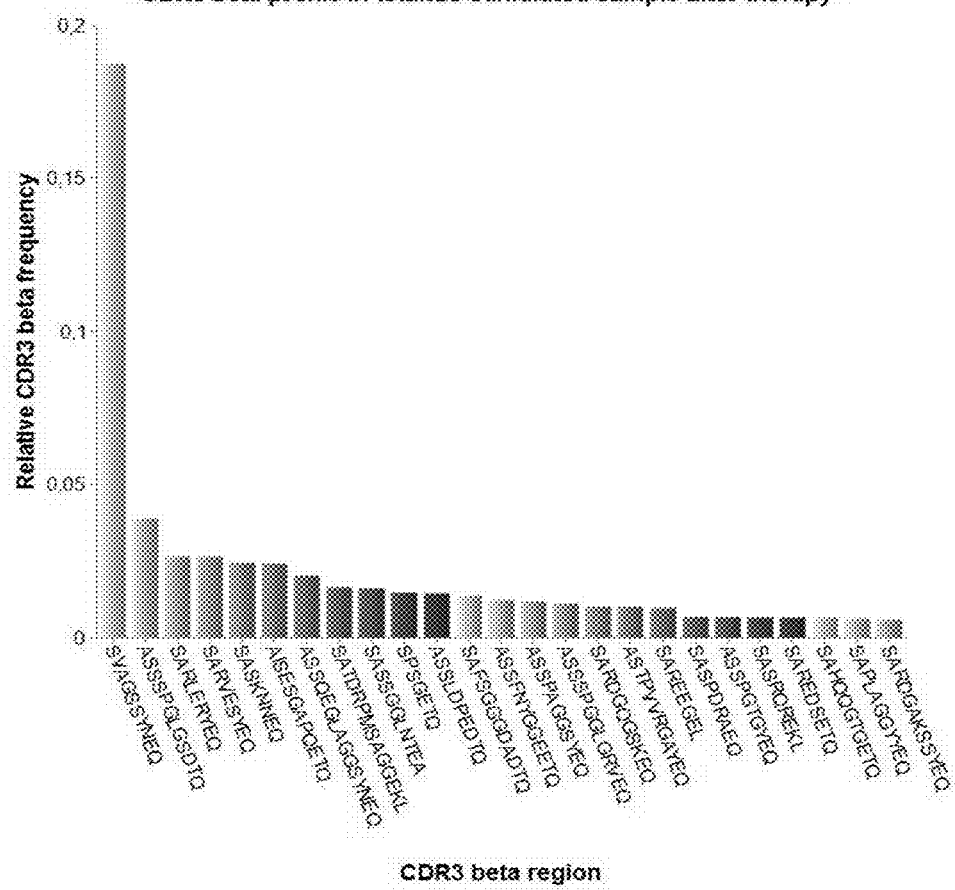
Figure 10A:
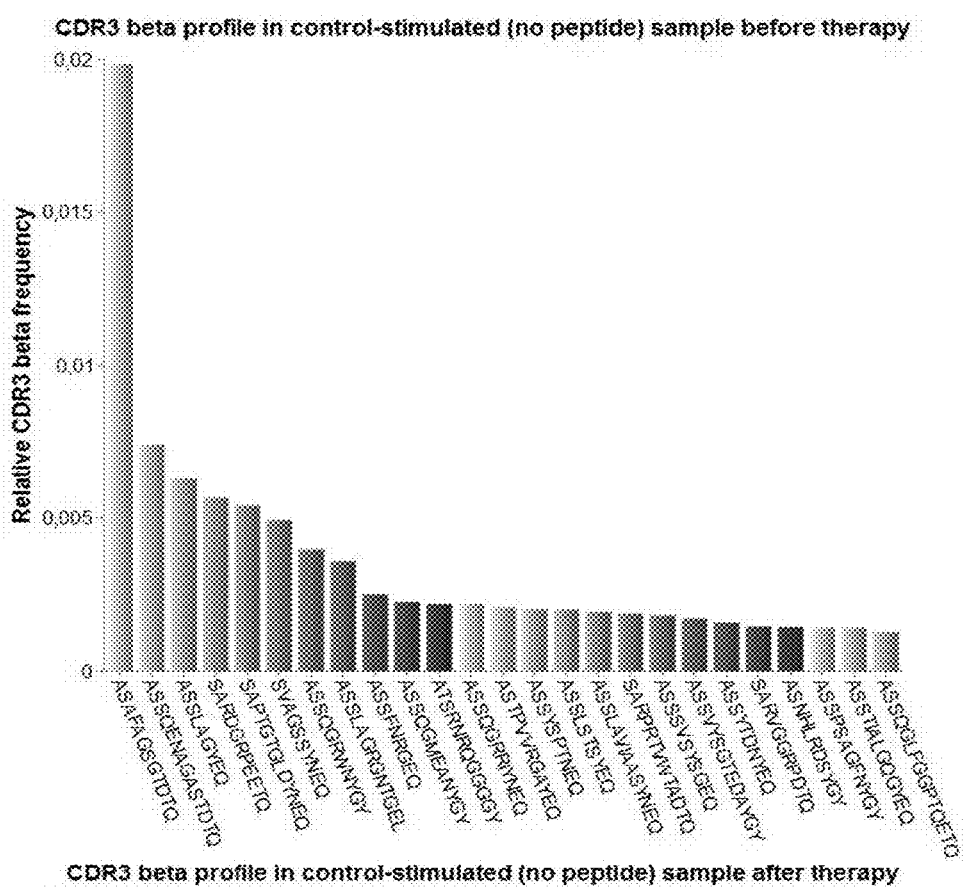
FIG. 10A and FIG. 10B show TCR profiling of TCR-beta chains before/after vaccination therapy, where PBMCs derived from the blood samples have been cultured in vitro without further stimulation. The figure shows the patient's CDR3 profile before (FIG. 10A) and after (FIG. 10B) therapy.
Figure 10B:
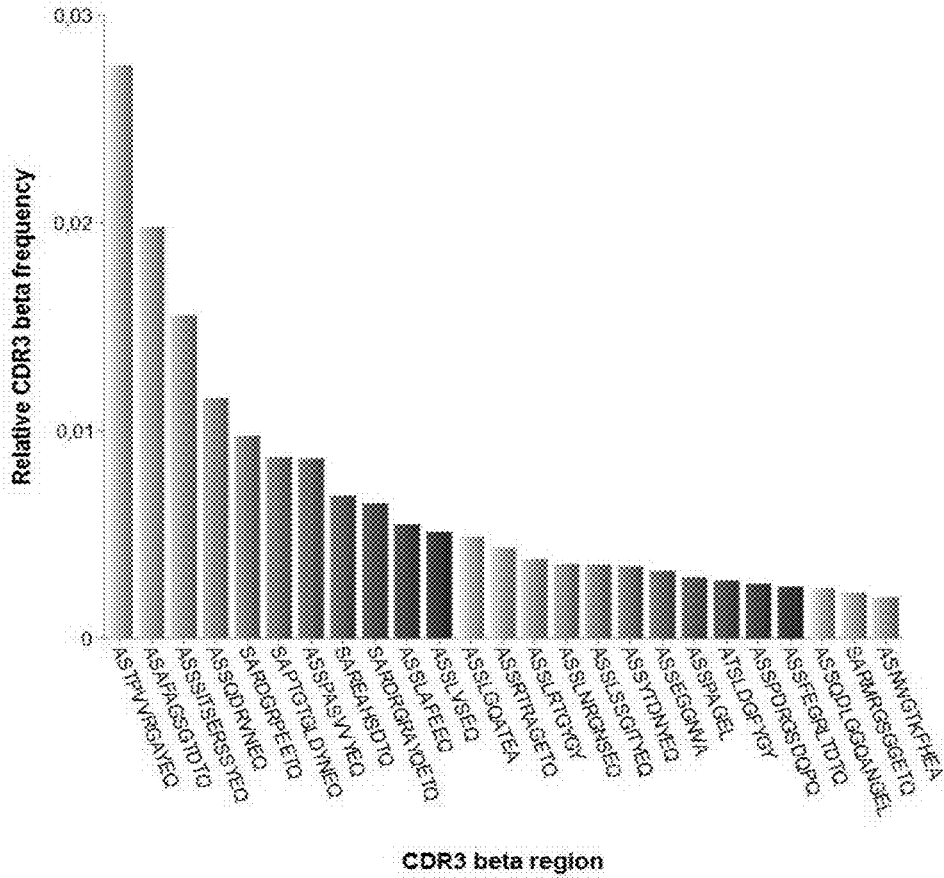
Figures 11A, 11B:
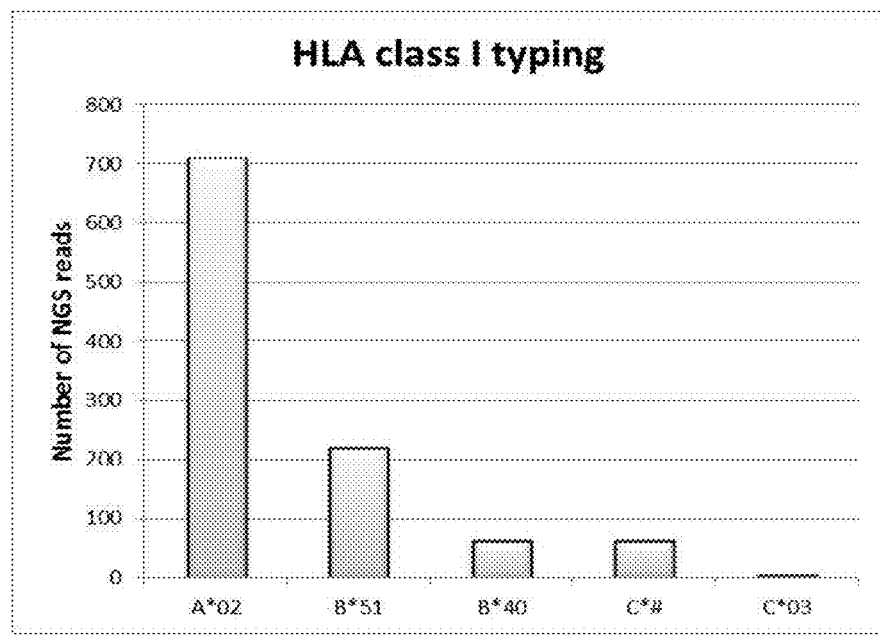
FIG. 11A and FIG. 11B show HLA typing for a patient in vaccination therapy.

For NY-ESO-1 stimulated sample major repertoire shift is observed in the post-therapy sample due to expansion of NY-ESO-1 responder clones (FIGS. 4 and 8). Similarly, for tetanus-stimulated sample a major repertoire shift is observed in the post-therapy sample due to expansion of tetanus responder clones (FIGS. 5 and 9). In control stimulation with no peptide (FIGS. 6 and 10), the profiles before/after differ to some extent between the samples, but the difference is not as strong as for the tetanus and NY-ESO-1 response. The observed differences may come from the fact, that some clones in cell culture randomly expand while some become less frequent than in the beginning. The HLA profile of the patient has been determined in parallel. The patient is homozygous for HLA-A*02, and heterozygous for HLA-B and C, wherein he/she expresses the alleles B*51, B*40, C*03 and either C*14 or C*01 (FIG. 11).

Example 6

Quantitative Measurement of HLA IVT mRNA

Different in vitro transcribed mRNAs coding for a set of representative HLA isotypes were used for template-switch-based 5'rapid amplification of cDNA with HLA specific primers. For this purpose the mRNAs were diluted and mixed in different proportions to show the increase of one allele in a mix of six alleles. The applied mRNA concentrations were in a concentration resembling a physiological mRNA level range (amounts found in a real sample). Using the HLA protocol the created cDNAs were amplified in two steps. Afterwards the PCR products were separated by gel electrophoresis, excised, purified, subjected to library preparation and sequenced with the Illumina MiSeq System.

Each of the three experimental series varying the quantitative level of one allele HLA-A, B or C (FIGS. 12-14) show a linear correlation between the detected sequence reads of a specific allele (normalized to the total annotated HLA reads) and the relative content (in percentage) of the allele in the IVT mRNA mix.

As expected with the increase of reads corresponding to the varying allele the percentage of reads for other alleles decreases or stays constant.

Example 7

Dose-Dependent Induction of T Cell Recognition by Titrated HLA-RNA Transfection

The following example shows that an effective immune response decisively depends on HLA expression and T cell proliferation and that both parameters can be conveniently determined by the method of invention also compared to conventional methods. In detail this experiment shows the titrated induction of antigen-specific T cell reactivity as a function of different levels of HLA-A*0201 expression that are detectable using the TCR profiling kit. Expression of different HLA-A*0201 levels was achieved by transfection of K562-B*0702 cells with titrated amounts of HLA-A*0201 RNA (0, 0.05, 0.1, 0.5, 2 µg) and was confirmed by FACS analysis after staining with a HLA-A*0201-specific antibody. Additionally, transfected cells were collected 3 h post-transfection for HLA mRNA analysis by sequencing. CD8+ T cells derived from a buffy coat of a HLA-A*0201/B*0702 expressing and Cytomegalovirus positive (CMV+) individual were co-cultured with HLA-A*0201-RNA transfected K562-B*0702 cells pulsed either with the immunodominant HLA-A*0201-restricted T cell epitope CMV-pp65-495-503 (NLV) or a control peptide. After overnight co-culture, cells were analyzed for titrated induction of IFNγ secretion by IFNγ-ELISPOT assay. Furthermore, cells cocultured for an extended period of six days were analyzed for enrichment of CMV-pp65-495-503-specific CD8+ T cells by dextramer staining.

For HLA analysis the RNA of K562 cells transfected with titrated amounts of HLA-A*0201 RNA (collected 3 h post-transfection) was mixed with RNA from CD8+ cells to provide more diverse HLA background as reference for HLA-A*0201 quantification. Since the HLA-A*0201 sequence used for transfection was sequence-optimized for efficient protein expression it could be differentiated in silico from the native sequence on mRNA level. The samples were processed using a combined TCR-HLA protocol. Co-cultures over six days of T cells and K562 cells were used for RNA isolation and were subjected to TCR profiling.

Figure 15A:
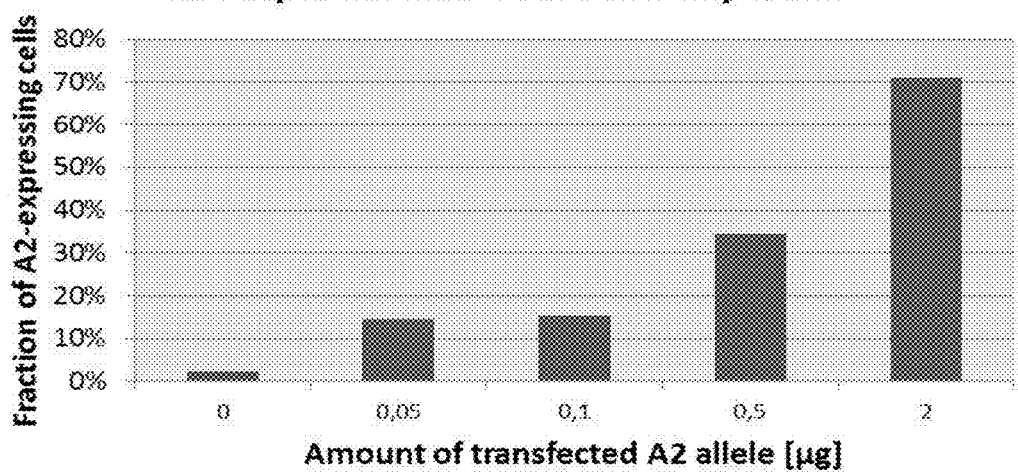
FIG. 15A and FIG. 15B show quantitative measurement of HLA expression in K562.
Figure 15B:
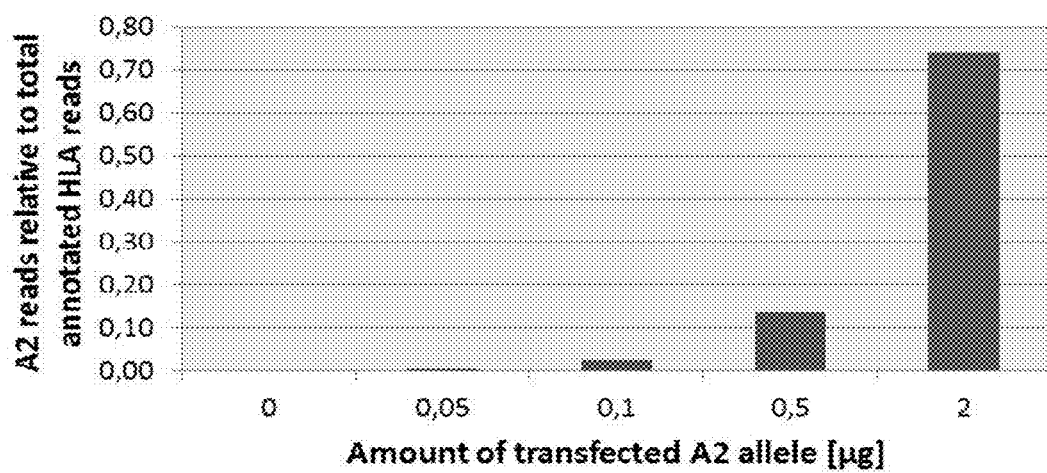
Figure 16A:
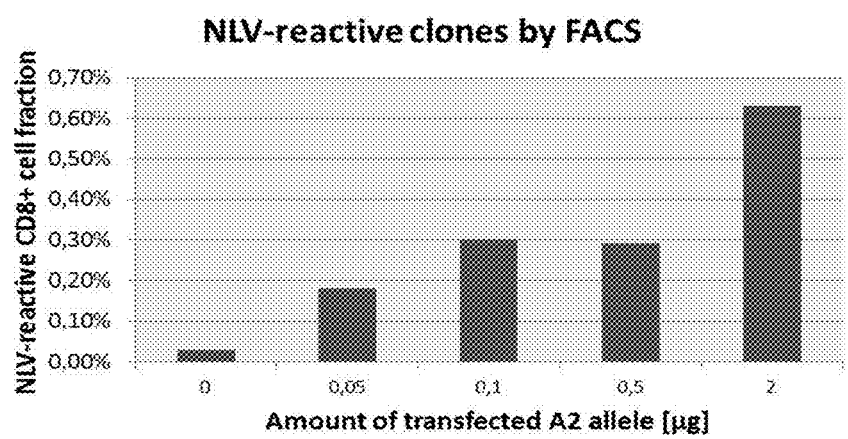
FIG. 16A, FIG. 16B, and FIG. 16C show monitoring of T cell proliferation and T cell receptor profiling.
Figure 16B:
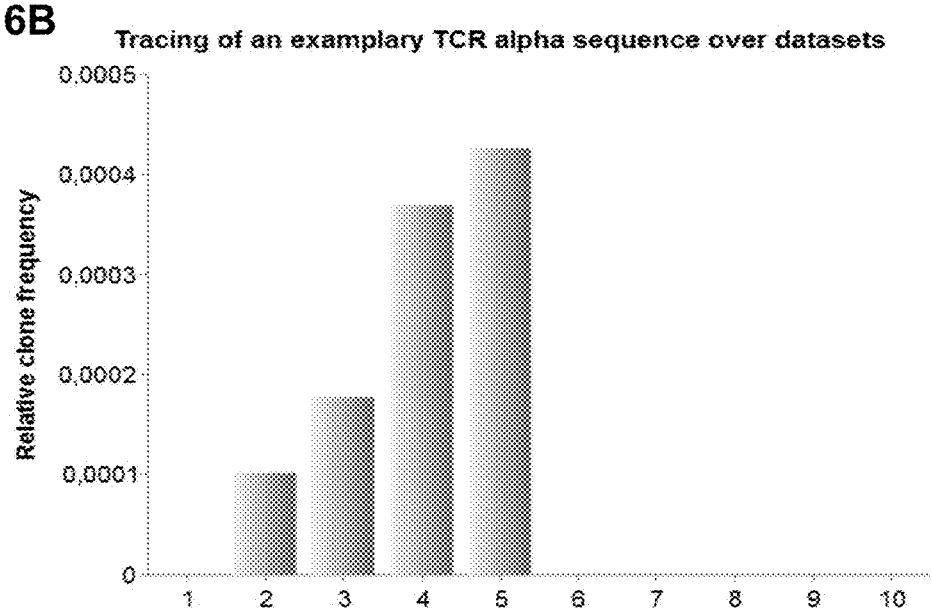
Figure 16C:
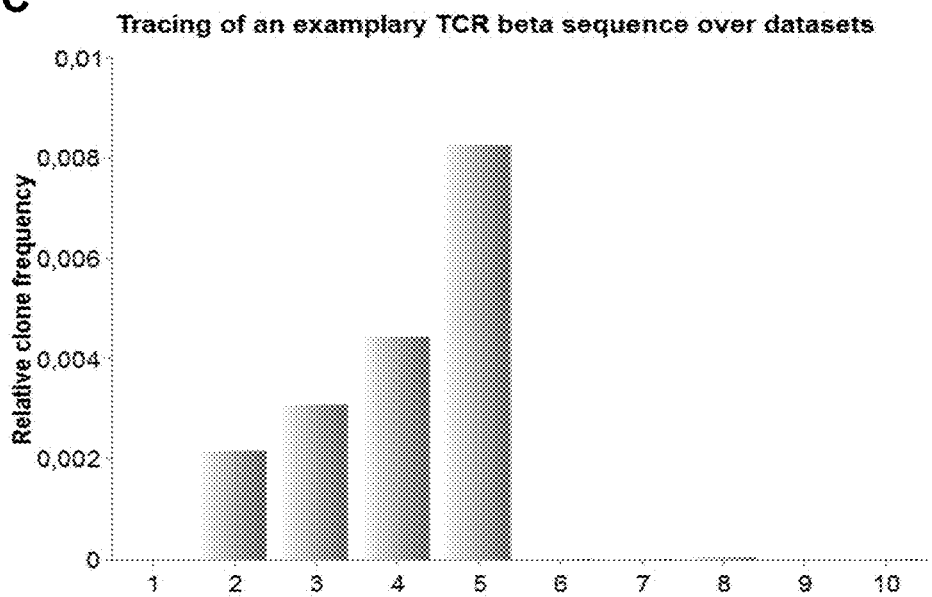

Both FACS data (FIG. 15A) and sequencing data (FIG. 15B) confirmed increasing amount of HLA-A*0201 allele on protein and mRNA level, respectively, correlating with increasing amount of transfected mRNA. Fraction of NLV-reactive T cells among CD8+ cells increased in response to presented NLV peptide positively correlating to the amount of transfected HLA-A*0201 mRNA, as measured by FACS (FIG. 16A). Expected sequence frequency patterns across the samples (low/undetectable presence in control peptide-pulsed K562 cell cocultures and HLA-A*0201-dependent increase in NLV-pulsed K562 cell cocultures) are represented in FIGS. 16B and C for exemplary TCR alpha and TCR beta clone sequences. Thus the method of invention facilitates the determination of the decisive parameters to predict an effective immune response.

Figure 17A:
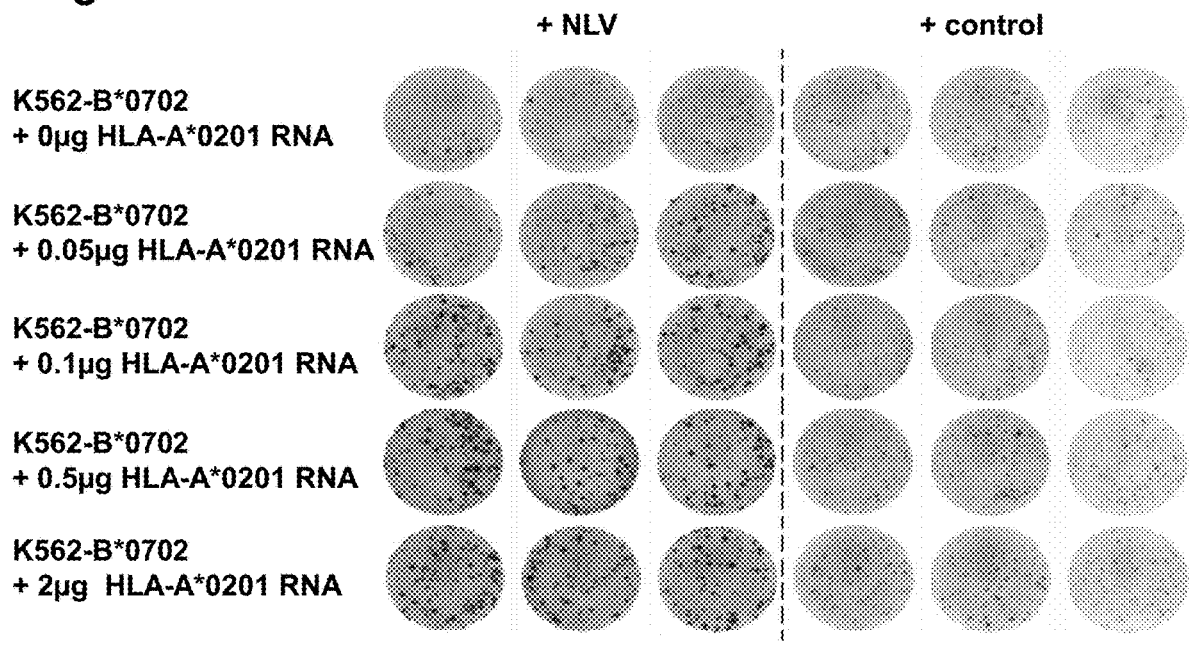
FIG. 17A and FIG. 17B show Monitoring immune response effects by cytokine release and cytotoxicity.
Figure 17B:
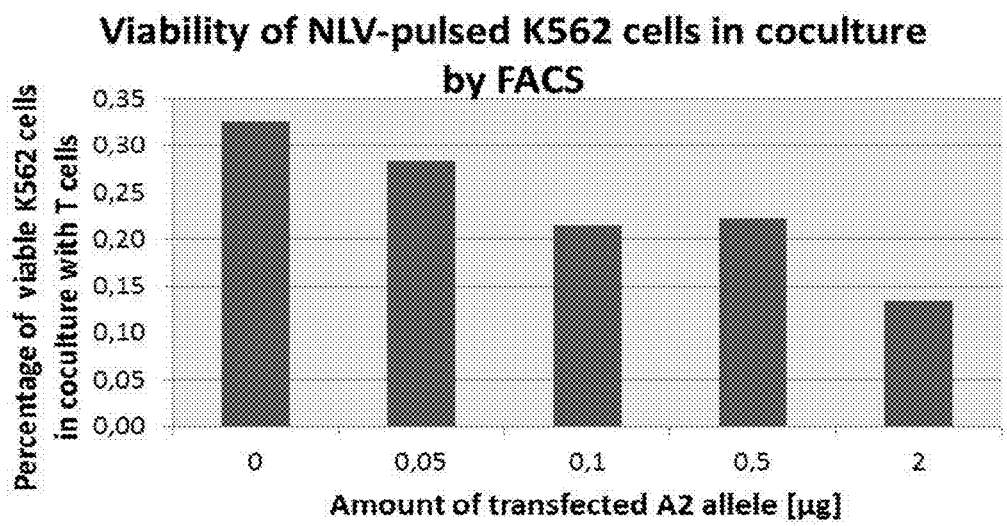

In ELISPOT assay cocultures of NLV-pulsed K562 cells showed higher IFNγ secretion (increasing with the amount of transfected HLA-A*0201 mRNA) as compared to control peptide-pulsed K562 cells (FIG. 17A). As a result of T cell activation the percentage of viable HLA-A*0201-expressing NLV-pulsed K562 cells in coculture decreased with increasing amount of transfected HLA-A*0201 mRNA, as measured by FACS (FIG. 17B). This shows that an effective immune response has occurred in this model system.

Example 8

Monitoring of Melanoma Patients Treated by Vaccine-Based Immunotherapy

The above described method is used for monitoring an immune response in 2 melanoma patients that were treated by an immunotherapy based on a peptide vaccine consisting of the HLA-B*0702-restricted T cell epitope ATPMEAEL-ARRSLAQ (aa97-111) (SEQ ID NO: 40) of the tumor-associated antigen NY-ESO 1. In order to evaluate whether or not patients would benefit from a corresponding peptide vaccination therapy, HLA genotyping is done to test for HLA-B*0702 and tumor biopsies are examined for high NY-ESO 1 expression.

Before the vaccination therapy is started, the method described herein above is applied to establish HLA- and TCR-specific gene expression profiles of the patient's PBMCs. Furthermore the tumor size/mass is determined by CT scan. During therapy, the patients received 1 mg of the HLA-B*0702-restricted peptide ATPMEAELARRSLAQ (SEQ ID NO: 40) every 2 weeks for 6 doses.

4 and 12 weeks after the last vaccination the tumor size is determined by CT scan and HLA- and TCR-specific gene expression profiles are generated from patient's PBMCs using the method of the present invention. In addition HLA-expression profiles are established from tumor biopsies that are taken from the patients 12 weeks after the last vaccination. At all time points the different isotypes of HLA class I and II are expressed at normal levels that did not differ significantly to previously determined expression levels in various PBMC samples.

By comparing TCR gene expression profiles 6 weeks after vaccination to that before treatment, a strongly increased expression of the TCR-α sequence V1.1 J23 C is observed and an increased expression of the TCR-β sequence V4.1 D2 J2.1 C2 in patient's PBMCs is observed, strongly suggesting that these sequences form the dominant T cell clone responding to the vaccination. In detail, in the PMBCs of patient 1 the expression of the TCR-α sequence V1.1 J23 C is increased to 10.3-fold and the expression of the TCR-β sequence V4.1 D2 J2.1 C2 is increased to 9.6-fold. The PBMCs of patient 2 show a 9.3-fold increased expression of the TCR-α sequence V1.1 J23 C and a 10.6-fold increased expression of the TCR-β sequence V4.1 D2 J2.1 C2.

Along with the induced T cell response detected by the altered TCR profile, a loss of the tumor mass is seen in the CT scan of both patients. This leads to the conclusion that the vaccine therapy induced a specific T cell response resulting in tumor regression. To proof that the identified enriched TCR sequences form a functional antigen-specific TCR that is responsible for the antitumor effect, the TCR gene sequences are isolated and cloned into a retroviral vector for stable transfection of K562 cells. Using an interferon-gamma ELIspot assay the TCR-transgenic cells can be shown to recognize target cells pulsed with the NY-ESO 1 peptide ATPMEAELARRSLAQ specifically. Using an interferon-gamma ELIspot assay the TCR-transgenic cells can be shown to recognize target cells pulsed with the NY-ESO 1 peptide ATPMEAELARRSLAQ (SEQ ID NO: 40) specifically.

12 weeks after vaccination, the TCR expression profile of the PBMCs of patient 1 is similar to that after 6 weeks, showing a 9- to 10-fold increased expression of the TCR-α sequence V1.1 J23 and the TCR-β sequence V4.1 D2 J2.1 C2 compared to the expression profile before vaccination. The TCR expression profile 12 weeks after vaccination of the PBMCs of patient 2, however, significantly differs from that of 6 weeks after vaccination, reflected by a decreased expression of the dominant TCR. Compared to the TCR expression profile before vaccination, the expression TCR-α sequence V1.1 J23 and the TCR-β sequence V4.1 D2 J2.1 C2 was only 2 to 3-fold increased.

Interestingly, the CT scan of patient 1 reveals a continuous tumor regression whereas the tumor of patient 2 is growing again. For further investigation new biopsies of the tumors of both patients are taken for analysis of tumor antigen expression and the establishment of a HLA expression profile using the method of the present invention. The investigated tumor cells of patient 1 show a high tumor antigen expression and a normal HLA expression profile. Cells from the tumor biopsy of patient 2 also express the tumor antigen at high levels but the HLA expression profile is altered. HLA-A, C as well as class 2 alleles are expressed at normal levels but expression of HLA-B*0702 is completely lost.

The loss of HLA-B*0702 expression in tumor cells of patient 2 may explain the lack of a long-term tumor control that the vaccine-based immunotherapy tried to establish in the patient.

By using the method of the present invention we could, thus, identify an immune escape of a patient's tumor in response to a vaccine-based immunotherapy.

The invention claimed is:

1. A method for detecting and quantifying individual HLA isotypes and individual T cell receptor α- and β-chains from a single biological sample comprising the steps of:
   (a) obtaining a single biological sample from a human subject;
   (b) determining, from the single biological sample, a nucleotide sequence of mRNA encoding HLA-A, HLA-B and HLA-C and a nucleotide sequence of mRNA encoding T cell receptor α- and β-chains transcribed from recombined T cell receptor loci, wherein step (b) comprises:
   (i) generating, from mRNA encoding HLA-A, HLA-B, or HLA-C, a first cDNA strand, the first cDNA strand having a 3' poly (C) sequence comprising at least 3 C nucleotides at the 3' end of the cDNA strand, which poly (C) sequence serves as a target sequence for a template switching oligonucleotide, wherein the template switching oligonucleotide comprises at least 3 G nucleotides and serves as a matrix for the elongation of the first cDNA strand at the 3' end of the poly (C) sequence and introduces a primer binding site at the 3' end of the first cDNA strand, and (ii) reproducing the cDNA by polymerase chain reaction, with a forward primer which is capable of hybridizing to the primer binding site; and (c) quantifying the individual HLA isotypes and individual T cell receptor chains from the single biological sample.

2. The method of claim 1, wherein step (b)(i) comprises reverse transcription of mRNAs encoding HLA-A, HLA-B and HLA-C with a primer hybridizing to a target sequence within exon 3 or exon 4 of HLA-I and a reverse transcriptase that has terminal transferase activity.

3. The method of claim 2, wherein the primer hybridizing to a target sequence within exon 3 or exon 4 of HLA-I comprises the nucleotide sequence of SEQ ID NO: 8 or SEQ ID NO: 29.

4. A method of treating the subject by adoptive T cell therapy, comprising administering to the subject a T cell, said T cell having individual T cell receptor α- and β-chains identified and quantified by a method as defined in claim 1, wherein said subject has or is suspected of having a disease or condition characterized by an antigen recognized by said T cell.

5. The method of claim 1, wherein the single biological sample is obtained from the subject after the subject has been exposed to a tumor-associated antigen.

6. The method of claim 5, wherein the tumor-associated antigen is expressed in at least tissue from which the sample has been obtained.

7. A method for detecting and quantifying individual HLA isotypes and individual T cell receptor α- and β-chains from a single biological sample comprising the steps of:
  (a) obtaining a single biological sample from a human subject;
  (b) determining, from the single biological sample, a nucleotide sequence of mRNA encoding HLA-A, HLA-B and HLA-C and a nucleotide sequence of mRNA encoding T cell receptor α- and β-chains transcribed from recombined T cell receptor loci,
  wherein step (b) comprises:
    (i) generating, from mRNA encoding a TCRα chain or TCRβ chain, a first cDNA strand, the first cDNA strand having a 3' poly (C) sequence comprising at least 3 C nucleotides at the 3' end of the cDNA strand, which poly (C) sequence serves as a target sequence for a template switching oligonucleotide, wherein the template switching oligonucleotide comprises at least 3 G nucleotides and serves as a matrix for the elongation of the first cDNA strand at the 3' end of the poly (C) sequence and introduces a primer binding site at the 3' end of the first cDNA strand, and
    (ii) reproducing the cDNA by polymerase chain reaction, with a forward primer which is capable of hybridizing to the primer binding site.

8. The method of claim 7, wherein step (b)(i) comprises reverse transcription of mRNAs encoding T cell receptor chains with a primer hybridizing to a target sequence within a constant region of the respective T cell receptor chain and a reverse transcriptase that has terminal transferase activity.

9. The method of claim 8, wherein the primer hybridizing to a target sequence within a constant region of the respective T cell receptor chain comprises the nucleotide sequence of SEQ ID NO: 6 or SEQ ID NO: 7.

10. A method of treating the subject by adoptive T cell therapy, comprising administering to the subject a T cell, said T cell having individual T cell receptor α- and β-chains identified and quantified by a method as defined in claim 7, wherein said subject has or is suspected of having a disease or condition characterized by an antigen recognized by said T cell.

11. The method of claim 7, wherein the single biological sample is obtained from the subject after the subject has been exposed to a tumor-associated antigen.

12. The method of claim 11, wherein the tumor-associated antigen is expressed in at least tissue from which the sample has been obtained.

13. A method for detecting and quantifying individual HLA isotypes and individual T cell receptor α- and β-chains from a single biological sample comprising the steps of:
  (a) obtaining a single biological sample from a human subject;
  (b) determining, from the single biological sample, a nucleotide sequence of mRNA encoding HLA-A, HLA-B and HLA-C and a nucleotide sequence of mRNA encoding T cell receptor α- and β-chains transcribed from recombined T cell receptor loci,
  wherein step (b) comprises:
    (i) generating, from mRNA encoding HLA-A, HLA-B, or HLA-C, an HLA-first cDNA strand, the HLA-first cDNA strand having a 3' poly (C) sequence comprising at least 3 C nucleotides at the 3' end of the HLA-first cDNA strand, which poly (C) sequence serves as a target sequence for a template switching oligonucleotide, wherein the template switching oligonucleotide comprises at least 3 G nucleotides and serves as a matrix for the elongation of the HLA-first cDNA strand at the 3' end of the poly (C) sequence and introduces a primer binding site at the 3' end of the HLA-first cDNA strand,
    (ii) generating, from mRNA encoding a TCRα chain or TCRβ chain, a TCR-first cDNA strand, the TCR-first cDNA strand having a 3' poly (C) sequence comprising at least 3 C nucleotides at the 3' end of the TCR-first cDNA strand, which poly (C) sequence serves as a target sequence for a template switching oligonucleotide, wherein the template switching oligonucleotide comprises at least 3 G nucleotides and serves as a matrix for the elongation of the TCR-first cDNA strand at the 3' end of the poly (C) sequence and introduces a primer binding site at the 3' end of the TCR-first cDNA strand, and
    (iii) reproducing the HLA-cDNA and TCR-cDNA by polymerase chain reaction, with a primer which is capable of hybridizing to the respective primer binding sites.

14. The method of claim 13, wherein step (b)(i) comprises reverse transcription of mRNAs encoding HLA-A, HLA-B and HLA-C with a primer hybridizing to a target sequence within exon 3 or exon 4 of HLA-I and a reverse transcriptase that has terminal transferase activity.

15. The method of claim 13, wherein step (b)(ii) comprises reverse transcription of mRNAs encoding T cell receptor chains with a primer hybridizing to a target sequence within a constant region of the respective T cell receptor chain and a reverse transcriptase that has terminal transferase activity.

16. The method of claim 14, wherein the primer hybridizing to a target sequence within exon 3 or exon 4 of HLA-I comprises the nucleotide sequence of SEQ ID NO: 8 or SEQ ID NO: 29.

17. The method of claim 15, wherein the primer hybridizing to a target sequence within a constant region of the respective T cell receptor chain comprises the nucleotide sequence of SEQ ID NO: 6 or SEQ ID NO: 7.

18. A method of treating the subject by adoptive T cell therapy, comprising administering to the subject a T cell, said T cell having individual T cell receptor α- and β-chains identified and quantified by a method as defined in claim 13, wherein said subject has or is suspected of having a disease or condition characterized by an antigen recognized by said T cell.

19. The method of claim 13, wherein the single biological sample is obtained from the subject after the subject has been exposed to a tumor-associated antigen.

20. The method of claim 19, wherein the tumor-associated antigen is expressed in at least tissue from which the sample has been obtained.

\* \* \* \* \*

SEQUENCE LISTING

```
<160> NUMBER OF SEQ ID NOS: 41

<210> SEQ ID NO 1
<211> LENGTH: 1119
<212> TYPE: DNA
<213> ORGANISM: human
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
```

```
<222> LOCATION: (193)..(193)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (256)..(257)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (270)..(273)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (282)..(283)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
```

```
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (362)..(363)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (413)..(414)
<223> OTHER INFORMATION: n is a, c, g, or t
<220> FEATURE:
<221> NAME/KEY: misc_feature
<222> LOCATION: (418)..(419)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (485)..(486)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (524)..(524)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (559)..(560)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
```

-continued

<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (1004)..(1004)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a, c, g, or t

<400> SEQUENCE: 1
atgsbsgtca yggcgccccg aaccstcvtc ctgctrctct bggsrgchst ggccctgacc 60
sagacctggg cnkgctccca ctccatgagg tatttcnnca chdccvtgtc ccggcccggc 120
cgcggdgagc cccgcttcat cncngtgggc tacgtggacg acacvcdgtt cgtgnggttc 180
gacagcgacg ccncgagycn nagrvnggag ccncgggcgc cntggdtrga gcaggagggg 240
ccggagtatt gggacnngva nacacngahn nnnaagnncn anncacagrc tnaccgagng 300
nvcctgngga ncnbgcdcng ctactacaac cagagcgagg ncggdtctca cancntccag 360
annatgtnyg gctgcgacnt ggggncngac gggcgcbtcc tccgcgggya yvnncagnnc 420
gcctacgacg gcaaggatta catcgccctg aangaggacc tghgctcntg gaccgcngcg 480
gacanngcrg ctcagatcac cvagcncaag tgggaggcgg cccntgnggc ggagcagndg 540
agagcctacc tggagggcnn gtgcgtggag tggctccgca gatacctgga gaacgggaag 600
gagacgctgc agcgcdcnga hvvcccmaar acrcayvtga cycaccahvc yvtctctgac 660
catgargcca ccctgaggtg ctgggccctg rgcttctacc ctgcggagat cacactgacc 720
tggcagcggg atggbgagga ccaracycag gacacngagc tygtggagac cagrccdgca 780
ggrgatrgaa ccttccagaa gtgggcvgct gtggtggtgc cttctggava rgagcagaga 840
tacacntgcc atgtdcagca ygagggkytg ccvragcccc tcaccctgag atgggagccr 900
tcttcccagy ccaccrtccc catcgtgggc atyvttgctg gcctggytst cytdgbdgyy 960
vtvdynryyv kngbhgybgt ngbnrcygtd rtgdbkdgka ggangavbdb ndndvgdrra 1020
dvaggrrgbw vctvybvdvm dgcddsvwsy dvcavyvvbs mbsvsksydv tgwbdnbbyy 1080
mhvrbhdswd rwrwrkshtg aatcgcttgt aaagcctga 1119

<210> SEQ ID NO 2

<211> LENGTH: 426
<212> TYPE: DNA
<213> ORGANISM: human
<220> FEATURE:
<221> NAME/KEY: TCRa-constant
<222> LOCATION: (1)..(426)
<223> OTHER INFORMATION: nucleotide sequence encoding the constant
      region of the TCR alpha chain

<400> SEQUENCE: 2

```
gatatccaga accctgaccc tgccgtgtac cagctgagag actctaaatc cagtgacaag      60
tctgtctgcc tattcaccga ttttgattct caaacaaatg tgtcacaaag taaggattct     120
gatgtgtata tcacagacaa aactgtgcta gacatgaggt ctatggactt caagagcaac     180
agtgctgtgg cctggagcaa caaatctgac tttgcatgtg caaacgcctt caacaacagc     240
attattccag aagacacctt cttccccagc ccagaaagtt cctgtgatgt caagctggtc     300
gagaaaagct ttgaaacaga tacgaaccta aactttcaaa acctgtcagt gattgggttc     360
cgaatcctcc tcctgaaagt ggccgggttt aatctgctca tgacgctgcg gctgtggtcc     420
agctga                                                               426
```

<210> SEQ ID NO 3
<211> LENGTH: 533
<212> TYPE: DNA
<213> ORGANISM: human
<220> FEATURE:
<221> NAME/KEY: TCRB1constant
<222> LOCATION: (1)..(533)
<223> OTHER INFORMATION: nucleotide sequence encoding the constant
      region of the TCR b1-chain

<400> SEQUENCE: 3

```
aggacctgaa caaggtgttc ccacccgagg tcgctgtgtt tgagccatca gaagcagaga      60
tctcccacac ccaaaaggcc acactggtgt gcctggccac aggcttcttc cccgaccacg     120
tggagctgag ctggtgggtg aatgggaagg aggtgcacag tggggtcagc acggacccgc     180 agccccctcaa ggagcagccc gccctcaatg actccagata ctgcctgagc agccgcctga     240
gggtctcggc caccttctgg cagaaccccc gcaaccactt ccgctgtcaa gtccagttct     300
acgggctctc ggagaatgac gagtggaccc aggataggc caaacccgtc acccagatcg     360
tcagcgccga ggcctggggt agagcagact gtggctttac ctcggtgtcc taccagcaag     420 ggtcctgtc tgccaccatc ctctatgaga tcctgctagg aaggccacc ctgtatgctg     480 tgctggtcag cgcccttgtg ttgatggcca tggtcaagag aaaggatttc tga           533
```

<210> SEQ ID NO 4
<211> LENGTH: 539
<212> TYPE: DNA
<213> ORGANISM: human
<220> FEATURE:
<221> NAME/KEY: TCRb2constant
<222> LOCATION: (1)..(539)
<223> OTHER INFORMATION: nucleotide sequence encoding the constant
      region of the TCR b2-chain

<400> SEQUENCE: 4

```
aggacctgaa aacgtgttc ccacccgagg tcgctgtgtt tgagccatca gaagcagaga       60
tctcccacac ccaaaaggcc acactggtgt gcctggccac aggcttctac cccgaccacg     120
tggagctgag ctggtgggtg aatgggaagg aggtgcacag tggggtcagc acagacccgc     180 agccccctcaa ggagcagccc gccctcaatg actccagata ctgcctgagc agccgcctga     240
```

-continued

```
gggtctcggc caccttctgg cagaacccc gcaaccactt ccgctgtcaa gtccagttct    300
acgggctctc ggagaatgac gagtggaccc aggatagggc caaacctgtc acccagatcg    360
tcagcgccga ggcctggggt agagcagact gtggcttcac ctccgagtct taccagcaag    420 ggtcctgtc tgccaccatc ctctatgaga tcttgctagg gaaggccacc ttgtatgccg      480
tgctggtcag tgccctcgtg ctgatggcca tggtcaagag aaaggattcc agaggctga     539
```

```
<210> SEQ ID NO 5
<211> LENGTH: 30
<212> TYPE: DNA
<213> ORGANISM: human
<220> FEATURE:
<221> NAME/KEY: TS-chim
<222> LOCATION: (1)..(30)

<400> SEQUENCE: 5
aagcagtggt atcaacgcag agtacgcggg                                      30

<210> SEQ ID NO 6
<211> LENGTH: 20
<212> TYPE: DNA
<213> ORGANISM: human
<220> FEATURE:
<221> NAME/KEY: Step1_TRBC
<222> LOCATION: (1)..(20)
<223> OTHER INFORMATION: TRBC / TRBC_1st Strand

<400> SEQUENCE: 6
cacgtggtcg gggwagaagc                                                 20

<210> SEQ ID NO 7
<211> LENGTH: 25
<212> TYPE: DNA
<213> ORGANISM: human
<220> FEATURE:
<221> NAME/KEY: Step1_TRAC
<222> LOCATION: (1)..(25)
<223> OTHER INFORMATION: TRAC / TRAC_1stStrand_

<400> SEQUENCE: 7
catcagaatc cttactttgt gacac                                           25

<210> SEQ ID NO 8
<211> LENGTH: 24
<212> TYPE: DNA
<213> ORGANISM: human
<220> FEATURE:
<221> NAME/KEY: HLA-I_cDNAex4_as
<222> LOCATION: (1)..(24)
<223> OTHER INFORMATION: HLA-I_cDNAex4_as

<400> SEQUENCE: 8
ctcagrgtgr cytcatggtc agag                                            24

<210> SEQ ID NO 9
<211> LENGTH: 24
<212> TYPE: DNA
<213> ORGANISM: human
<220> FEATURE:
<221> NAME/KEY: HLA-II_cDNAex3_as
<222> LOCATION: (1)..(24)
<223> OTHER INFORMATION: HLA-II_cDNAex3_as

<400> SEQUENCE: 9
cagcatcttg ytctgkgcag attc                                            24
```

<210> SEQ ID NO 10
<211> LENGTH: 23
<212> TYPE: DNA
<213> ORGANISM: human
<220> FEATURE:
<221> NAME/KEY: TS-PCR
<222> LOCATION: (1)..(23)
<223> OTHER INFORMATION: TS-PCR

<400> SEQUENCE: 10
aagcagtggt atcaacgcag agt                                          23

<210> SEQ ID NO 11
<211> LENGTH: 25
<212> TYPE: DNA
<213> ORGANISM: human
<220> FEATURE:
<221> NAME/KEY: TRBCex1-as
<222> LOCATION: (1)..(25)
<223> OTHER INFORMATION: TRBCex1-as, Step2_TRBC

<400> SEQUENCE: 11
ggctcaaaca cagcgacctc gggtg                                        25

<210> SEQ ID NO 12
<211> LENGTH: 28
<212> TYPE: DNA
<213> ORGANISM: human
<220> FEATURE:
<221> NAME/KEY: TRACex1-Ph-as
<222> LOCATION: (1)..(28)
<223> OTHER INFORMATION: TRACex1-Ph-as Step2_TRAC

<400> SEQUENCE: 12
ttagagtctc tcagctggta cacggcag                                     28

<210> SEQ ID NO 13
<211> LENGTH: 21
<212> TYPE: DNA
<213> ORGANISM: human
<220> FEATURE:
<221> NAME/KEY: HLA-I_ex3_as
<222> LOCATION: (1)..(21)
<223> OTHER INFORMATION: HLA-I_ex3_as

<400> SEQUENCE: 13
ctgcggagcs mstccacgca c                                            21

<210> SEQ ID NO 14
<211> LENGTH: 24
<212> TYPE: DNA
<213> ORGANISM: human
<220> FEATURE:
<221> NAME/KEY: DRB_ex3_as
<222> LOCATION: (1)..(24)
<223> OTHER INFORMATION: DRB_ex3_as

<400> SEQUENCE: 14
ccacctgact tcaatgctgc ctgg                                         24

<210> SEQ ID NO 15
<211> LENGTH: 23
<212> TYPE: DNA
<213> ORGANISM: human
<220> FEATURE:
<221> NAME/KEY: DQB_ex3_as
<222> LOCATION: (1)..(23)
<223> OTHER INFORMATION: DQB_ex3_as

```
<400> SEQUENCE: 15
gttgtggtgg ttgagggcct ctg                                      23

<210> SEQ ID NO 16
<211> LENGTH: 28
<212> TYPE: DNA
<213> ORGANISM: human
<220> FEATURE:
<221> NAME/KEY: TS-5N-PCR
<222> LOCATION: (1)..(28)
<223> OTHER INFORMATION: TS-5N-PCR 5N_TS_PCR
<220> FEATURE:
<221> NAME/KEY: misc_feature
<222> LOCATION: (1)..(5)
<223> OTHER INFORMATION: n is a, c, g, or t

<400> SEQUENCE: 16
nnnnnaagca gtggtatcaa cgcagagt                                 28

<210> SEQ ID NO 17
<211> LENGTH: 24
<212> TYPE: DNA
<213> ORGANISM: human
<220> FEATURE:
<221> NAME/KEY: TRBC1nest-as
<222> LOCATION: (1)..(24)
<223> OTHER INFORMATION: TRBC1nest-as Step3_TRBC1

<400> SEQUENCE: 17
cgggtgggaa caccttgttc aggt                                     24

<210> SEQ ID NO 18
<211> LENGTH: 24
<212> TYPE: DNA
<213> ORGANISM: human
<220> FEATURE:
<221> NAME/KEY: TRBC2nest-as
<222> LOCATION: (1)..(24)
<223> OTHER INFORMATION: TRBC2nest-as Step3_TRBC2

<400> SEQUENCE: 18
cgggtgggaa cacgttttttc aggt                                    24

<210> SEQ ID NO 19
<211> LENGTH: 22
<212> TYPE: DNA
<213> ORGANISM: human
<220> FEATURE:
<221> NAME/KEY: TRACnest1-as
<222> LOCATION: (1)..(22)
<223> OTHER INFORMATION: TRACnest1-as Step3_TRAC

<400> SEQUENCE: 19
gtacacggca gggtcagggt tc                                       22

<210> SEQ ID NO 20
<211> LENGTH: 21
<212> TYPE: DNA
<213> ORGANISM: human
<220> FEATURE:
<221> NAME/KEY: HLA-I_ex3_as
<222> LOCATION: (1)..(21)
<223> OTHER INFORMATION: HLA-I_ex3_as

<400> SEQUENCE: 20
ctgcggagcs mstccacgca c                                        21
```

```
<210> SEQ ID NO 21
<211> LENGTH: 24
<212> TYPE: DNA
<213> ORGANISM: human
<220> FEATURE:
<221> NAME/KEY: DRB_ex3_as
<222> LOCATION: (1)..(24)
<223> OTHER INFORMATION: DRB_ex3_as

<400> SEQUENCE: 21
ccacctgact tcaatgctgc ctgg                                          24

<210> SEQ ID NO 22
<211> LENGTH: 23
<212> TYPE: DNA
<213> ORGANISM: human
<220> FEATURE:
<221> NAME/KEY: DQB_ex3_as
<222> LOCATION: (1)..(23)
<223> OTHER INFORMATION: DQB_ex3_as

<400> SEQUENCE: 22
gttgtggtgg ttgagggcct ctg                                           23

<210> SEQ ID NO 23
<211> LENGTH: 23
<212> TYPE: DNA
<213> ORGANISM: human
<220> FEATURE:
<221> NAME/KEY: HLA-I_ex2_s
<222> LOCATION: (1)..(23)
<223> OTHER INFORMATION: HLA-I_ex2_s

<400> SEQUENCE: 23
gctcycaytc catgargtat ttc                                           23

<210> SEQ ID NO 24
<211> LENGTH: 24
<212> TYPE: DNA
<213> ORGANISM: human
<220> FEATURE:
<221> NAME/KEY: DRB_ex1_s
<222> LOCATION: (1)..(24)
<223> OTHER INFORMATION: DRB_ex1_s

<400> SEQUENCE: 24
gacagtgaca ytgayggtgc tgag                                          24

<210> SEQ ID NO 25
<211> LENGTH: 23
<212> TYPE: DNA
<213> ORGANISM: human
<220> FEATURE:
<221> NAME/KEY: DQB1_ex1_s
<222> LOCATION: (1)..(23)
<223> OTHER INFORMATION: DQB1_ex1_s

<400> SEQUENCE: 25
caactgtbac cttgatgctg kcg                                           23

<210> SEQ ID NO 26
<211> LENGTH: 801
<212> TYPE: DNA
<213> ORGANISM: human
<220> FEATURE:
<221> NAME/KEY: DRB1
<222> LOCATION: (1)..(801)
<223> OTHER INFORMATION: Consensus sequence for DRB Locus 1
```

-continued

```
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (117)..(119)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (196)..(197)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (257)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (294)..(295)
<223> OTHER INFORMATION: n is a, c, g, or t
<220> FEATURE:
<221> NAME/KEY: misc_feature
<222> LOCATION: (297)..(299)
<223> OTHER INFORMATION: n is a, c, g, or t
<220> FEATURE:
<221> NAME/KEY: misc_feature
<222> LOCATION: (307)..(308)
```

```
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t

<400> SEQUENCE: 26
atggtgtgtc tgangctccc tggaggctcc tgcatgncag nnctgacagt gacactgatg       60
gtgctgagct ccccactggc tttggctggg gacaccngac cacgtttctt gnngnannnt      120
angnntgagt gtcatttctt caangggacg gagcgggtgc ggttcctgga cagatacttc      180
nataaccang aggagnncgt gcgcttcgac agcgacgtgg gggagtnccg ggcggtgacg      240
gagctggggc ggcctgnngc ngagtactgg aacagccaga aggacntcct ggannannng      300
cgggccnngg tggacaccta ctgcagacac aactacgggg ttgnngagag cttcacagtg      360
cagcggcgag tccatcctaa ggtgactgtg tatccttcaa agacccagcc cctgcagcac      420
cacaacctcc tggtctgntc tgtgagtggt ttctatccag gcagcattga agtcaggtgg      480
ttccggaang gccaggaaga gaagnctggg gtggtgtcca caggcctgat ccanaatgga      540
gactggacct tccagaccct ggtgatgctg gaaacagttc ctcggagtgg agaggtttac      600
acctgccaag tggagcaccc aagcgtgacn agccctctca cagtggaatg gagagcacgg      660
tctgaatctg cacagagcaa gatgctgagt ggagtcgggg gcttngtgct gggcctgctc      720
ttccttgggg ccgggctgtt catctacttc aggaatcaga aggacactc tggacttcag      780 ccaanaggat tcctgagctg a                                                801

<210> SEQ ID NO 27
<211> LENGTH: 801
<212> TYPE: DNA
<213> ORGANISM: human
<220> FEATURE:
<221> NAME/KEY: DRB3-4-5
<222> LOCATION: (1)..(801)
<223> OTHER INFORMATION: Consensus sequence for DRB Loci 3, 4, and 5
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
```

-continued

```
<222> LOCATION: (33)..(34)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (196)..(197)
<223> OTHER INFORMATION: n is a, c, g, or t
<220> FEATURE:
```

```
<221> NAME/KEY: misc_feature
<222> LOCATION: (199)..(200)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (257)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (307)..(308)
<223> OTHER INFORMATION: n is a, c, g, or t
<220> FEATURE:
<221> NAME/KEY: misc_feature
<222> LOCATION: (317)..(318)
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (372)..(373)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
```

<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t

<400> SEQUENCE: 27

```
atggtgtgtc tgaagctccc tggaggctcc ngnntggcag cgntgacagt gacantgang      60
gtgctgagct cccnactggc tttngctggg gacacccnac cacgtttctt gnagcngnnt     120
aagtntgagt gtcatttctt caangggacg gagcgggtgc ggtncctgna naganacntc     180
nataaccang aggagnncnn gcgcttcgac agcgacgtgg gggagtaccg ggcggtgang     240
gagctggggc ggcctgnngc ngagtnctgg aacagccaga aggacntcct ggagcagang     300
cgggncnngg tggacannta ctgcagacac aactacgggg ttgnngagag cttcacagtg     360
cagcggcgag tnnancctna ggtgactgtg tatcctncaa ngacccagnc cctgcagcac     420
cacaacctcc tggtctgctc tgtgantggt ttctatccag cagcattga agtcaggtgg     480 ttccggaacn gccaggaaga gaaggctggg gtggtgtcca cnggcctgat ccagaatgga     540
gactggacct tccagaccct ggtgatgctn gaaacagttc ctcggagtgg agaggtttac     600
acctgccaag tggagcancc aagcntnang agccctctca cagtgnaatg gagngcacgg     660
tctgaatctg cacagagcaa gatgctgagt ggagtcgggg gctttgtgct gggcctgctc     720
ttccttgggn cngggctgtt catctacttc aggaatcaga aggacactc tggacttcag     780 ccaacaggan tcntgagctg a                                                801
```

<210> SEQ ID NO 28
<211> LENGTH: 810
<212> TYPE: DNA

```
<213> ORGANISM: human
<220> FEATURE:
<221> NAME/KEY: DQB1
<222> LOCATION: (1)..(810)
<223> OTHER INFORMATION: Consensus sequence for DQB Locus 1
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t

<400> SEQUENCE: 28
atgtcttgga araagkctttt gcggatcccy ggagrccttc gggyagcaac tgtbaccttg      60
atgctgkcga tsctgagcdc cyyrstggct gagggcagag acyctcccga ggatttcgtg     120
twccagttta aggbcmtgtg ctacttcacc aacgggacvg agcgcgtgcg kbdtgtrasc     180
agahrcatct ataaccgaga rgagdwcgyr cgcttcgaca gcgacgtggr ggwgtwycgs     240
gcggtgacgc ygcwggggcn gcytgnygcc gagtactgga abagccagaa ggamrtcctg     300
gagrrgrmmc grgcgkmgbt ggacasvgtr tgcagacaca actacsagkt ggvgywccgc     360
rsgaycytgc agmggmgagt ggagcccaca gtgaccatct ccccatccag gacagaggcc     420
ctcaaccacc acaacctgct grtctgctcr gtgacagatt tctatccars ccagatcaaa     480
gtccrgtggt ttcggaatga ycaggaggag acarcyggcg ttgtgtccac ccccctyatt     540
aggaayggtg actggacytt ccagatcctg gtgatgctgg aaatgactcc ccagcrtgga     600
gaygtctaca cctgccacgt ggagcacccc agcctccaga rccccatcay cgtggagtgg     660
cgggctcart ctgaatctgc ccagarcaag atgctgagtg gcrttggagg cttcgtgctg     720
gggctsatct tcctygggct kggccttaty atccrtcama ggagtcrgaa aggacctcaa     780
gggcctccac cagcagggct yctgcactga                                       810

<210> SEQ ID NO 29
<211> LENGTH: 20
<212> TYPE: DNA
<213> ORGANISM: human
<220> FEATURE:
<221> NAME/KEY: HLA-I_cDNAex4_as2
<222> LOCATION: (1)..(20)

<400> SEQUENCE: 29
gtgtcctgrg tytggtcctc                                                   20

<210> SEQ ID NO 30
<211> LENGTH: 25
<212> TYPE: DNA
<213> ORGANISM: human
<220> FEATURE:
<221> NAME/KEY: TS-PCR2
<222> LOCATION: (1)..(25)

<400> SEQUENCE: 30
aagcagtggt atcaacgcag agtac                                             25

<210> SEQ ID NO 31
<211> LENGTH: 22
<212> TYPE: DNA
<213> ORGANISM: human
<220> FEATURE:
<221> NAME/KEY: HLA-I_ex1Lank_s3
<222> LOCATION: (1)..(22)
```

<400> SEQUENCE: 31
tggccctgac csagacctgg gc            22

<210> SEQ ID NO 32
<211> LENGTH: 20
<212> TYPE: DNA
<213> ORGANISM: human
<220> FEATURE:
<221> NAME/KEY: HLA-I_ex2Lank_s
<222> LOCATION: (1)..(20)

<400> SEQUENCE: 32
gtgggctacg tggacgrcac            20

<210> SEQ ID NO 33
<211> LENGTH: 25
<212> TYPE: DNA
<213> ORGANISM: human
<220> FEATURE:
<221> NAME/KEY: HLA-I_ex4_as3
<222> LOCATION: (1)..(25)

<400> SEQUENCE: 33
ggtcagtgtg atctccgcag ggtag            25

<210> SEQ ID NO 34
<211> LENGTH: 26
<212> TYPE: DNA
<213> ORGANISM: human
<220> FEATURE:
<221> NAME/KEY: HLA-I_ex3_as8
<222> LOCATION: (1)..(26)

<400> SEQUENCE: 34
tccttcccgt tctycaggtr tctgcg            26

<210> SEQ ID NO 35
<211> LENGTH: 26
<212> TYPE: DNA
<213> ORGANISM: human
<220> FEATURE:
<221> NAME/KEY: HLA-I_ex3_as9
<222> LOCATION: (1)..(26)

<400> SEQUENCE: 35
tccttcccrt tctycaggtr tctgcg            26

<210> SEQ ID NO 36
<211> LENGTH: 30
<212> TYPE: DNA
<213> ORGANISM: human
<220> FEATURE:
<221> NAME/KEY: TS-5N-PCR2
<222> LOCATION: (1)..(30)
<220> FEATURE:
<221> NAME/KEY: misc_feature
<222> LOCATION: (1)..(5)
<223> OTHER INFORMATION: n is a, c, g, or t

<400> SEQUENCE: 36
nnnnnaagca gtggtatcaa cgcagagtac            30

<210> SEQ ID NO 37
<211> LENGTH: 24
<212> TYPE: DNA
<213> ORGANISM: human
<220> FEATURE:

```
<221> NAME/KEY: PCR_B_3.2
<222> LOCATION: (1)..(24)

<400> SEQUENCE: 37
ggtgggaaca ccttgttcag gtcc                                            24

<210> SEQ ID NO 38
<211> LENGTH: 25
<212> TYPE: DNA
<213> ORGANISM: human
<220> FEATURE:
<221> NAME/KEY: PCR_B_4.2
<222> LOCATION: (1)..(25)

<400> SEQUENCE: 38
gggtgggaac acgtttttca ggtcc                                           25

<210> SEQ ID NO 39
<211> LENGTH: 24
<212> TYPE: DNA
<213> ORGANISM: human
<220> FEATURE:
<221> NAME/KEY: Step3_TRAC_2
<222> LOCATION: (1)..(24)

<400> SEQUENCE: 39
tggtacacgg cagggtcagg gttc                                            24

<210> SEQ ID NO 40
<211> LENGTH: 15
<212> TYPE: PRT
<213> ORGANISM: human
<220> FEATURE:
<221> NAME/KEY: aa 97-111 of NY-ESO 1
<222> LOCATION: (1)..(15)

<400> SEQUENCE: 40

Ala Thr Pro Met Glu Ala Glu Leu Ala Arg Arg Ser Leu Ala Gln
1               5                   10                  15

<210> SEQ ID NO 41
<211> LENGTH: 30
<212> TYPE: DNA
<213> ORGANISM: human
<220> FEATURE:
<221> NAME/KEY: TS-chim2 TSO2
<222> LOCATION: (1)..(30)
<223> OTHER INFORMATION: TS-chim2 TSO2
<220> FEATURE:
<221> NAME/KEY: TS-chim2 TSO2
<222> LOCATION: (1)..(30)

<400> SEQUENCE: 41
aagcagtggt atcaacgcag agtacatggg                                      30
```